(12) United States Patent
Li et al.

(10) Patent No.: US 9,518,132 B2
(45) Date of Patent: Dec. 13, 2016

(54) PROTEIN COMPLEXES FOR ANTIGEN BINDING AND METHODS OF USE

(75) Inventors: Zijuan Li, Shanghai (CN); Chun Wu, San Diego, CA (US); Jun Bao, Lafayette, CA (US); Bo Chen, Daly City, CA (US)

(73) Assignee: Altimab Therapeutics, Inc., Lafayette, CA (US)

( * ) Notice: Subject to any disclaimer, the term of this patent is extended or adjusted under 35 U.S.C. 154(b) by 189 days.

(21) Appl. No.: 13/883,282

(22) PCT Filed: Nov. 9, 2011

(86) PCT No.: PCT/US2011/059844
§ 371 (c)(1),
(2), (4) Date: May 3, 2013

(87) PCT Pub. No.: WO2012/064792
PCT Pub. Date: May 18, 2012

(65) Prior Publication Data
US 2013/0230525 A1    Sep. 5, 2013

Related U.S. Application Data

(60) Provisional application No. 61/411,903, filed on Nov. 9, 2010.

(51) Int. Cl.
| | | |
|---|---|---|
| *C07K 16/28* | (2006.01) | |
| *C07K 16/46* | (2006.01) | |
| *C07K 16/00* | (2006.01) | |
| *C07K 16/24* | (2006.01) | |
| *C07K 16/30* | (2006.01) | |
| *C07K 16/40* | (2006.01) | |
| *G01N 33/68* | (2006.01) | |
| *A61K 38/00* | (2006.01) | |
| *A61K 39/00* | (2006.01) | |

(52) U.S. Cl.
CPC ............ *C07K 16/468* (2013.01); *C07K 16/00* (2013.01); *C07K 16/248* (2013.01); *C07K 16/2803* (2013.01); *C07K 16/2809* (2013.01); *C07K 16/2878* (2013.01); *C07K 16/30* (2013.01); *C07K 16/40* (2013.01); *C07K 16/46* (2013.01); *G01N 33/6854* (2013.01); *A61K 38/00* (2013.01); *A61K 2039/505* (2013.01); *C07K 2317/30* (2013.01); *C07K 2317/31* (2013.01); *C07K 2317/522* (2013.01); *C07K 2317/524* (2013.01); *C07K 2317/526* (2013.01); *C07K 2317/53* (2013.01); *C07K 2317/66* (2013.01); *C07K 2317/73* (2013.01)

(58) Field of Classification Search
CPC ... C07K 16/00; C07K 16/248; C07K 16/2803; C07K 16/2809; C07K 16/2878; C07K 16/46; C07K 2317/30; C07K 2317/31; C07K 2317/524; C07K 2317/521; C07K 2317/53; C07K 2317/66; C07K 16/468; C07K 2317/52; C07K 2317/56; C07K 2317/622; C07K 6/248; C07K 16/30; C07K 16/40; C07K 16/484; C07K 2317/525; C07K 2317/526; C07K 2317/73; A61K 38/00; A61K 39/505; A61K 2039/505
See application file for complete search history.

(56) References Cited

U.S. PATENT DOCUMENTS

| | | | |
|---|---|---|---|
| 5,821,333 A | 10/1998 | Carter et al. | |
| 6,809,185 B1 * | 10/2004 | Schoonjans | C07K 16/00 530/387.1 |
| 7,087,411 B2 * | 8/2006 | Daly | C07K 14/71 435/252.3 |
| 7,754,208 B2 * | 7/2010 | Ledbetter | C07K 16/3061 424/133.1 |
| 7,833,531 B2 * | 11/2010 | O'Neil | A61K 38/26 424/178.1 |
| 8,021,661 B2 * | 9/2011 | Glaser | A61K 47/48384 424/133.1 |
| 8,338,376 B2 * | 12/2012 | Beckman | C07K 14/70578 424/278.1 |
| 2004/0121415 A1 | 6/2004 | King et al. | |
| 2005/0163782 A1 | 7/2005 | Glaser et al. | |
| 2007/0287170 A1 | 12/2007 | Davis et al. | |
| 2007/0298041 A1 | 12/2007 | Tomlinson | |
| 2008/0008713 A1 | 1/2008 | Brewis | |
| 2009/0022642 A1 | 1/2009 | Kanno et al. | |
| 2009/0148447 A1 * | 6/2009 | Ledbetter et al. | ......... 424/134.1 |
| 2009/0252729 A1 | 10/2009 | Farrington et al. | |
| 2009/0304696 A1 | 12/2009 | Lawson et al. | |
| 2010/0150916 A1 | 6/2010 | Pfizenmaier et al. | |

FOREIGN PATENT DOCUMENTS

| | | |
|---|---|---|
| CN | 1842538 A | 10/2006 |
| CN | 1842539 A | 10/2006 |
| EP | 1049787 B1 | 11/2004 |

(Continued)

OTHER PUBLICATIONS

Jubala et al., Vet Pathol 42: 468-476, 2005.*
Yu et al., Investigative Ophthalmology & Visual Science 49(2): 522-527, Feb. 2008.*
Stancovski et al., PNAS 88: 8691-8695, 1991.*
Golay et al., Archives of Biochemistry and Biophysics 526: 146-153, 2012.*
Rossi et al., Blood 113(24): 6161-6171, Jun. 2009.*
Wolf et al., Drug Discovery Today 10(18): 1237-1244, 2005.*
Kontermann et al., Acta Pharmacologica Sinica 26(1): Jan. 1-9, 2005.*

(Continued)

*Primary Examiner* — Phuong Huynh
(74) *Attorney, Agent, or Firm* — Jun He Law Offices P.C.; James J. Zhu

(57) ABSTRACT

Provided herein in certain embodiments are polypeptide complexes capable of binding to an antigen. Pharmaceutical compositions, method of using the polypeptide complexes are also provided.

16 Claims, 12 Drawing Sheets

(56) References Cited

FOREIGN PATENT DOCUMENTS

| EP | 1292621 B1 | 9/2006 |
| WO | WO99/66951 | * 12/1999 |
| WO | 0006605 A2 | 2/2000 |
| WO | 2004076489 A1 | 9/2004 |
| WO | 2005077981 A2 | 8/2005 |
| WO | WO2008112325 | * 9/2005 |
| WO | WO2005118635 | * 12/2005 |
| WO | 2007110205 A2 | 10/2007 |
| WO | 2008012543 A1 | 1/2008 |
| WO | 2008149144 A2 | 12/2008 |

OTHER PUBLICATIONS

LV et al: "Structured to reduce the mitogenicity of anti-CD3 antibody based on computer-guided molecular design", International Journal of Biochemistry and Cell Biology, Pergamon, GB, vol. 39, No. 6, pp. 1142-1155.

Belyanskay et al., "Human agonistic TRAIL receptor antibodies Mapatumumab and Lexatumumab induce apoptosis in malignant mesothelioma and act synergistically with cisplatin" Molecular Cancer. 6: 66-78 (Oct. 2007).

Davis et al., "SEEDbodies: fusion proteins based on strand-exchange engineered domain (SEED) CH3 heterodimers in an Fc analogue platform for asymmetric binders or immunofusions and bispecific antibodies" Protein Engineering, Design & Selection. 23 (4): 195-202 (2010).

Faustman et al., "TNF receptor 2 pathway: drug target for autoimmune diseases" Nature Reviews Drug Discovery. 9: 482-93 (Jun. 2010).

Gunasekaran et al.,"Enhancing antibody Fc heterodimer formation through electrostatic steering effects: applications to bispecific molecules and monovalent IgG" Journal of Biological Chemistry. 285 (25): 19637-46 (Jun. 2010).

Kontermann et al., "A humanized tumor necrosis factor receptor 1 (TNFR1)-specific antagonistic antibody for selective inhibition of tumor necrosis factor (TNF) action" Journal of Immunotherapy. 31 (3): 225-34 (Apr. 2008).

Kontermann, "Strategies to extend plasma half-lives of recombinant antibodies" BioDrugs. 23 (2): 93-109 (2009).

Manero et al., "Stimulation of Fas agonistic antibody—mediated apoptosis by heparin-like agents suppresses Hsp27 but not Bcl-2 protective activity" Cell Stress and Chaperones. 9 (2): 150-66 (Apr. 2004).

Marini et al., "Combination of the pro-apoptotic TRAIL-receptor antibody mapatumumab with ionizing radiation strongly increases long-term tumor control under ambient and hypoxic conditions" International Journal of Radiation Oncology, Biology, Physics. 75 (1): 198-202 (Sep. 2009).

Martens et al., "A Novel One-Armed Anti-c-Met Antibody Inhibits Glioblastoma Growth in vivo" Clinical Cancer Research. 12: 6144-52 (Oct. 2006).

Merchant et al., "An efficient route to human bispecific IgG" Nature Biotechnology. 16: 677-681 (1998).

Muller et al., "Improved pharmacokinetics of recombinant bispecific antibody molecules by fusion to human serum albumin" Journal of Biological Chemistry. 282 (17): 12650-60 (Apr. 2007).

Seo et al., "4-1BB-mediated immunotherapy of rheumatoidarthritis" Nature Medicine. 10 (10): 1088-94 (Oct. 2004).

Stork et al., "A novel tri-functional antibody fusion protein with improved pharmacokinetic properties generated by fusing a bispecific single-chain diabody with an albumin-binding domain from streptococcal protein G" Protein Engineering Design & Selection. 20 (11): 569-76 (Nov. 2007).

Westwood et al., "Three agonist antibodies in combination with high-dose IL-2 eradicate orthotopic kidney cancer in mice" Journal of Translational Medicine. 8: 42-9 (Apr. 2010).

* cited by examiner

Conventional Antibody          DISCObody

CH2CH3 Fab DISCObody

CH3 Fab DISCObody

A: Fc-linker-Fd/LC

Hinge fusion to VHCH1

C: CH3-hinge-Fd/LC

B: Fc-linker-LC/Fd

Hinge fusion to VLCL

D: CH3-linker-LC/Fd

CH2CH3 scFv DISCObody

A: Fc-linker-VH-VL

B: Fc-linker-VL-VH

CH3 scFv DISCObody

C: CH3-hinge-VH-VL

D: CH3-linker-VL-VH

Hinge fusion to VHVL

Hinge fusion to VL-VH

) : a linker (or hinge) sequence

⁼ : Single or double disulfide bonds

X: CH3 or CH2CH3

Y: Fab
-VHCH1-S    or   –VLCL-S
VLCL-S              VHCH1-S scFv
-VH )        or   –VL )
 VL                  VH

C. CH2CH3 Fab DISCObody, hinge fusion to VL-CL

D. CH3 Fab DISCObody, hinge fusion to VL-CL

E. CH2CH3 scFv DISCObody, hinge fusion to VH

F. CH3 scFv DISCObody, hinge fusion to VL (a)

(b)

(c)

(d)

(a)

(b)

PROTEIN COMPLEXES FOR ANTIGEN BINDING AND METHODS OF USE

This application claims the benefit of U.S. Provisional Application Ser. No. 61/411,903, filed on Nov. 9, 2010, which is incorporated herein by reference to its entirety.

FIELD OF THE INVENTION

The present disclosure relates to polypeptide complexes for antigen binding, pharmaceutical compositions thereof, and methods of uses.

BACKGROUND

In recently years, full length monoclonal antibodies have been successfully used to treat cancer, autoimmune and inflammatory diseases and other human diseases. Although there are five different types of immunoglobulins (IgA, IgD, IgG, IgM and IgE) existed in nature, IgG represents the most suitable modality for human therapeutics because of the favorable properties concerning the high binding affinity and specificity, high bioavailability, long serum half life in circulation, potential effector function capability and the industrial-scale manufacturability.

Conventional IgGs are tetramer molecules comprising two identical heavy chains and two identical light chains. IgG heavy chain has a variable domain at the N-terminus followed by the first constant domain (CH1), a hinge and two additional constant domains (CH2CH3). IgG light chain is composed of two domains: an N-terminal variable domain and a C-terminal constant domain. The heavy chain variable region (VH) interacts with the light chain variable region (VL) and the first constant region of heavy chain (CH1) interacts with the light constant (CL) to form the Fab structure. Two CH2CH3 domains form homodimeric Fc structure. So an IgG has two antigen binding Fab arms that are relatively flexible in orientation with each other and with the Fc domain. This structural feature renders IgG the capability of activating certain types of receptors on cell surface due to target dimerization induced by bivalent binding (when both Fab arms bind to antigen). Furthermore, because IgG Fc can bind to cell surface Fc gamma receptors (FcγR), cell surface antigens bound to IgG can be cross-linked to form receptor cluster and thus activated. Conceptually, FcγR can also mediate receptor cross-linking in the event of monovalent antibody/antigen binding. Activation of cell surface receptors by IgG (agonistic antibody) has been successfully demonstrated on a large number of cell surface targets (Seo, Nat. Med. (2004) 10:1088-94, TRAIL receptor (Belyanskay, Mol. Cancer (2007) 6:66-78, Manero, Cell Stress Chaperones (2004) 9:150-66, Westwood, Journal of translational Med. (2010) 8:42-9, Budach, J. Radiat. Oncol. Biol. Physc (2009) 75:198-2002).

While receptor agonist is a useful property of IgG, it is undesirable for some applications. For example, anti-cMet antibody intended to block HGF/cMet signaling in cancer cells actually leads to the activation of this signaling pathway (Martens, Clin. Cancer Res. (2006) 12:6144-52). Anti-TNFR-1 antibodies intended for selectively blocking the TNF ligand signaling through this receptor while sparing TNFR-2 signaling, which is believed to be beneficial to suppressing inflammation, can induce target receptor signaling (Kontermann, J. Immunother. (2008) 31:225-34; Faustman, Nat. Rev. drug discovery (2010) 9:482-493).

A conventional wisdom to avoid the unwanted target cross-linking is to use engineered antibody structures where only one binding unit exists for a given specificity. These antibody structures are commonly referred to as monovalent antibodies. Monovalent antibodies offer significant expansion of the toolbox for treating human diseases.

A straightforward and efficient engineering strategy for monovalent antibodies is to use single variable domain, single chain Fv (scFv) or Fab fragment. An anti-TNFR-1 domain antibody and Fab fragments were engineered to selectively block TNF signaling through TNFR-1 (sparing the signaling through TNFR-2) (Kontermann, J. Immunother. (2008)31(3):225-34; US20080008713; WO2008149144; US20100150916). The major drawback for these antibody fragments for systemic therapeutic application is the short half life because of their small size (below kidney filtration threshold of ~60 kD). To make these antibody fragments practically useful therapeutics for chronic diseases, half-life extension strategies are needed (Kontermann, BioDrugs (2009) 23:93-109). The strategies include pegylation (US24121415), fusion with albumin (Muller, J. Biol. Chem. (2007) 282:12650-60) or fusion with albumin binder (Stork, Prot. Eng. Des. Sel. (2007) 20:569-76).

Fusion with monomeric Fc (CH3 interface engineered to disrupt CH3-CH3 association, US 2009/022642) or single chain Fc (scFc) (in sequence configuration of N-terminus-hinge-CH2-CH3-linker-hinge-CH2-CH3-C-terminus provides a potential solution to generating monovalent antibodies) is another potential solution for generating monovalent antibodies with improved half life (WO2005077981, WO/2008/012543, US20090304696, US20090252729).

Additional engineering approaches focusing on the CH3-CH3 interface residues have been undertaken to make monovalent antibodies. CH3 interface engineering creating a "knob" in one and a "hole" in the other CH3 led to the formation of heterodimeric Fc molecule (knob-in-hole, U.S. Pat. No. 5,821,333, Merchant et al., Nat Biotech. (1998)16:677-681). Asymmetrical fusion of antibody V domain-containing fragments to the mutant CH2CH3 chain can lead to various monovalent antibody molecules. Based on this technology, one-arm antibody, OA5D5, specific to cMet has been generated (U.S. Pat. No. 5,821,333, US2008/0063461). Rigorous preclinical tests strongly suggest that, unlike the bivalent antibody counterpart, this monovalent antibody is a pure cMet antagonist (without agonistic activity). This monovalent antibody is currently being tested in multiple anti cancer clinical trials. A similar heterodimeric Fc engineering strategy based on amino acid substitutions in CH3-CH3 interface was used to create an anti-TNFR-1 monovalent antibody (WO2008089004, Gunasekaran et al., J.B.C. (2010) 285:19637-19646). Efficient Fc heterodimer formation was also devised based on strand-exchange engineered domain (SEED) design (Davis et al., PEDS 2010, 23:195-202, US20070287170).

It is noted that the success of the above mentioned monovalent antibodies reflects the real demand, significant investment effort and therefore scientific advancement. However, generation of these molecules involves either chemical modification or amino acid substitutions at conserved positions which often decrease protein stability. Destabilized proteins as therapeutics may raise concerns over product manufacturability and clinical safety (such as immunogenicity). Therefore, there remains a need for new antibody modalities which will not activate target receptors upon binding and in the meantime offer improved profiles on product stability, safety and manufacturability.

SUMMARY OF THE INVENTION

In one aspect, the present disclosure provides a polypeptide complex comprising a first polypeptide which comprises a first protein monomer and a first antigen-binding domain, and a second polypeptide which comprises a second protein monomer and a second antigen-binding domain, wherein the first protein monomer forms a dimer with the second protein monomer; wherein the C-terminal of the first protein monomer is operably linked to the N-terminal of the first antigen-binding domain; and wherein the C-terminal of the second protein monomer is operably linked to the N-terminal of the second antigen-binding domain.

In certain embodiments, the formation of the dimer in the polypeptide complex substantially reduces the simultaneous binding of the first antigen-binding domain and the second antigen-binding domain to an antigen. In certain embodiment, the formation of the dimer renders a steric hindrance such that when the first antigen-biding domain binds to the target, the second antigen-binding domain is substantially prevented from binding to the same target, as a result, the effect (e.g., signaling) caused by simultaneous binding of the first and second antigen binding domains is substantially reduced.

In certain embodiments, the first polypeptide further comprises a first thiol residue-containing peptide linker, the second polypeptide further comprises a second thiol residue-containing peptide linker; the N-terminal of the first peptide linker is covalently linked to the C-terminal of the first protein monomer; the C-terminal of the first peptide linker is covalently linked to the N-terminal of the first antigen-binding domain; the N-terminal of the second peptide linker is covalently linked to the C-terminal of the second protein monomer; the C-terminal of the second peptide linker is covalently linked to the N-terminal of the second antigen-binding domain; and the first peptide linker and the second peptide linker forms a disulfide bond. In certain embodiments, the thiol residue is cysteine.

In certain embodiments, the disulfide bond substantially reduces the simultaneous binding of the first antigen-binding domain and the second antigen-binding domain to an antigen.

In certain embodiments, the first thiol residue or the second thiol residue is 1-10 amino acid residues away from the C-terminal of the peptide linker.

In certain embodiments, the first protein monomer is the same or not the same of the second protein monomer. In certain embodiments, the first antigen-binding domain is the same or not the same of the second antigen-binding domain. In certain embodiments, the first antigen-binding domain binds to the same or not the same target as the second-binding domain.

In certain embodiments, the first antigen-binding domain and/or the second binding domain comprise a CH3 domain from an immunoglobulin and C-terminal of the CH3 domain is operably linked to the N-terminal of the first antigen-binding domain or the second antigen-binding domain.

In certain embodiments, the first antigen-binding domain and/or the second binding domain further comprise a CH2 domain from the immunoglobulin and the C-terminal of the CH2 domain is covalently linked to the N-terminal of the CH3 domain.

In certain embodiments, the immunoglobulin is selected from the group consisting of Ig A, Ig D, Ig E, Ig G, and Ig M.

In certain embodiments, the first antigen-binding domain or the second binding domain is selected from the group consisting of a CDR, a Fv, a VL, a VH, a light chain, and a heavy chain, a ScFv, a Fab, camelid VHH, dAb, Fibronectin 3 domain (Fn3), an ankryin repeat, and an Adnectin.

In certain embodiments, one or more additional antigen-binding domains are operably linked to the N-terminal of the first protein monomer, the N-terminal of the second protein monomer, the C-terminal of the first antigen-binding domain, or the C-terminal of the second antigen-binding domain.

In certain embodiments, the first antigen-binding domain or the second antigen-binding domain is a first light chain fragment which is disulfidely bonded to a first heavy chain fragment. In certain embodiments, one or more additional antigen-binding domains are operably linked to the C-terminal of the first light chain fragment, the C-terminal of the first heavy chain fragment, or the N-terminal of the first heavy chain fragment.

In certain embodiments, the first antigen-binding domain or the second antigen-binding domain is a second heavy chain fragment which is disulfidely bonded to a second light chain fragment. In certain embodiments, one or more additional antigen-binding domains are operably linked to the C-terminal of the second light chain fragment, the C-terminal of the second heavy chain fragment, or the N-terminal of the second light chain fragment.

In another aspect, the present disclosure provides a polypeptide comprising a protein monomer and an antigen-binding domain, wherein the C-terminal of the protein monomer is operably linked to the N-terminal of the antigen-binding domain, wherein the protein monomer is capable of forming a homogenous dimer. In certain embodiments, the polypeptide further comprises a thiol residue-containing peptide linker, wherein the N-terminal of the peptide linker is covalently linked to the C-terminal of the protein monomer; the C-terminal of the peptide linker is covalently linked to the N-terminal of the antigen-binding domain.

In certain embodiments, present disclosure provides a polynucleotide encoding the polypeptide. In certain embodiments, the present disclosure provides a vector comprising the polynucleotide provided herein. In certain embodiments, the present disclosure provides a vector comprising a first polynucleotide encoding the first polypeptide disclosed herein and a second polynucleotide encoding the second polypeptide disclosed herein. In certain embodiments, the present disclosure provides a host cell containing the vector provided herein. In certain embodiments, the present disclosure provides a host cell comprising a first vector comprising the first polynucleotide and a second vector comprising the second polynucleotide. In certain embodiments, the present disclosure provides a host cell comprising the first polynucleotide and the second polynucleotide. In certain embodiments, the present disclosure provides a host cell comprising a polypeptide complex disclosed herein. In certain embodiments, the polypeptide complex or the polypeptide is secreted from the host into a surrounding medium or environment.

In certain embodiments, the present disclosure provides a method of expressing the polypeptide or the polypeptide complex, comprising culturing the host cell provided herein under the condition that is suitable for expression of the vector provided herein. The method further comprises a step of purifying or isolating the polypeptide or polypeptide complex.

In certain embodiments, the present disclosure provides a pharmaceutical composition comprising the polypeptide complex provided herein and a pharmaceutical carrier.

In certain embodiments, the present disclosure provides a method of treating or preventing a condition, comprising administering an effective amount of the pharmaceutical composition provided herein to a subject in need, wherein the condition is associated with an antigen to which the polypeptide complex can bind.

In certain embodiments, the present disclosure provides a method of detecting the presence of an antigen in a sample, comprising contacting the sample with the polypeptide complex, and determining the presence of the antigen.

BRIEF DESCRIPTION OF FIGURES

FIG. 8: Embodiments of the polypeptide complexes and schematic primary sequence diagrams for the embodied polypeptide complexes. In FIGS. 8B and 8C, the protein monomers are CH2CH3 domain and CH3 domain, respectively, and the antigen-binding domains are Fab domains, in which the C-terminal of the CH2CH3 domain or the CH3 domain is covalently linked to the N-terminal of a hinge sequence and the C-terminal of the hinge sequence is covalently linked to the C terminal of the heavy chain of the Fab domain, and the two hinge sequences form two inter-chain disulfide bonds. In FIGS. 8D and 8E, the protein monomers are CH2CH3 domain and CH3 domain, respectively, and the antigen-binding domains are Fab domains, in which the C-terminal of the CH2CH3 domain or CH3 domain is covalently linked to the N-terminal of a hinge sequence and the C-terminal of the hinge sequence is covalently linked to the C terminal of the light chain of the Fab domain, and the two hinge sequences form two inter-chain disulfide bonds. In FIG. 8F, the protein monomers are CH2CH3 domain, and the antigen-binding domains are scFv domain, in which the C-terminal of the CH2CH3 domain is covalently linked to the N-terminal of a hinge sequence and the C-terminal of the hinge sequence is covalently linked to the C terminal of the heavy chain of the scFv domain, and the two hinge sequences form two inter-chain disulfide bonds. In FIG. 8G, the protein monomers are CH3 domain, and the antigen-binding domains are scFv domain, in which the C-terminal of the CH3 domain is covalently linked to the N-terminal of a hinge sequence and the C-terminal of the hinge sequence is covalently linked to the C terminal of the light chain of the scFv domain, and the two hinge sequences form two inter-chain disulfide bonds.

DETAILED DESCRIPTION

The following description is merely intended to illustrate various embodiments of the present disclosure. As such, the specific modifications discussed are not intended to be limiting. It will be apparent to one skilled in the art that various equivalents, changes, and modifications may be made without departing from the spirit or scope of the subject matters presented herein, and it is understood that such equivalent embodiments are to be included herein.

All references cited herein, including publications, patents and patent applications are incorporated herein by reference in their entirety.

Conventional antibodies are composed of immunoglobulins. Immunoglobulins share a four-chain basic structure composed of two identical heavy chains and two identical light chains. Immunoglobulins are grouped into five classes, namely immunoglobulin (Ig) A, Ig D, Ig E, Ig G, and Ig M, each with a distinct type of heavy chains α, δ, ε, γ, and μ, respectively. Among them, IgG can be further classified into four subclasses, namely IgG1, IgG2, IgG3, and IgG4, and IgA can be further classified into two subclasses, namely IgA1 and IgA2, based on their heavy chain characteristics. Mammalian light chains are classified as λ or κ light chains.

Each heavy chain of an immunoglobulin consists of a variable region (VH domain) and several constant regions (CH domains). In IgA, Ig D, and Ig G, each heavy chain comprises three constant regions, namely CH1 domain, CH2 domain and CH3 domain, and a hinge region between the CH1 and CH2 domain. In IgM and IgE, each heavy chain comprises four constant regions, namely the first constant region, second constant region, third constant region and fourth constant region, in which the second constant region largely plays the role of the hinge region of IgA, Ig D, and Ig G. For better illustration, "CH2 domain" as used herein is intended to mean the second constant region of IgA, Ig D, and Ig G, and the third constant region of IgM and IgE; "CH3 domain" as used herein is intended to mean the third constant region of IgA, Ig D, and Ig G, and the fourth constant region of IgM and IgE; and "hinge" region as used herein is intended to mean the hinge region of IgA, Ig D, and Ig G, and the second constant region of IgM and IgE. Each light chain of an immunoglobulin consists of a variable region (VL domain) and a constant region (CL domain).

Figure 1:
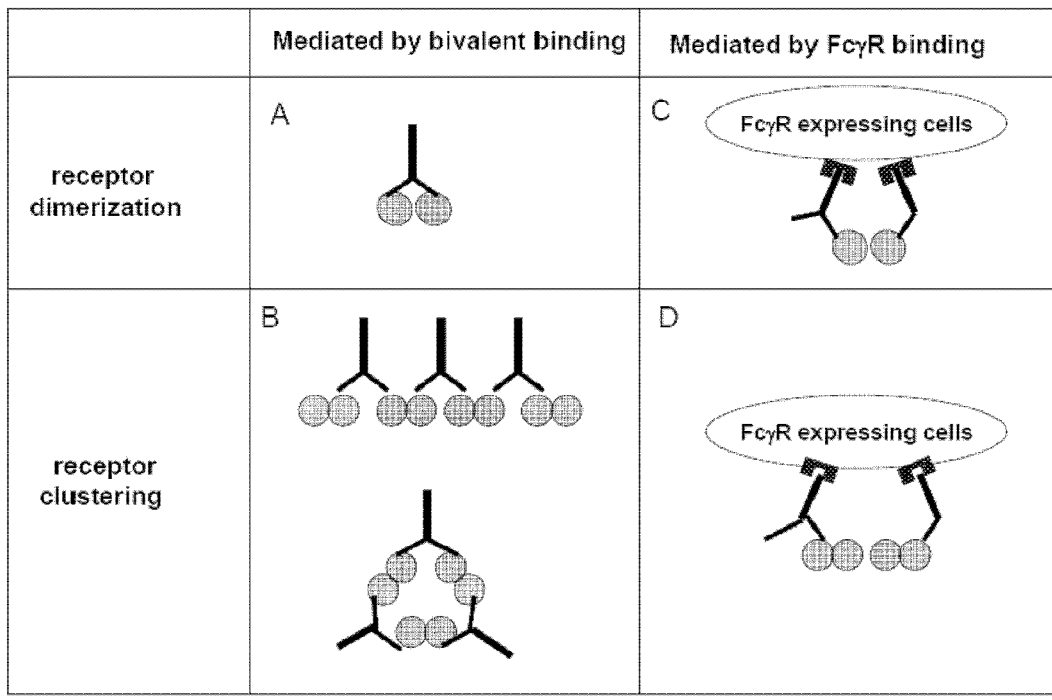
FIG. 1: Schematic diagram describing receptor dimerization or cross-linking mediated by antibody binding and FcγR binding to antibody/antigen complex. A: bivalent IgG binding of antigen dimerizes target molecules; B: receptor cross-linking (clustering) mediated by bivalent antibody/antigen binding. TNF receptors or superfamily member receptors on cell surface are likely associated as non-signaling dimmers. Bivalent antibody/antigen binding can cause receptor cross-linking to form signaling cluster. C: monovalently bound antigens can be dimerized by FcγR binding of the antibody/antigen complex; D, monovalently bound antigens form receptor cluster through FcγR binding of the antibody antigen complex.
Figure 2:
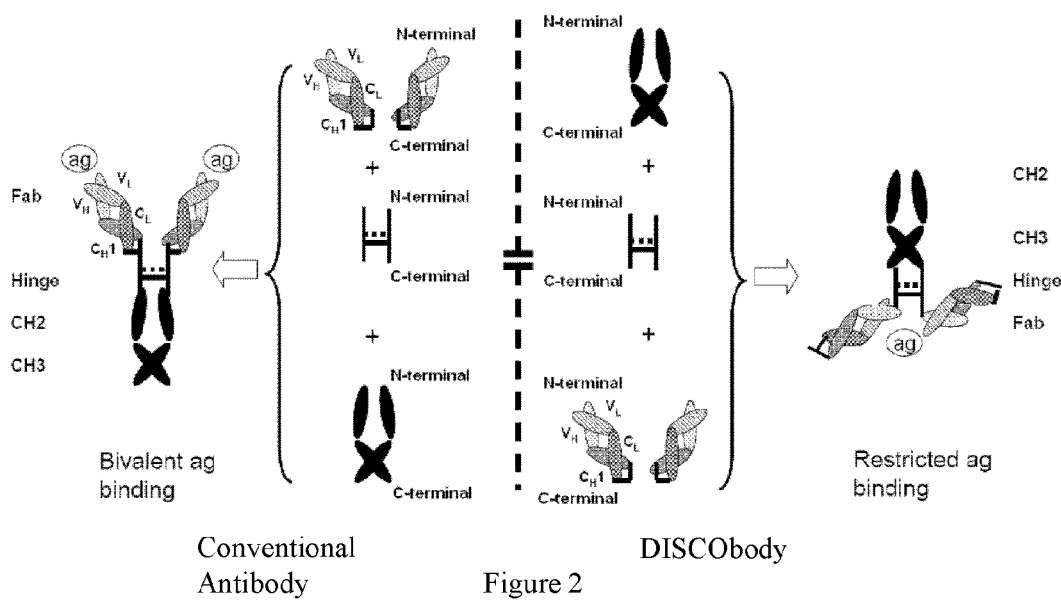
FIG. 2: Comparison of conventional antibody configuration (left panel) and DISCObody basic configuration (right panel). In DISCObody (right panel), CH2CH3 and a C-terminus flexible linker (or hinge) sequence containing cysteine residue(s) is fused to the N-terminus of a Fab structure. CH2CH3 dimerization facilitates the hinge cysteine residue(s) to form interchain disulfide bonds. The formation of the disulfide bond tethers the antigen binding regions of the two Fabs that are close in space and restricts the freedom of the orientation of antigen binding regions. Consequently, the apparent antigen binding becomes monovalent or in case both antigen binding regions can simultaneously bind to antigen targets, the resultant target orientation can be locked into a non activating conformation.

In an immunoglobulin, the N-terminal of the heavy chain starts from the N-terminal of the VH domain, whose C-terminal is covalently linked to the N-terminal of the CH1 domain. The C-terminal of the CH1 domain is then covalently linked to the N-terminal of the hinge region, followed by the N terminal of the CH2 domain linked to the C-terminal of the hinge region and the N terminal of the CH3 domain linked to the C-terminal of the CH2 domain (see FIG. 2, left panel). The two heavy chains form a "Y" shape. Each arm of the Y is composed of one VH domain and one CH1 domain, and the stem is composed of two hinge regions, two CH2 domains and two CH3 domains, in which the two CH3 domains forms a dimer through non-covalent interactions. The hinge regions contain cysteines and are capable of forming disulfide bridges between the two heavy chains.

By the same token, the N terminal of the light chain starts from the N-terminal of the VL domain, whose C-terminal is covalently linked to the N-terminal of the CL domain. Each light chain is paired with each heavy chain at the arm of the Y, with the VL domain associated with the VH domain and the CL domain associated with the CH1 domain, and such association is stabilized by an inter-chain disulfide bond between the CL domain and the CH1 domain.

The VL domain and the VH domain, located at the N-terminals of the two arms of the Y, are responsible for antigen recognition and binding. The CH2 and the CH3 domains, located at the C-terminals of the stem of the Y, are responsible for interacting with effector molecules such as Fc receptor and complement C1q, which interaction triggers immune responses against the antigen which is bound to the VL and VH domain.

One aspect of the present disclosure provides polypeptide complexes comprising a first polypeptide which comprises a first protein monomer and a first antigen-binding domain, and a second polypeptide which comprises a second protein monomer and a second antigen-binding domain, wherein the first protein monomer forms a dimer with the second protein monomer; wherein the C-terminal of the first protein monomer is operably linked to the N-terminal of the first antigen-binding domain; and wherein the C-terminal of the second protein monomer is operably linked to the N-terminal of the second antigen-binding domain.

The term "protein monomer" as used herein refers to a protein fragment that is capable of forming a dimer with another protein fragment.

The term "antigen-binding domain" as used herein refers to a protein domain that can specifically bind to an antigen target.

The term "antigen target" or "antigen" or "target" as used herein refers to a biological molecule or a moiety thereof. Examples of antigen targets include, without limitation, a protein, a peptide, a polynucleotide, a lipid molecule, a sugar molecule, a hormone, a neurotransmitter, a compound, or a complex containing a combination thereof.

The term "specifically bind" as used herein refers to a non-random association between two molecules. In certain embodiments, the antigen-binding domain specifically binds to the antigen target with a binding affinity (Kd) of $\leq 10^{-6}$M. For example, the antigen-binding domain may bind to the antigen target with a Kd of $\leq 5\times 10^{-7}$M, $\leq 10^{-7}$M, $\leq 5\times 10^{-8}$M, $\leq 10^{-8}$M, $\leq 5\times 10^{-9}$M, $\leq 10^{-9}$M, $\leq 5\times 10^{-10}$M, or $\leq 10^{-10}$M. Kd as used herein refers to the ratio of the dissociation rate to the association rate ($k_{off}/k_{on}$), and may be determined using any suitable methods known in the art, such as for example, Biacore (Malmqvist M., Biochem. Soc. Trans., 27(2): 335-340 (1999)) or Kinexa techniques (Darling, R. J., et al, Assay Drug Dev. Technol., 2(6): 647-657 (2004)).

In the polypeptide complexes, the C-terminal of the first protein monomer is operably linked to the N-terminal of the first antigen-binding domain, and the C-terminal of the second protein monomer is operably linked to the N-terminal of the second antigen-binding domain.

"C-terminal" of a polypeptide as used herein refers to the last amino acid residue of the polypeptide which donates its amine group to form a peptide bond with the carboxyl group of its adjacent amino acid residue. "N-terminal" of a polypeptide as used herein refers to the first amino acid of the polypeptide which donates its carboxyl group to form a peptide bond with the amine group of its adjacent amino acid residue.

The term "operably link" as used herein refers to direct linking through one or more chemical bonds or indirect linking through one or more linkers.

Any suitable chemical bonds can be used to make a direct link, including without limitation, covalent bonds such as peptide bond and disulfide bond, non-covalent bonds such as hydrogen bond, hydrophobic bond, ionic bond, and Van der Waals bond.

A "covalent bond" refers herein to a stable association between two atoms which share one or more electrons. Examples of the covalent bonds include, without limitation, a peptide bond and a disulfide bond. "Peptide bond" as used herein refers to the covalent bond formed between the carboxyl group of an amino acid and the amine group of the adjacent amino acid. "Disulfide bond" as used herein refers to a covalent bond formed between two sulfur atoms. A disulfide bond can be formed from oxidation of two thiol groups. In certain embodiments, the operably link is direct link through a covalent bond. In certain embodiments, the operably link is direct link through a peptide bond or a disulfide bond.

A "non-covalent bond" refers herein to an attractive interaction between two molecules or two chemical groups that does not involve sharing of electrons. Examples of non-covalent bonds include, without limitation, a hydrogen bond, a hydrophobic bond, an ionic bond, and a Van der Waals bond. A "hydrogen bond" refers herein to attractive force between a hydrogen atom of a first molecule/group and an electronegative atom of a second molecule/group. A "hydrophobic bond" refers herein to a force that causes hydrophobic or non-polar molecules/groups to aggregate or associate together in an aqueous environment. An "ionic bond" refers herein to an attraction between a positive ion and a negative ion. A "Van der Waals bond" refers herein to a non-specific attraction force between two adjacent molecules/groups which have momentary random fluctuations in the distribution of electrons. In certain embodiments, the operably link is direct link through a non-covalent bond. In certain embodiments, the operably link is direct link through a hydrogen bond, a hydrophobic bond, an ionic bond, or a Van der Waals bond.

Any suitable linkers can be used to make an indirect link, such as without limitation, peptide linker, polymer linker, and chemical linker. In certain embodiments, the operably link is an indirect link through a peptide linker.

In certain embodiments, the C-terminal of the first protein monomer is directly linked to the N-terminal of the first antigen-binding domain by one or more chemical bonds. In certain embodiments, the C-terminal of the second protein monomer is directly linked to the N-terminal of the second antigen-binding domain by one or more chemical bonds.

In certain embodiments, the first polypeptide further comprises a first linker, and one end of the first linker is covalently linked to the C-terminal of the first protein monomer, and the other end of the first linker is covalently linked to the N-terminal of the first antigen-binding domain. In certain embodiments, the second polypeptide further comprises a second linker, and one end of the second linker is covalently linked to the C-terminal of the second protein monomer, and the other end of the second linker is covalently linked to the N-terminal of the second antigen-binding domain.

Figure 8A:
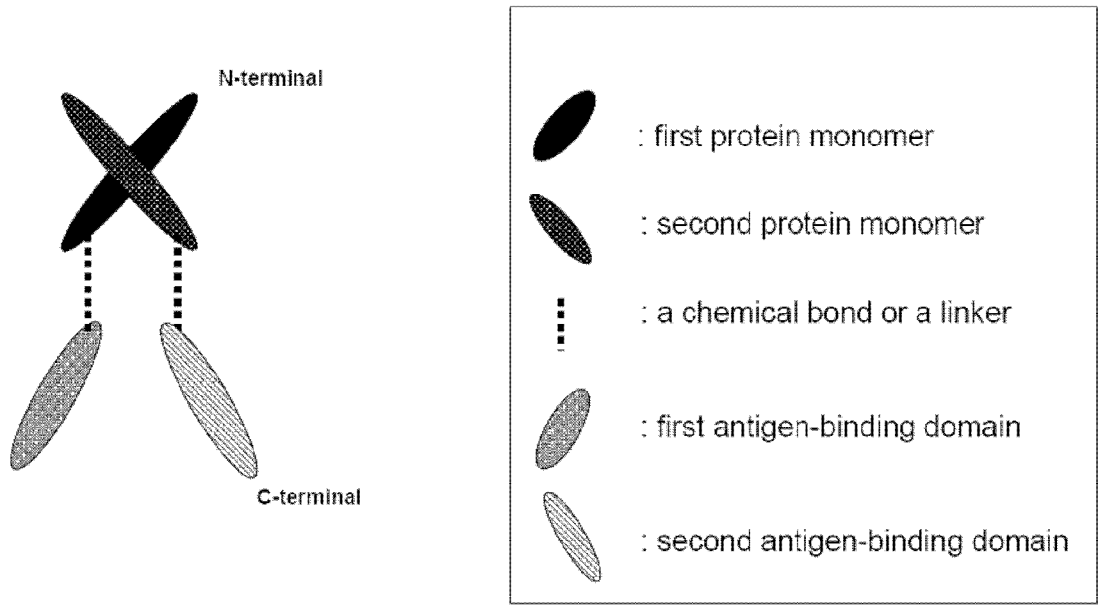
FIG. 8A shows an embodiment of the polypeptide complexes, in which the first protein monomer forms a dimer with the second protein monomer.
Figure 8B:
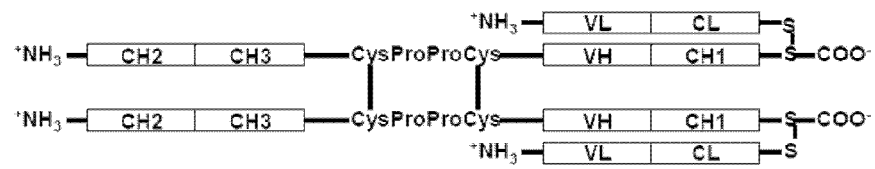
FIG. 8B-8G show the schematic diagrams for primary amino acid sequences of different embodiments of the polypeptide complexes.
Figure 8C:
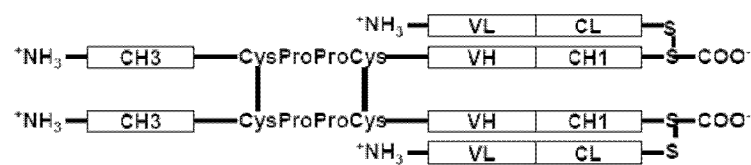
Figure 8D:
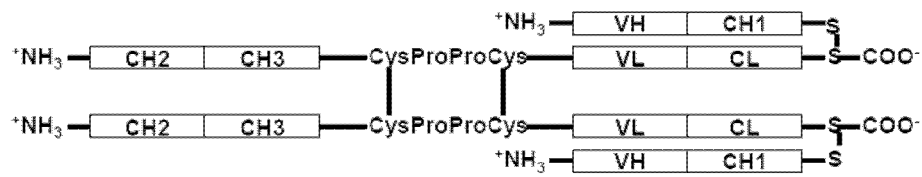
Figure 8E:
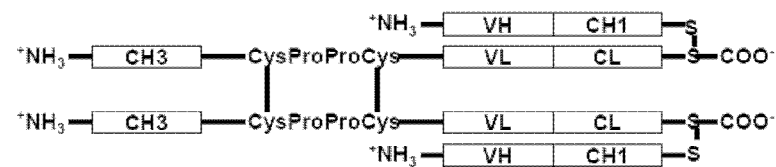
Figure 8F:
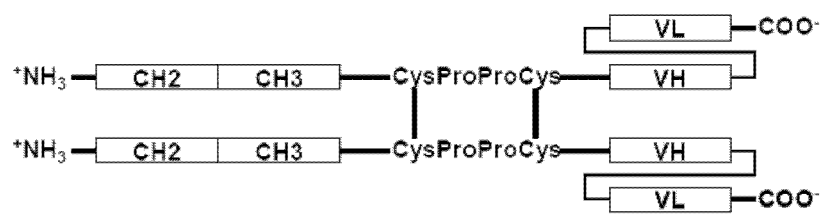
Figure 8G:
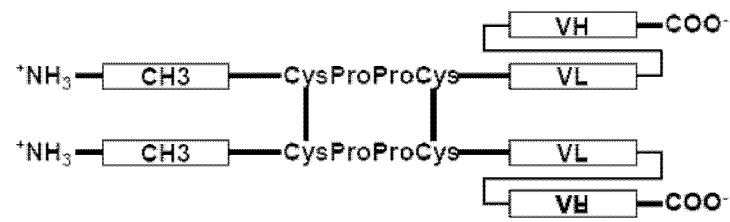

In the polypeptide complexes, the first protein monomer forms a dimer with the second protein monomer. The dimer can be formed through one or more chemical bonds or one or more linkers. An exemplary structure for the protein complex is shown in FIG. 8A.

In certain embodiments, the first protein monomer forms a dimer with the second protein monomer through one or more chemical bonds. The chemical bonds can comprise a covalent bond or a non-covalent bond. The covalent bond may comprise a disulfide bond. The non-covalent bond may comprise a hydrogen bond, a hydrophobic bond, an ionic bond, and/or a Van der Waals bond.

In certain embodiments, the first protein monomer forms a dimer with the second protein monomer through one or more linkers. Any linker that is suitable for linking two molecules may be used, including, without limitation, a peptide linker, a polymer linker, and a chemical linker. In certain embodiments, the one or more linkers comprise a peptide linker.

Antigen-Binding Domain

In certain embodiments, the first antigen-binding domain and/or the second antigen binding domain comprises an antibody-derived component or can be non-antibody component. An antibody-derived component can comprise a fragment of an antibody or a genetically engineered product of one or more fragments of the antibody, which fragment involves in binding with an antigen. Examples of the antibody-derived component include, without limitation, a complementarity determining region (CDR), a variable domain (Fv), a heavy chain variable region (VH), a light chain variable region (VL), a heavy chain, a light chain, a single chain variable region (scFv), a Fab, a single domain camel antibody (camelid VHH), and single domain antibodies (dAb).

"Complementarity determining region" or "CDR" with regard to an antibody refers to a highly variable loop in the variable region of the heavy chain or the light chain of an antibody. CDRs can complement with the antigen conformation and determine the binding to the antigen. The heavy chain variable region and the light chain variable region each contain 3 CDRs. The CDRs can be defined or identified by conventional methods, such as by sequence according to Kabat et al (Wu, T T and Kabat, E. A., J Exp Med. 132(2):211-50, (1970); Borden, P. and Kabat E. A., PNAS, 84: 2440-2443 (1987); Kabat, E. A. et al, Sequences of proteins of immunological interest, Published by DIANE Publishing, 1992), or by structure according to Chothia et al (Choithia, C. and Lesk, A. M., J Mol. Biol., 196(4): 901-917 (1987), Choithia, C. et al, Nature, 342: 877-883 (1989)).

"Heavy chain variable region" or "VH" with regard to an antibody refers to the fragment of the heavy chain that contains three CDRs interposed between flanking stretches known as framework regions, which are more highly conserved than the CDRs and form a scaffold to support the CDRs.

"Light chain variable region" or "VL" with regard to an antibody refers to the fragment of the light chain that contains three CDRs interposed between framework regions.

"Fv" with regard to an antibody refers to the smallest fragment of the antibody to bear the complete antigen binding site. An Fv fragment consists of the variable region of a single light chain bound to the variable region of a single heavy chain.

"Single-chain Fv antibody" or "scFv" with regard to an antibody refers to an engineered antibody consisting of a light chain variable region and a heavy chain variable region connected to one another directly or via a peptide linker sequence.

"Fab" with regard to an antibody refers to that portion of the antibody consisting of a single light chain (both variable and constant regions) bound to the variable region and first constant region of a single heavy chain by a disulfide bond.

"Single domain camel antibody" or "camelid VHH" as used herein refers to the smallest known antigen-binding unit of a heavy chain antibody (Koch-Nolte, et al, FASEB J., 21: 3490-3498 (2007)). A "heavy chain antibody" or a "camelid antibody" refers to an antibody that contains two VH domains and no light chains (Riechmann L. et al, J.

Immunol. Methods 231:25-38 (1999); WO94/04678; WO94/25591; U.S. Pat. No. 6,005,079).

"Single domain antibody" or "dAb" refers to an antibody fragment that consists of the variable domain of an antibody heavy chain ($V_H$ domain) or the variable domain of an antibody light chain ($V_L$ domain) (Holt, L., et al, Trends in Biotechnology, 21(11): 484-490).

In certain embodiments, the first antigen-binding domain or the second antigen-binding domain is selected from the group consisting of a CDR, a Fv, a VH, a VL, a heavy chain, a light chain, a scFv, a Fab, a camelid VHH, and a dAb. In certain embodiments, the first antigen-binding domain and the second antigen-binding domain are both scFv or both Fab.

In certain embodiments, the first antigen-binding domain or the second antigen-binding domain is an antibody-derived component of an anti-CD3 antibody, an anti-EpCAM antibody, an anti-IL6 antibody, an anti-CD19 antibody, an anti-TNFR antibody, or an anti-PSCK antibody. The antibody-derived component can be a Fab fragment or a scFv fragment for these antibodies.

Figure 3:
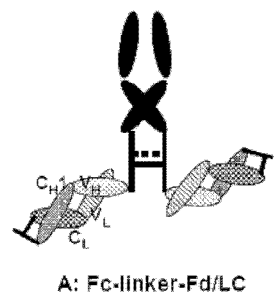
FIG. 3: Fab DISCObody. Target binding fragment is Fab. CH2CH3-hinge is fused to: A, VH of a Fab; B, VL of a Fab; CH3-hinge is fused to: C, VH of a Fab; D, VL of a Fab.
Figure 3:
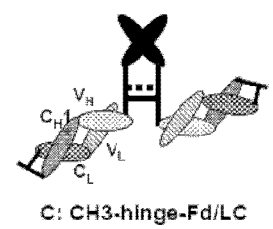
Figure 3:
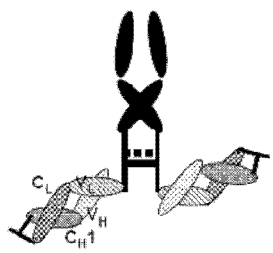
Figure 3:
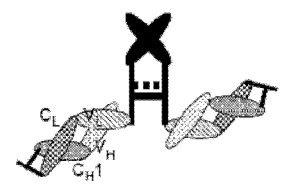

In certain embodiments, the first antigen-binding domain or the second antigen-binding domain comprises a first light chain fragment which is disulfidely bonded to a first heavy chain fragment. For example, the C-terminal of the first protein monomer is operably linked to the N-terminal of the first light chain fragment, which is disulfidely bonded to the first heavy chain fragment (see, e.g. FIGS. 3 B and D). In certain embodiments, the first antigen-binding domain or the second antigen-binding domain comprises a second heavy chain fragment which is disulfidely bonded to a second light chain fragment. For example, the C-terminal of the first protein monomer is operably linked to the N-terminal of the second heavy chain fragment, which is disulfidely bonded to the second light chain fragment (see, e.g. FIGS. 3 A and C).

The term "disulfidely bonded" as used herein refers to the binding of a heavy chain fragment to a light chain fragment through one or more inter-chain disulfide bonds. The one or more disulfide bonds can be formed between the two fragments by linking the thiol groups in the two fragments. In certain embodiments, the one or more disulfide bonds can be formed between one or more cysteine residues in the heavy chain fragment and the light chain fragment, respectively.

Figure 4:
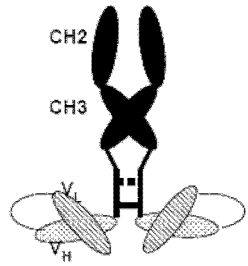
FIG. 4: scFv DISCObody. Target binding fragment is scFv. CH2CH3-hinge is fused to: A, VH of a scFv; B, VL of a scFv; CH3-hinge is fused to: C, VH of a scFv; D, VL of a scFv.
Figure 4:
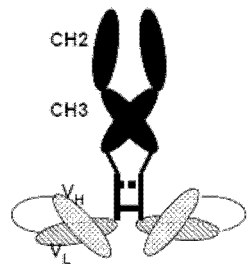
Figure 4:
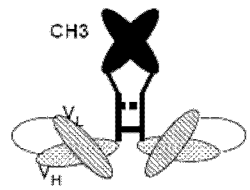
Figure 4:
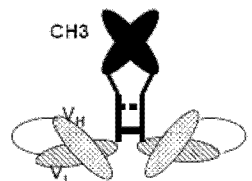

In certain embodiments, the first antigen-binding domain or the second antigen-binding domain comprises a scFv fragment whose light chain or heavy chain is operably linked to the respective protein monomer. Exemplary structures of the protein complexes are shown in FIG. 4 a-d.

In certain embodiments, the first antigen-binding domain and/or the second antigen binding domain comprises a non-antibody component. The non-antibody component which binds to an antigen can be any suitable protein domains or components that can recognize and bind to an antigen, such as for example, protein domains that involve in protein-protein interactions, in protein-lipid interactions, in protein-polynucleotide interactions, in protein-sugar interactions, or in ligand binding. Examples of suitable non-antibody component include, without limitation, Fibronectin 3 domain (Fn3), an ankryin repeat, and an Adnectin.

"Fibronectin 3 domain" or "Fn3" as used herein refers to an autonomous folding unit in fibronectin which is involved in binding to biological molecules (Calaycay, J. et al, J. Biol. Chem., 260(22): 12136-41 (1985); Koide, A. et al, J. Mol. Biol., 284(4): 1141-1151 (1998); Bloom, L. et al, Drug Discovery Today, 14(19-20): 949-955 (2009)). The Fn3 domain can be found in a variety of proteins and different repeats of Fn3 domain are found to contain binding sites for biological molecules such as DNA and proteins.

"Ankyrin repeat" as used herein refers to a protein component containing repeats of a 33-amino acid residue found in erythrocyte ankyrin (Davis, L. H. et al, J. Biol. Chem., 266(17): 11163-11169 (1991)). Ankyrin repeat is known as one of the most common protein-protein interaction structure that occurs in a large number of proteins with different functions.

"Adnectin" as used herein refers to a genetically engineered protein that is based on a Fn3 domain (Koide, A. et al, Methods Mol. Biol., 352: 95-109 (2007)). The Fn3 domain in Adnectin contains three loops that mimics the three CDRs of the variable region of an antibody, and can be genetically tailored for specific binding to different target molecules.

In certain embodiments, the first antigen-binding domain is the same of the second antigen-binding domain. The first antigen-binding domain is the same of the second antigen-binding domain in the sense that they share at least one similarity, for example without limitation, they are both antibody-derived, they are both non-antibody component, they both comprise scFv, they both comprise Fab, they both bind to the same antigen target, or they share the same amino acid sequence. In certain embodiments, the first antigen-binding domain is not the same of the second antigen-binding domain.

In certain embodiments, the first antigen-binding domain binds to the same target as the second-binding domain. The first antigen-binding domain binds to the same target as the second antigen-binding domain in the sense that the targets share at least one similarity, for example without limitation, the targets comprise both protein, polynucleotide, or lipid, the targets are the same protein though may be different isoforms, the targets have the same chemical structures though may be different stereoisomers, or the targets have the same amino acid sequences. In certain embodiments, the first antigen-binding domain binds to not the same target as the second-binding domain.

In certain embodiments, the first antigen-binding domain and/or the second antigen-binding domain can have cross-reactivity to more than one antigen targets. "Cross-reactivity" as used herein refers to that an antigen-binding domain can specifically bind to more than one antigen targets. In certain embodiments, the first antigen-binding domain and/or the second antigen-binding domain can have cross-reactivity to completely different antigen targets, such as for example, hepatitis C core protein and host-derived GOR protein. In certain embodiments, the first antigen-binding domain and/or the second antigen-binding domain can have cross-reactivity to an antigen target from different species, such as for example, human CD3 and monkey CD3.

Protein Monomer

In certain embodiments, the first protein monomer and/or the second protein monomer comprises an antibody-derived monomer or a non-antibody monomer.

An antibody-derived monomer can be a fragment of an antibody or a genetically engineered product of one or more fragments of the antibody, which fragment can dimerize with another fragment. Examples of the antibody-derived monomer include, without limitation, a CH3 domain from an immunoglobulin. In certain embodiments, the CH3 domain is from an immunoglobin selected from the group consisting of Ig A, Ig D, Ig E, Ig G, and Ig M.

In certain embodiments, the first protein monomer and/or the second protein monomer comprises a CH3 domain from an immunoglobin. In certain embodiments, the first protein monomer and/or the second protein monomer further comprises a CH2 domain from an immunoglobin. In certain embodiments, the C terminal of the CH2 domain is covalently linked to the N-terminal of CH3 domain. In certain embodiments, the CH2 domain is from an immunoglobin selected from the group consisting of Ig A, Ig D, Ig E, Ig G, and Ig M.

A non-antibody monomer can be a non-antibody protein fragment that can dimerize with another protein fragment. Such dimerization can be mediated by covalent bonds such as disulfide bond or non-covalent interactions such as a hydrogen bond, a hydrophobic bond, an ionic bond, and a Van der Waals bond.

In certain embodiments, the first protein monomer is the same of the second protein monomer. In certain embodiments, the first protein monomer is not the same of the second protein monomer.

In certain embodiments, the first protein monomer and the second protein monomer form a dimer, and formation of the dimer in the polypeptide complex substantially reduces the simultaneous binding of the first antigen-binding domain and the second antigen-binding domain to an antigen.

The term "substantially reduce" refers to at least 10% reduction in the simultaneous binding of the first antigen-binding domain and the second antigen-binding domain, as compared to the simultaneous binding when the first polypeptide and the second polypeptide are not associated.

In certain embodiments, the simultaneous binding is reduced by at least 10% as compared to the simultaneous binding when the first antigen-binding domain and the second antigen-binding domain are present on a conventional antibody structure. For example, as compared to a conventional anti-CD3 antibody having two identical Fab fragments, a protein complex provided herein comprising such Fab fragments can have at least 10% reduction in simultaneous binding of the two Fabs by the CD3 antigen. For another example, a conventional IgG may be modified to include two scFv fragments in replacement of the natural Fab fragments, and when compared with such modified IgG, a protein complex provided herein comprising such two scFv fragments as the first and second antigen-binding domains can have at least 10% reduction in simultaneous binding of the two scFv by the respective antigen. The percentage of the reduction can be, for example without limitation, about 10%, about 20%, about 30%, about 40%, about 50%, about 60%, about 70%, about 80%, or about 90%.

The term "simultaneous binding" refers to the co-occupation of the first antigen-binding domain and the second antigen-binding domain by their respective antigen. The simultaneous binding can be determined using any suitable methods known in the art. For example, the first antigen is immobilized on a substrate, and then the protein complex is allowed to bind to the first antigen, after removing the unbound protein complex, the second antigen (which may or may not be the same as the first antigen) is added to allow simultaneous binding to the protein complex, the unbound second antigen is then removed, and the presence/amount of the bound second antigen is detected as an indicator for simultaneous binding.

In certain embodiments, the simultaneous binding of the first antigen-binding domain and the second antigen-binding domain can bring the antigen targets in sufficient proximity or in appropriate spatial orientation thereby induces a functional interaction between the bound antigen targets. The term "functional interaction" as used herein refers to an interaction that changes the biological status of the antigen target, for example without limitation, an inactivated target may be activated by the interaction, an activated target may be inactivated by the interaction, or a target not involved in a signal transduction may be induced to signaling by the interaction.

In certain embodiment, the formation of the dimer renders a steric hindrance such that when the first antigen-binding domain binds to an antigen target, the second antigen-binding domain is substantially prevented from binding to a second antigen target, as a result, the functional interaction (e.g., signal transduction) caused by simultaneous binding of the first and second antigen binding domains is substantially reduced. "Substantially prevented" as used herein refers to that the antigen-binding domain has reduced capability of binding to the antigen target, or if the antigen-binding domain manages to bind to the antigen target, such binding does not tend to induce a functional interaction involving the bound antigen target.

In certain embodiments, the functional interaction between the bound antigen targets comprises signal transduction. "Signal transduction" as used herein refers to a functional interaction between the simultaneously bound antigen targets that can lead to activation of at least one of the antigen targets. Upon activation, the activated antigen target may attract and react with an effector molecule and thereby open up the signal pathway to a biological response. The effector molecule may be transformed into is active form, or may be transformed to allow formation of an active complex with other signal molecules, or may be translocated to a certain functional region of the cell, or may be inactivated to allow progression of the signal pathway if the effector molecule is inhibitory on the pathway. The signal transduction may result in one or more biological response. The term "biological response" as used herein refers to change in cellular activities, including without limitation, cell proliferation, cell death, cell movement, release of molecules, expression of proteins, and relocation of molecules. The signal transduction of the antigen targets may be determined at any suitable level of the signal transduction. For example, the binding of the effector molecule to the activated antigen target can be determined, the amount of the transformed effector molecule or the effector molecule complex or the related/downstream effector molecules can be determined, the location of the effector molecule or the effector molecule complex or the related/downstream effector molecules can be determined, or the biological response may be determined. A variety of methods and assays for determination of signal transduction are well available in the art. Examples of suitable methods may include, without limitation, those involves using radio-labeled or fluorescent-labeled effector molecules for determination of effector binding to the activated antigen target, those involves using radio-labeled or fluorescent-labeled antibodies for an effector molecule or the effector molecule complex or the related/downstream effector molecules, assays for biological responses such as for cell proliferation, cell death, cell movement, release of molecules, expression of proteins, and relocation of molecules. A person skilled in the art can select an appropriate assay according the activated antigen target and the related signal transduction pathway.

Linker

In certain embodiments, the first polypeptide further comprises a first linker, and the second polypeptide further comprises a second linker. In certain embodiments, the first linker or the second linker comprises a peptide linker. In certain embodiments, the first polypeptide further comprises a first peptide linker, and the N-terminal of the first peptide linker is covalently linked to the C-terminal of the first protein monomer, and the C-terminal of the first peptide linker is covalently linked to the N-terminal of the first antigen-binding domain. In certain embodiments, the second polypeptide further comprises a second peptide linker, and the N-terminal of the second peptide linker is covalently linked to the C-terminal of the second protein monomer, and the C-terminal of the second peptide linker is covalently linked to the N-terminal of the second antigen-binding domain.

Figure 5:
FIG. 5: Monospecific DISCObody configuration. A CH3 or CH2CH3 sequence is linked to a Fab or scFv via a flexible linker containing cysteine residue(s). The hinge can be linked to the VH or VL of the Fab and scFv. CH3 or CH2CH3 fusion proteins form homodimer and consequently to promote inter-chain hinge disulfide bond formation. The hinge disulfide bond(s) locks the antigen binding domains close in space and creates spatial hindrance for simultaneous occupation of the both binding sites on antibody by antigens. The disulfide bond (s) should also restrict the orientation of the bound antigens because of the spatial crowdedness around the antibody binding sites.

In certain embodiments, the peptide linker comprises a thiol residue-containing peptide linker. "Thiol residue" as used herein refers to an amino acid containing a thiol group. In certain embodiments, the thiol residue comprises a cysteine residue. Exemplary structures of protein complexes comprising thiol residue-containing peptide linker are shown in FIG. 5.

In certain embodiments, the first peptide linker contains a first thiol residue and the second peptide linker contains a second thiol residue, and the first peptide linker and the second peptide linker form a disulfide bond. In certain embodiments, the disulfide bond substantially reduces the simultaneous binding of the first antigen-binding domain and the second antigen-binding domain to an antigen. In certain embodiments, the disulfide bond substantially reduces the co-occupation of the antigen-binding domains by the respective antigen target. In certain embodiments, the disulfide bond substantially reduces the signal transduction of the simultaneously bound antigen targets, at least partially by restricting the proximity or spatial orientation of the bound antigen targets.

Without being bound to theory, it is believed that, a suitable distance between the disulfide bond and the C-terminals of the peptide linkers can discourage the simultaneous antigen binding of the first antigen-binding domain and the second antigen-binding domain, which are located near the C-terminals of the peptide linkers. If the disulfide bond is sufficiently close to the C-terminals of the peptide linkers, the disulfide bond may render a steric hindrance such that when the first antigen-biding domain binds to an antigen target, the second antigen-binding domain is substantially prevented from binding to a second antigen target, as a result, the functional interaction (e.g., signal transduction) caused by simultaneous binding of the first and second antigen binding domains is substantially reduced.

In certain embodiments, the first thiol residue is 1-10 amino acid residues away from the C-terminal of the first peptide linker. In certain embodiments, the second thiol residue is 1-10 amino acid residues away from the C-terminal of the second peptide linker.

In certain embodiments, the thiol residue-containing peptide linker can comprise at least a fragment of a hinge sequence of an immunoglobin. In certain embodiments, the thiol residue-containing peptide linker comprises at least a fragment of a hinge sequence of Ig G. In certain embodiments, the thiol residue-containing peptide linker comprises a amino acid sequence of: CysProProCys (SEQ ID NO: 68), or ThrHisThrCysProProCysProAlaPro (SEQ ID NO: 69), or AspLysThrHisThrCysProProCysProAlaPro (SEQ ID NO: 70).

Additional Antigen-Binding Domains

In certain embodiments, the polypeptide complex can further comprise one or more additional antigen-binding domains operably linked to any N-terminal having a free amine group (—NH$_2$) or any C-terminal having a free carboxyl group (—COOH) of the polypeptide complex.

In certain embodiments, the N-terminal of the first protein monomer is operably linked a third antigen-binding domain. In certain embodiments, the N-terminal of the second protein monomer is operably linked to a fourth antigen-binding domain (see, for example, FIGS. 6 and 7, "U" position). In certain embodiments, the C-terminal of the first antigen-binding domain is operably linked to a fifth antigen-binding domain. In certain embodiments, the C-terminal of the second antigen-binding domain is operably linked to a sixth antigen-binding domain (see, for example, FIGS. 6 and 7, "W" and/or "V" position).

Figure 6:
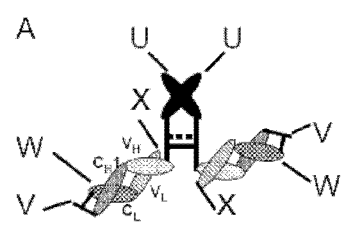
FIG. 6: Mutispecific Fab DISCObody configuration. Multispecific Fab DISCObody is generated by fusion of additional binding domains to the Fab monospcific DISCObody (FIG. 5). Fusions can be made at the N-terminus of CH3 or CH2CH3, the C-terminus of Fd or LC and the N-terminus of LC (A) or Fd (VHCH1) (B). The mentioned additional binding domains can be in the form of Fab, scFv, single domain antibodies (dAb), single domain camel antibody (camelid VHH), or binders based on non antibody domain scaffolds such as Fibronectin 3 domain (Fn3), ankryin repeats, and other scaffolds.
Figure 6:
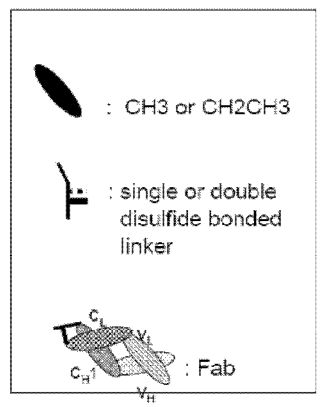
Figure 6:
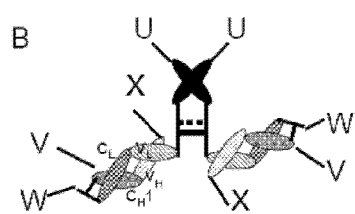
Figure 6:
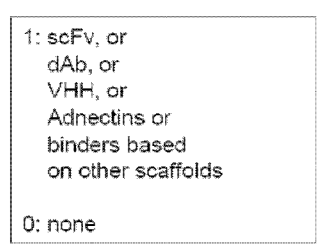
Figure 7:
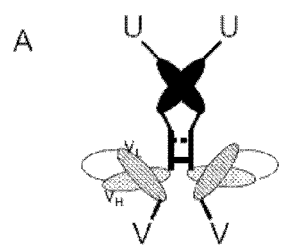
FIG. 7: Multispecific scFv DISCObody configuration. Multispecific scFv DISCObody is generated by fusion of additional binding domains to the Fab monospecific DISCObody (FIG. 5). Fusions can be made at the N-terminus of CH3 or CH2CH3, and the C-terminus of VL (A) or VH (B). The mentioned additional binding domains can be in the form of Fab, scFv, single domain antibodies (dAb), single domain camel antibody (camelid VHH), or binders based on non antibody domain scaffolds such as Fibronectin 3 domain (Fn3), ankryin repeats, and other scaffolds.
Figure 7:
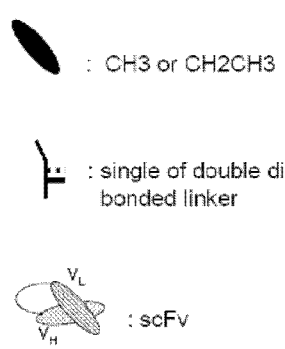
Figure 7:
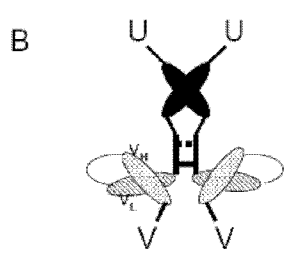
Figure 7:
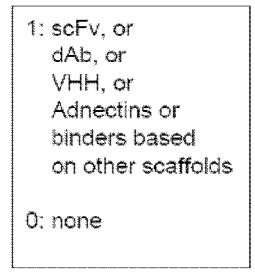
Figure 7:
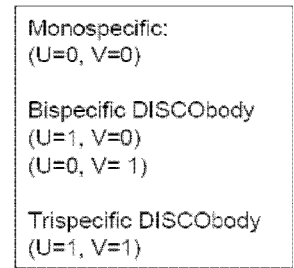

In certain embodiments, the first antigen-binding domain or the second antigen-binding domain is a first light chain fragment which is disulfidely bonded to a first heavy chain fragment (see, for example, FIG. 6 B). In certain embodiments, the C-terminal of the first light chain fragment is operably linked to a seventh antigen-binding domain (see, for example, FIG. 6 B, "W" position). In certain embodiments, the C-terminal of the first heavy chain fragment is operably linked to an eighth antigen-binding domain (see, for example, FIG. 6 B, "V" position). In certain embodiments, the N-terminal of the first heavy chain fragment is operably linked to a ninth antigen-binding domain (see, for example, FIG. 6 B, "X" position).

In certain embodiments, the first antigen-binding domain or the second antigen-binding domain is a second heavy chain fragment which is disulfidely bonded to a second light chain fragment (see, for example, FIG. 6 A). In certain embodiments, the C-terminal of the second heavy chain fragment is operably linked to a tenth antigen-binding domain (see, for example, FIG. 6 A, "V" position). In certain embodiments, the C-terminal of the second light chain fragment is operably linked to an eleventh antigen-binding domain (see, for example, FIG. 6 A, "W" position). In certain embodiments, the N-terminal of the second light chain fragment is operably linked to a twelfth antigen-binding domain (see, for example, FIG. 6 A, "X" position).

In certain embodiments, the additional antigen-binding domain can be an antibody-derived component or a non-antibody component. In certain embodiments, the additional antigen-binding domain is selected from the group consisting of a CDR, a Fv, a VL, a VH, a light chain, and a heavy chain, a ScFv, a Fab, camelid VHH, dAb, Fibronectin 3 domain (Fn3), an ankryin repeat, and an Adnectin.

In certain embodiments, the antigen-binding domains in the polypeptide complex specifically bind to an antigen target that is associated with a condition. The condition may include a physiological condition, a pathological condition and a cosmetic condition. Examples of suitable conditions include, without limitation, tumor, cancer, inflammation, allograft transplantation, type I diabetes, and multiple sclerosis.

In certain embodiments, the antigen target is negatively associated with the condition. In certain embodiments, the binding of the antigen target by the polypeptide complex can inactivate or antagonize the biological function of the antigen target, and thereby improve the condition.

The antigen-binding domains in the polypeptide complex can specifically bind to any suitable antigen targets. Examples of suitable antigen targets include, without limitation, TNF receptor (see, e.g., Shen H. M. et al, FASEB J. 20(10):1589-98 (2006)), cMet (see, e.g., Bottaro, D. P. et al, Science, 251 (4995): 802-804 (1991)), CD3 (see, e.g., Chetty R. et al, J Pathol., 173(4): 303-7 (1994)), CD40 (see, e.g., Chatzigeorgiou A. et al, Biofactors., 35(6): 474-83 (2009)), DR3 (see, e.g., Meylan F. et al, Immunity., 29(1): 79-89 (2008)), FcγR (see, e.g., Torkildsen O. et al, Acta Neurol Scand Suppl. 183:61-3 (2006)), NKG2D (see, e.g., Obeidy P. et al, Int J Biochem Cell Biol., 41(12):2364-7 (2009)), IL-6 (see, e.g. Ferguson-Smith et al, Genomics 2 (3): 203-208 (1988)), PCSK9 (Lambert G. et al, Curr. Opin. Lipidol. 18 (3): 304-9 (2007)) and any derivative thereof.

The additional antigen-binding domains can be the same or not the same of the first antigen-binding domain or of the second antigen-binding domain. The additional antigen-binding domains can bind to the same or not the same target as the first antigen-binding domain or the second antigen-binding domain.

In certain embodiments, when the first and the second antigen-binding domains are bound by a first antigen target, the additional antigen-binding domain can simultaneously bind to a second antigen target. In certain embodiments, when binding to either target alone, the polypeptide complexes do not cause substantial functional interaction involving the bound target, but when simultaneously binding to both the first target and the second target, the polypeptide complexes can promote a functional interaction between the two targets. For example, a polypeptide complex can bound to a first antigen target which is CD3, and a second antigen target which is tumor surface antigen, when the polypeptide complex is bound to either CD3 or the tumor surface antigen, the T cells will not be activated, however, when CD3 and the tumor surface antigen are simultaneously bound to the polypeptide complex, the T cells are activated in the vicinity of cancer cells bearing the tumor surface antigen, and therefore significantly enhance the tumor killing efficiency of T cells and reduce or prevent the side effects such as cytokine storm due to activation of CD3.

In certain embodiments, the combination of the first antigen target and the second antigen target can be CD3 and tumor surface antigen, which combination can enhance tumor killing effects by T cells. In certain embodiments, the combination of the first antigen target and the second antigen target can be FcγR and tumor surface antigen, which combination can induce FcγR-expressing immune cells to kill tumor cells. In certain embodiments, the combination of the first antigen target and the second antigen target can be CD3 and NKG2D, which combination can induce natural killer (NK) cell to kill tumor cells.

In certain embodiments, when the first and the second antigen-binding domains is bound by a first antigen target, the additional antigen-binding domains can simultaneously bind to a second antigen target and a third antigen target. In certain embodiments, one of the first antigen target, the second antigen target and the third antigen target can be selected from the group consisting of CD3, FcγR and NKG2D, and the other two can be two different antigens preferentially expressed on cancer cells. Such combination may enhance the targeting specificity for tumor cells and prevent killing of normal cells that express a single antigen or that express low levels of the antigens.

In certain embodiments, when the first and the second antigen-binding domains is bound by a first antigen target, the additional antigen-binding domains can simultaneously bind to a second antigen target, a third antigen target and a fourth antigen target. In certain embodiments, when the first and the second antigen-binding domains is bound by a first antigen target, the additional antigen-binding domains can simultaneously bind to a second antigen target, a third antigen target, a fourth antigen target and a fifth antigen target.

Functions and Advantages

The polypeptide complexes are functional in binding to antigen targets and can provide advantages over other antigen-binding proteins in certain circumstances.

In certain embodiments, the polypeptide complexes have substantially reduced simultaneous binding of the first antigen-binding domain and the second antigen-binding domain to an antigen target. Such polypeptide complexes can be functional in inhibition of the antigen targets, preferably for those antigen targets that tend to be activated when brought in sufficient proximity, e.g. by simultaneous binding to the first and the second antigen-binding domains. Unwanted activation of the antigen targets caused by simultaneous binding can be undesirable and in certain circumstances even detrimental, where the elimination and/or inhibition of the targets is needed. For example, when conventional antibody is used to treat a tumor by inhibiting a receptor tyrosine kinase, the antigen-binding domains of the conventional antibody can simultaneously accommodate two receptor tyrosine kinases which are brought close enough so that they can phosphorylate each other into an activated form and induce signal transduction leading to aggravation of the tumor condition. Activation of antigen targets can also result in other side effects, for example, current anti-CD3 antibodies can activate CD3 and induce side effects such as cytokine storm, lymphopenia, redistribution and marginalization of T cells, reactivation of Epstein-Barr virus (EBV). Certain embodiments of the polypeptide complex provided herein can substantially reduce simultaneous binding of the antigen targets and hence prevent or reduce target activation, and thereby enhance the efficiency of target inhibition as well as prevent or reduce the side effects related to target activation.

In certain embodiments, the polypeptide complexes further comprise one or more additional antigen-binding domains apart from the first and the second antigen-binding domains. The additional antigen-binding domains may bind to one or more antigen targets different from the existing antigen target bound by the first and the second antigen-binding domain. In certain embodiments, the one or more antigen targets can be a molecule locating nearby the existing antigen target, such that the polypeptide complexes can be specifically enriched in the neighborhood of the existing antigen target and thus improve the specificity of the action. In certain embodiments, the one or more antigen targets can involve in the same or similar condition as the existing antigen target, and the polypeptide complex can be functional in simultaneously inhibiting multiple targets and thus provide combinatorial or even synergistic effects on the condition or be effective on a broad band of related conditions, such as a broad band of tumors. In certain embodiments, the one or more additional antigen targets can be immune cell surface markers, and the existing antigen target can be a disease target, by simultaneous binding to the immune cell surface marker and the disease target, the polypeptide complex can draw the immune cell to the disease target and promote the immune response against the disease target. In certain embodiments, the one or more antigen targets can be two different markers present on a diseased cell, and the existing antigen target can be an immune cell surface marker, by simultaneous binding to the two disease markers, the polypeptide complex can specifically direct the immune cell to the target containing both disease targets and promote the immune response against the diseased cell, as a result, unwanted immune response to normal cells containing only one of the disease marker can be prevented or reduced.

In certain embodiments, the protein monomers of the polypeptide complex are CH3 domain whose C-terminal is operably linked to the N-terminal of the antigen-binding domain. Compared with conventional antibodies, the polypeptide complexes lack the CH2 domain and optionally partial of the hinge sequence, both of which are believed to involve in Fc receptor binding. Fc receptor binding can induce activation of antigen targets by forming Fc receptor clusters and thereby bring close the bound antibodies as well as the bound antigen targets. Certain embodiments of the polypeptide complexes do not contain the CH2 domains and optionally partial of the hinge sequence, and therefore can have greatly reduced Fc receptor binding and thereby prevent or reduce the Fc receptor induced antigen target activation or other side effects.

In addition to reduction in Fc receptor binding, polypeptide complexes lacking a CH2 domain can also have a shortened serum half life, which can be desirable in circumstances where long serum half life is not needed. For example, the polypeptide complex lacking the CH2 domain can have a decreased molecular size but can still be greater than 60 kD, which is the renal filtration size, and therefore will not be filtered from the blood and can have a medium serum half life of about 1-2 days.

In case long serum half life is desired, the polypeptide can be fused to a CH2 domain if Fc receptor binding is not a concern, or linked to a conjugate such as a polymer conjugate, albumin, or albumin binder, to increase the molecular size and therefore have a longer serum half life.

Polypeptide

In another aspect, the present disclosure provides a polypeptide comprising a protein monomer and an antigen-binding domain, in which the C-terminal of the protein monomer is operably linked to the N-terminal of the antigen-binding domain.

In certain embodiments, the C-terminal of the protein monomer is directly linked to the N-terminal of the antigen-binding domain by one or more chemical bonds. In certain embodiments, the one or more chemical bonds comprise a covalent bond. In certain embodiments, the one or more chemical bonds comprise a peptide bond.

In certain embodiments, the C-terminal of the protein monomer is indirectly linked to the N-terminal of the antigen-binding domain by a linker. In certain embodiments, the linker can be a peptide linker, a polymer linker or a chemical linker. In certain embodiments, the polypeptide further comprises a linker and one end of the linker is covalently linked to the C-terminal of the protein monomer, and the other end of the linker is covalently linked to the N-terminal of the antigen-binding domain.

In certain embodiments, the linker is a peptide linker. In certain embodiments, the polypeptide further comprises a peptide linker, and the N-terminal of the peptide linker is covalently linked to the C-terminal of the protein monomer, and the C terminal of the peptide linker is covalently linked to the N-terminal of the antigen-binding domain.

In certain embodiments, the peptide linker is a thiol residue-containing peptide linker. In certain embodiments, the thiol residue comprises a cysteine residue.

In certain embodiments, the protein monomer comprises an antibody-derived monomer or a non-antibody monomer. In certain embodiments, the protein monomer comprises an antibody-derived component. In certain embodiments, the protein monomer comprises a CH3 domain from an immunoglobulin and the C-terminal of the CH3 domain is operably linked to the N-terminal of the antigen-binding domain. In certain embodiments, the protein monomer further comprises a CH2 domain from an immunoglobulin and the C-terminal of the CH2 domain is covalently linked to the CH3 domain. In certain embodiments, the immunoglobulin is selected from the group consisting of Ig A, Ig D, Ig E, Ig G, and Ig M.

In certain embodiments, the antigen-binding domain comprises an antibody-derived component or a non-antibody component. In certain embodiments, the antigen-binding domain is selected from the group consisting of a CDR, a Fv, a VL, a VH, a light chain, and a heavy chain, a ScFv, a Fab, camelid VHH, dAb, Fn3, an ankryin repeat, and an Adnectin.

In certain embodiments, the antigen-binding domain specifically binds to an antigen target. In certain embodiments, the antigen target is associated with a condition. In certain embodiments, the condition is a physiological condition, a pathological condition or a cosmetic condition. In certain embodiments, the antigen target comprises TNF receptor, cMet, CD3, CD40, DR3, FcγR, NKG2D, IL-6, PCSK9, and any derivative thereof.

In certain embodiments, a first polypeptide and a second polypeptide can form the polypeptide complex provided herein. In certain embodiments, the first polypeptide comprises a first protein monomer and the second polypeptide comprises a second protein monomer, and the first protein monomer forms a dimer with the second protein monomer to provide the polypeptide complex provided herein. The first monomer and the second monomer can form a dimer through one or more chemical bonds or through one or more linkers. The one or more chemical bonds can comprise a covalent bond such as peptide bond or disulfide bone, and/or a non-covalent bond such as a hydrogen bond, a hydrophobic bond, an ionic bond, or a Van der Waals bond. The one or more linkers can comprise a peptide linker, a polymer linker or a chemical linker.

In certain embodiments, the first polypeptide and the second polypeptide are the same or not the same. In certain embodiments, the first protein monomer and the second protein monomer are the same or not the same. In certain embodiments, the first antigen-binding domain and the second antigen-binding domain are the same or not the same.

Polynucleotide, Vectors and Host Cells

In another aspect, the present disclosure provides an isolated polynucleotide encoding the polypeptide provided herein. The polynucleotide can be DNA or RNA. The polynucleotide may be isolated and amplified using any suitable methods known in the art, such as for example, polymerase chain reaction (PCR).

In certain embodiments, the isolated polynucleotide is inserted into a vector. The term "vector" as used herein refers to a vehicle into which a polynucleotide encoding a protein may be operably inserted so as to bring about the expression of that protein and/or the cloning of the polynucleotide. The isolated polynucleotide may be inserted into a vector using any suitable methods known in the art, for example, without limitation, methods involving using of restriction enzymes, i.e. the vector may be digested using appropriate restriction enzymes and then may be ligated with the isolated polynucleotide having matching restriction ends.

Examples of suitable vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

For expression of the polypeptide, the vector may be introduced into a host cell to allow expression of the polypeptide within the host cell. The expression vectors may contain a variety of elements for controlling expression, including without limitation, promoter sequences, transcription initiation sequences, enhancer sequences, selectable markers, and signal sequences. These elements may be selected as appropriate by a person of ordinary skill in the art. For example, the promoter sequences may be selected to promote the transcription of the polynucleotide in the vector. Suitable promoter sequences include, without limitation, T7 promoter, T3 promoter, SP6 promoter, beta-actin promoter, EF1a promoter, CMV promoter, and SV40 promoter. Enhancer sequences may be selected to enhance the transcription of the polynucleotide. Selectable markers may be selected to allow selection of the host cells inserted with the vector from those not, for example, the selectable markers may be genes that confer antibiotic resistance. Signal sequences may be selected to allow the expressed polypeptide to be transported outside of the host cell.

A vector may also include materials to aid in its entry into the cell, including but not limited to a viral particle, a liposome, or a protein coating.

For cloning of the polynucleotide, the vector may be introduced into a host cell to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art. For example, the origin of replication may be selected to promote autonomous replication of the vector in the host cell.

In certain embodiments, the present disclosure provides a vector comprising a first polynucleotide encoding the first polypeptide disclosed herein and a second polynucleotide encoding the second polypeptide disclosed herein. In certain embodiments, the present disclosure provides a first vector comprising a first polynucleotide encoding the first polypeptide disclosed herein. In certain embodiments, the present disclosure provides a second vector comprising a second polynucleotide encoding the second polypeptide disclosed herein.

In certain embodiments, the present disclosure provides host cells containing the vector provided herein. The host cells containing the vector may be useful in expression or cloning of the polynucleotide contained in the vector.

Suitable host cells can include, without limitation, prokaryotic cells, fungal cells, or higher eukaryotic cells.

Suitable prokaryotic cells for this purpose include, without limitation, eubacteria, such as Gram-negative or Gram-positive organisms, for example, Enterobactehaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*.

Suitable fungal cells for this purpose include, without limitation, filamentous fungi and yeast. Illustrative examples of fungal cells include, *Saccharomyces cerevisiae*, common baker's yeast, *Schizosaccharomyces pombe, Kluyveromyces* hosts such as, eg., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402, 226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Higher eukaryotic cells, in particular, those derived from multicellular organisms can be used for expression of glycosylated polypeptide provided herein. Suitable higher eukaryotic cells include, without limitation, invertebrate cells and insect cells, and vertebrate cells. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, *petunia*, tomato, and tobacco can also be utilized as hosts. Examples of vertebrate cells include, mammalian host cell lines such as monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse Sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annuals N.Y. Acad. Sci. 383:44-68 (1982)); MRC 5 cells; FS4 cells; and a human hepatoma line (Hep G2).

The vector can be introduced to the host cell using any suitable methods known in the art, including, without limitation, DEAE-dextran mediated delivery (Gulick, T., Curr. Protoc. Mol. Biol., Chapter 9, Unit 9.2, (2001)), calcium phosphate precipitate method (Kingston, R. E. et al, Curr. Protoc. Mol. Biol., Chapter 10, Unit 10.13, (2001)), cationic lipids mediated delivery (Hirko, A. et al, Curr. Med. Chem., 10(14): 1185-1193 (2003)), liposome mediated transfection (Schenborn, E. T. et al, Methods in Molecular Biology, 130:155-164 (2000)), electroporation (Nature Methods, 3:67-68 (2006)), microprojectile bombardment, receptor-mediated gene delivery (Varga, C. M. et al, Biotechnol. Bioeng., 70(6): 593-605 (2000)), viral vector mediated gene delivery (Young, L. S. et al, J. Pathol., 208(2): 299-318 (2006)), delivery mediated by polylysine (Zauner, W. et al, Advanced Drug Delivery Reviews, 30(1-3): 97-113 (1998)), histone (Wagstaff, K. M. et al, Mol. Ther, 15 (4): 721-731 (2007)), chitosan (Koping-Hoggard, M. et al, Gene Therapy, 11: 1441-1452 (2004)), and peptides (Martin, M. E. et al, The APPS Journal, 9(1): E18-E29 (2007)).

In certain embodiments, the host cells comprise a first vector comprising the first polynucleotide encoding a first polypeptide and a second vector comprising the second polynucleotide encoding a second polypeptide. In certain embodiments, the first vector and the second vector may be the same or not the same. In certain embodiments, the first polypeptide and the second polypeptide may be the same or not the same.

In certain embodiments, the first vector and the second vector may or may not be introduced simultaneously. In certain embodiments, the first vector and the second vector may be introduced together into the host cell. In certain embodiments, the first vector may be introduced first into the host cell, and then the second vector may be introduced. In certain embodiments, the first vector may be introduced into the host cell which is then established into a stable cell line expressing the first polypeptide, and then the second vector may be introduced into the stable cell line.

In certain embodiments, the host cells comprise a vector comprising both the first polynucleotide encoding for a first polypeptide and the second polynucleotide a second polypeptide. In certain embodiments, the first polypeptide and the second polypeptide may be the same or not the same.

In certain embodiments, the present disclosure provides a host cell comprising the first polynucleotide and the second polynucleotide. In certain embodiments, the present disclosure provides a host cell comprising a polypeptide complex disclosed herein. In certain embodiments, the polypeptide complex or the polypeptide is secreted from the host into a surrounding medium or environment.

In certain embodiments, the present disclosure provides methods of expressing the polypeptide provided herein, comprising culturing the host cell containing the vector under conditions in which the inserted polynucleotide in the vector is expressed.

Suitable conditions for expression of the polynucleotide may include, without limitation, suitable medium, suitable density of host cells in the culture medium, presence of necessary nutrients, presence of supplemental factors, suitable temperatures and humidity, and absence of microorganism contaminants. A person with ordinary skill in the art can select the suitable conditions as appropriate for the purpose of the expression.

In certain embodiments, the polypeptide expressed in the host cell can form a dimer and thus produce the polypeptide complex provided herein. In certain embodiments, the polypeptide expressed in the host cell can form a polypeptide complex which is a homodimer. In certain embodiments, where the host cells express a first polynucleotide and a second polynucleotide, the first polynucleotide and the second polynucleotide can form a polypeptide complex which is a heterodimer.

In certain embodiments, the polypeptide complex may be formed inside the host cell. For example, the dimer may be formed inside the host cell with the aid of relevant enzymes and/or cofactors. In certain embodiments, the polypeptide complex may be secreted out of the cell. In certain embodiments, the first polypeptide and the second polypeptide may be secreted out of the host cell and form a dimer outside of the host cell.

In certain embodiments, the first polypeptide and the second polypeptide may be separately expressed and allowed to dimerize under suitable conditions. For example, the first polypeptide and the second polypeptide may be combined in a suitable buffer and allow the first protein monomer and the second protein monomer to dimerize through appropriate interactions such as hydrophobic interactions. For another example, the first polypeptide and the second polypeptide may be combined in a suitable buffer containing an enzyme and/or a cofactor which can promote the dimerization of the first polypeptide and the second polypeptide. For another example, the first polypeptide and the second polypeptide may be combined in a suitable vehicle and allow them to react with each other in the presence of a suitable reagent and/or catalyst.

In certain embodiments, the method further comprises a step of purifying or isolating the polypeptide or polypeptide complex. The expressed polypeptide and/or the polypeptide complex can be purified or isolated using any suitable methods. The polypeptide and/or the polypeptide complex can be expressed intracellularly, in the periplasmic space or be secreted outside of the cell into the medium. If the polypeptide and/or the polypeptide complex is expressed intracellularly, the host cells containing the polypeptide and/or the polypeptide complex may be lysed and polypeptide and/or the polypeptide complex may be isolated from the lysate by removing the unwanted debris by centrifugation or ultrafiltration. If the polypeptide and/or the polypeptide complex is secreted into periplasmic space of $E.\ coli$, the cell paste may be thawed in the presence of agents such as sodium acetate (pH 3.5), EDTA, and phenylmethylsulfonylfluoride (PMSF) over about 30 min, and cell debris can be removed by centrifugation (Carter et al., BioTechnology 10:163-167 (1992)). If the polypeptide and/or the polypeptide complex is secreted into the medium, the supernatant of the cell culture may be collected and concentrated using a commercially available protein concentration filter, for example, an Amincon or Millipore Pellicon ultrafiltration unit. A protease inhibitor and/or a antibiotics may be included in the collection and concentration steps to inhibit protein degradation and/or growth of contaminated microorganisms.

The expressed polypeptide and/or the polypeptide complex can be further purified by a suitable method, such as without limitation, affinity chromatography, hydroxylapatite chromatography, size exclusion chromatography, gel electrophoresis, dialysis, ion exchange fractionation on an ion-exchange column, ethanol precipitation, reverse phase HPLC, chromatography on silica, chromatography on heparin sepharose, chromatography on an anion or cation exchange resin (such as a polyaspartic acid column), chromatofocusing, SDS-PAGE, and ammonium sulfate precipitation (see, for review, Bonner, P. L., Protein purification, published by Taylor & Francis, 2007; Janson, J. C., et al, Protein purification: principles, high resolution methods and applications, published by Wiley-VCH, 1998).

In certain embodiments, the polypeptides and/or polypeptide complexes can be purified by affinity chromatography. In certain embodiments, protein A chromatography or protein A/G (fusion protein of protein A and protein G) chromatography can be useful for purification of polypeptides and/or polypeptide complexes comprising a component derived from antibody CH2 domain and/or CH3 domain (Lindmark et al., J. Immunol. Meth. 62:1-13 (1983)); Zettlit, K. A., Antibody Engineering, Part V, 531-535, 2010). In certain embodiments, protein G chromatography can be useful for purification of polypeptides and/or polypeptide complexes comprising IgG γ3 heavy chain (Guss et al., EMBO J. 5:1567 1575 (1986)). In certain embodiments, protein L chromatography can be useful for purification of polypeptides and/or polypeptide complexes comprising κ light chain (Sudhir, P., Antigen engineering protocols, Chapter 26, published by Humana Press, 1995; Nilson, B. H. K. et al, J. Biol. Chem., 267, 2234-2239 (1992)). The matrix to which the affinity ligand is attached is most often agarose, but other matrices are available. Mechanically stable matrices such as controlled pore glass or poly(styrenedivinyl)

benzene allow for faster flow rates and shorter processing times than can be achieved with agarose. Where the antibody comprises a CH3 domain, the Bakerbond ABX resin (J. T. Baker, Phillipsburg, N.J.) is useful for purification.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Compositions and Methods of Use

In another aspect, the present disclosure provides a pharmaceutical composition comprising a therapeutically effective amount of the polypeptide complex provided herein and a pharmaceutically acceptable carrier.

In certain embodiments, the pharmaceutical composition comprises a therapeutically effective amount of the polypeptide complex provided herein. The term "therapeutically effective amount" or "therapeutically effective dosage" as used herein refers to the amount or concentration of the polypeptide complex which is effective to treat the condition associated with the antigen target to which the polypeptide complex can bind. "Treating" or "treatment" as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

The therapeutic effective amount of the polypeptide complex as provided herein will depend on various factors known in the art, such as for example, body weight, age, past medical history, present medications, state of health of the subject and purpose of the treatment, potential for cross-reaction, allergies, sensitivities and adverse side-effects, as well as the administration route and extent of the development of the condition. Dosages may be proportionally reduced or increased by one of ordinary skill in the art (e.g., physician or veterinarian) as indicated by these and other circumstances or requirements.

The term "pharmaceutically acceptable carrier" as used herein refers to a pharmaceutically acceptable material, composition or vehicle, including solid or liquid diluents, excipients, salts, or solvents that are involved in carrying the polypeptide complex to its intended action site in the recipient and/or that are beneficial for the manufacture and/or storage of the polypeptide complex. A carrier is "pharmaceutically acceptable" in the sense of being compatible with the other ingredients comprising the formulation, and physiologically compatible with the recipient thereof, commensurate with a reasonable risk/benefit ratio.

Pharmaceutical acceptable carriers for use in the pharmaceutical compositions disclosed herein can include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, non-toxic auxiliary substances, fillers, binders, disintegrants, buffers, preservatives, lubricants, flavorings, thickeners, coloring agents, emulsifiers, other components known in the art, or various combinations thereof.

Suitable aqueous vehicles include, without limitation, sodium chloride injection, Ringer's injection, isotonic dextrose injection, sterile water injection, or dextrose and lactated Ringer's injection.

Suitable nonaqueous vehicles include, without limitation, fixed oils of vegetable origin, cottonseed oil, corn oil, sesame oil, or peanut oil.

Suitable antimicrobial agents include, without limitation, phenols or cresols, mercurials, benzyl alcohol, chlorobutanol, methyl and propyl p-hydroxybenzoic acid esters, thimerosal, benzalkonium chloride and benzethonium chloride. The antimicrobial agents in the pharmaceutical compositions can be at bacteriostatic or fungistatic concentrations.

Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in the pharmaceutical composition can decrease oxidation of the polypeptide complex, thereby prevent or reduce loss of binding affinity and improve stability of the polypeptide complex.

Suitable sequestering or chelating agents include, without limitation, EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid.

Suitable excipients may include, for example, water, saline, dextrose, glycerol, or ethanol.

Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

To further illustrate, other pharmaceutically acceptable carriers can include, without limitation, local anesthetics such as procaine hydrochloride, suspending and dispersing agents such as sodium carboxymethylcelluose, hydroxypropyl methylcellulose, or polyvinylpyrrolidone, and emulsifying agents such as Polysorbate 80 (TWEEN-80).

Generally, the pharmaceutical composition can be prepared by bringing the polypeptide complex into uniform association with the pharmaceutically acceptable carriers, dividing to preparation into suitable units, and optionally shaping the product.

In another aspect, the present disclosure provides methods of use for the pharmaceutical composition provided herein. In certain embodiments, the present disclosure provides methods of treating a condition comprising administering an effective amount of the pharmaceutical composition to a subject in need, in which the condition is associated with an antigen to which the polypeptide complex can bind. The "effective amount" as used herein refers to the therapeutically effective amount of the polypeptide complex contained in the pharmaceutical composition.

In certain embodiments, the pharmaceutical composition as provided herein is administered at an effective amount of about 0.01 mg/kg to about 100 mg/kg. In certain of these embodiments, the polypeptide complex as provided herein is administered at a dose of about 0.01 mg/kg, about 0.5 mg/kg, about 1 mg/kg, about 2 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In certain embodiments, the polypeptide complex is administered at a dosage of about 50 mg/kg or less, and in certain of these embodiments the dosage is 10 mg/kg or less, 5 mg/kg or less, 1 mg/kg or less, 0.5 mg/kg or less, or 0.1 mg/kg or less.

A given dosage may be administered at various intervals, such as for example once a day, two or more times per day, two or more times per week, once per week, once every two weeks, once every three weeks, once a month, or once every two or more months. In certain embodiments, dosing frequencies may be adjusted over the course of the treatment to optimize the desired response. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

The pharmaceutical composition provided herein may be administered by any suitable route known in the art, including without limitation, intravenous, intramuscular, intraarterial, intrathecal, intracapsular, intraorbital, intra cardia, intraperitoneal, intraspinal, intradermal, subcutaneous, oral, intranasal, intraocular, sublingual, rectal, transmucosal, epidermal, transdermal or topical routes.

The pharmaceutical composition can be formulated to suit the intended route of administration. In certain embodiments, the pharmaceutical composition can be formulated into an injectable dosage form. The injectable dosage form can be sterile and non-pyretic, and can be in any conventional forms such as solutions, suspensions, and emulsions, as well as solid forms suitable for producing solutions, suspensions or emulsions, such as for example, lyophilized powders, hypodermic tablets, and other dry products ready for combination with an injectable vehicle. The injectable dosage form can comprise an injectable vehicle or can be combined with an injectable vehicle just prior to use. Injectable vehicle can be a sterile and/or non-pyretic liquid, and can be aqueous or non-aqueous. The injectable pharmaceutical composition can be packaged in an ampoule, a vial or a syringe, in unit dosages or multiple dosages.

The pharmaceutical composition can be stored under appropriate conditions to prevent or reduce loss of biological activity of the polypeptide complex, such as for example, at a suitable temperature (e.g. at about 4° C. to room temperature), and under suitable light exposure (e.g. protected from light).

In another aspect, the present disclosure provides a composition comprising the polypeptide complexes provided herein which is linked to one or more conjugates.

A variety of conjugates may be linked to the polypeptide complexes provided herein (see, for example, "Conjugate Vaccines", Contributions to Microbiology and Immunology, J. M. Cruse and R. E. Lewis, Jr. (eds.), Carger Press, New York, (1989)). In certain embodiments, conjugates linked to the polypeptide complexes disclosed herein may comprise one or more agents meant to alter one or more pharmacokinetic properties of the polypeptide complexes, such as for example polyethylene glycol (PEG) to increase the half-life or decrease the immunogenicity of the polypeptide complexes. In certain embodiments, conjugates linked to the polypeptide complexes disclosed herein may comprise one or more detectable labels, including without limitation, radioactive isotopes such as $^{123}$I, $^{124}$I, $^{125}$I, $^{131}$I, $^{35}$S, $^{3}$H, $^{111}$In, $^{112}$In, $^{14}$C, $^{64}$Cu, $^{67}$Cu, $^{86}$Y, $^{88}$Y, $^{90}$Y, $^{177}$Lu, $^{211}$At, $^{186}$Re, $^{188}$Re, $^{153}$Sm, $^{212}$Bi, and $^{32}$P, other lanthanides, luminescent labels or fluorescent labels such as for example fluorescein, rhodamine, dansyl, phycoerythrin, or Texas Red, and enzyme-substrate labels such as for example horseradish peroxidase, alkaline phosphatase, and β-D-galactosidase.

The conjugates may be linked to the polypeptide complexes by covalent binding, affinity binding, intercalation, coordinate binding, complexation, association, blending, or addition, among other methods. In certain embodiments, the polypeptide complexes disclosed herein may be engineered to contain specific sites outside the antigen-binding portion that may be utilized for binding to one or more conjugates. For example, such a site may include one or more reactive amino acid residues, such as for example cysteine or histidine residues, to facilitate covalent linkage to a conjugate. In certain embodiments, the antibodies may be linked to a conjugate indirectly, or through another conjugate. For example, the polypeptide complexes may be conjugated to biotin, then indirectly conjugated to a second conjugate that is conjugated to avidin.

In another aspect, the present disclosure provides non-therapeutic uses of the polypeptide complexes. In certain embodiments, a method is provided for detecting the presence of an antigen target in a sample, comprising contacting the sample with the polypeptide complex provided herein, and determining the presence of the antigen target. In certain embodiments, the polypeptide complexes conjugated with a detectable label may be used. In certain embodiments, the polypeptide complexes may not comprise a detectable conjugate but can be detected using a labeled material such as a labeled antibody that can specifically bind to the polypeptide complex.

In certain embodiments, the polypeptide complexes can be used in in vivo or in vitro diagnostic applications. The polypeptide complex may be used to diagnose a condition associated with the antigen target to which the polypeptide complex can specifically bind. In certain embodiments, the polypeptide complexes conjugated with or without a detectable label may be used. In certain embodiments, the polypeptide complex may be used to contact with a biological sample from a subject to determine the presence and/or expression amount of the antigen target in the biological sample and thereby determine the status of the condition in the subject. In certain embodiments, the polypeptide complex may be administered in a subject, and the binding to the antigen target can be detected using methods known in the art.

In certain embodiments, the polypeptide complexes may be used as affinity purification agents to purify the antigen target. In these embodiments, the antibodies or antigen-binding fragments may be immobilized on a solid phase such as a resin or filter paper using methods known in the art. The polypeptide complexes may also be used to precipitate the antigen target from a solution.

In certain embodiments, the polypeptide complexes can be used to reduce the simultaneous binding of antigen targets to both the first and the second antigen-binding domains. In certain embodiments, conventional antibodies or antigen-binding fragments capable of binding to two antigens may be engineered into a polypeptide complex provided herein, and the simultaneous binding of the two antigens may be then determined. For example, the polynucleotides encoding a conventional antibody may be rearranged to make a first polynucleotide which encodes the CH3 domain, CH2 domain, hinge sequence, CH1 domain and VH domain sequentially from 5' end to 3' end, and a second polynucleotide which encodes CL domain and VL domain sequentially from 5' end to 3' end. The polynucleotides may be further modified to suit specific needs, for example, the CH2 domain encoding sequence may be deleted, or the hinge region may be modified to include a cysteine codon at an appropriate site. The engineered first and second polynucleotides may be expressed under suitable conditions to form the polypeptide complexes. In certain embodiments, the polypeptide complexes may reduce the simultaneous binding of antigen targets by at least 10%, 20%, 30%, 40%, 50%, 60%, 70%, 80% or 90%.

In certain embodiments, the polypeptide complexes can be used to reduce the induction of signal transduction or activation of antigen targets due to binding to a conventional antibody. In certain embodiments, the conventional antibodies or antigen-binding fragments may be engineered into a polypeptide complex provided herein, and the signal transduction or activation of the antigen target may be determined. The polypeptide complexes may be engineered using the method described above. The signal transduction or activation of the antigen target may be determined using methods described herein. The polypeptide complexes may be further engineered according to the results of the signal transduction or activation so as to better suit the purpose of reducing the induction of signal transduction or activation of antigen targets. For example modifications or mutations may be introduced at the linker sequence between the protein monomer and the antigen-binding domain, so as to adjust the steric hindrance imposed on the first and the second antigen-binding domains and thereby adjust the signal transduction or activation of the antigen target.

In certain embodiments, the present disclosure provides methods of identifying new polypeptide complexes provided herein. In certain embodiments, the methods may comprise: preparing the polypeptide complexes and screening the polypeptide complexes for desirable binding characteristics to an antigen target. The desirable binding characteristics may include, without limitation, reduced simultaneous binding of two antigen targets, and reduced signal transduction or activation of the antigen targets. In certain embodiments, conventional antibodies binding to the same antigen targets may be used as a control for determination of reduction in simultaneous binding or signal transduction or activation of antigen targets.

In certain embodiments, the methods may comprise: identifying a new antigen-binding domain, preparing a new polypeptide complex containing the antigen-binding domain and determining the binding characteristics of the polypeptide complex to the antigen target. The new antigen-binding domain may be identified using suitable methods known in the art, such as for example, phage display (O'Brien, P. M. et al, Antibody phage display: methods and protocols, Published by Humana Press, 2002), yeast display (Boder, E. T. et al, Nature Biotechnology, 15: 553-557), hybridoma technology (Kohler, G. et al, Nature, 256: 495-497 (1975)), yeast two hybrid system (MacDonald, P., Two-hybrid systems: methods and protocols, Published by Humana Press, 2001). Briefly, for identification of new antigen-binding domain using phage display, cDNAs encoding for the antigen-binding fragments are amplified from B cells by PCR and assembled into phagemid vectors which are introduced into *E. Coli*, and after rescue with helper phage, a combinatorial library of antigen-binding fragments is displayed on phage and can be used in selection for identification of a new antigen-binding domain. Briefly, for identification of new antigen-binding domain using yeast two hybrid system, the coding gene for the antigen target is cloned as an in-frame fusion to the DNA-binding domain (DBD) in a first plasmid, and the coding gene for a library of proteins (i.e. proteins to be screened) is cloned as an in-frame fusion to the transcription activation domain (AD), the two plasmids are introduced to a suitable yeast strain to allow co-expression of the two fusion proteins, and if the protein to be screened binds to the antigen target, a reporter gene will be activated and thus generate a phenotypic signal.

After identifying the appropriate antigen-binding domains, suitable protein monomers may be selected and fused to the N-terminal of the antigen-binding domain to form the polypeptide complex. If needed, a peptide linker may be introduced between the antigen-binding domain and the protein monomer and optionally disulfide bonding may be introduced between the peptide linkers. The polypeptide complexes may be expressed and purified using the methods provided herein and the binding characteristics of the polypeptide complexes may be determined using appropriate binding assays or functional assays, as illustrated elsewhere in the present disclosure.

The following examples are provided to better illustrate the claimed invention and are not to be interpreted as limiting the scope of the invention. All specific compositions, materials, and methods described below, are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLE 1

Introduction of DISCObody

A novel polypeptide complex architecture is generated, which contains two identical binding domains with the same specificity, and does not lead to target activation. It differentiates from conventional bivalent IgG or other bivalent antibody modalities where activation of certain types of receptors often occurs upon binding (see FIG. 1). This functional monovalency is achieved by a novel strategy using disulfide bond constrained space to render either the simultaneous occupation of the two antigen binding sites on a given antibody difficult or the simultaneously bound target molecules out of positions necessary for activation. We call this type of antibody as DISCObody (DISulfide COnstrained antiBODY) (see FIG. 2). The target binding domains in monospecific DISCObody can be single chain Fv (scFv), Fab and any binders derived from alternative scaffolds (see FIG. 3 and FIG. 4). DISCObody can be used as a template to make fusion proteins to generate bi-specific, tri-specific, or tetra-specific or other multispecific molecules. DISCObody fusion partners can be scFv, VH or VL single variable domain binders, peptides, or other binders derived from alternative scaffolds such as Fn3, camelid VHH.

The structure of DISCObody provides advantages with respect to the versatility of functionalities, suitability as therapeutic agents, product stability and manufacturability. In one aspect, a DISCObody provides specific binding regions that are close in space and restricted in spatial orientations due to the constraints induced by disulfide bonds. In another aspect, the two antigen binding sites may not be occupied by some antigens (especially antigens with large size) simultaneously due to steric hindrance. In another aspect, if simultaneous binding do occur, the restricted spatial orientation of the bound targets is locked into a non-activating arrangement, therefore does not cause receptor activation. In yet another aspect, the DISCObody modality lack or at least have significantly reduced FcγR binding and therefore do not crosslink cell surface receptors. These properties are necessary for better efficacy as opposed to other antibody formats when agonistic activity is deleterious to the overall drug efficacy.

Because the hinge sequence including the disulfide bonds N-terminus of the Fc structure in this novel modality is deleted, the FcγR binding of the DISCObody is greatly reduced. Therefore the DISCObody based on this modality do not cross link cell surface receptors and activate them.

In one aspect, the Fc structure in one version of the DISCObody provides a convenience for protein purification using protein A or protein G chromatography.

In another aspect, the Fc structure in one version of the DISCObody modality renders the protein with long serum half life because the antibody interaction with the neonatal receptor (FcRn) should be intact as a regular IgG.

Depending on therapeutic applications, long serum half life of a drug may not be always desirable. On the contrary, medium range of half life (1-2 days) may be preferred. Deletion of CH2 in this modality which eliminates the FcRn binding property can shorten the serum half life. Because of the size of the molecule is significantly greater than the renal filtration size around 60 kD, the half life can be around 1-2 days.

The modular structure of this novel modality provides great flexibility to make wide variety of the DISCObodies with single specificity (see FIG. 5), bi-specificity, or multi-specificity (see FIG. 6, FIG. 7 and FIG. 8) by fusion of additional antibody or non-antibody based binding fragments. In one aspect, monospecific DISCObodies against TNF receptors and super family members (CD40, DR3 etc) as well as cMet serve as efficient antagonistic agents for disease treatment. An anti-CD3 DISCObody also have wide range of clinical applications, such as allograft transplantation, type I diabetes, multiple sclerosis, and other autoimmune disease diseases. anti-CD3 DISCObody also have favorable side effect profiles compared to anti-CD3 antibodies currently in clinical trials because DISCObody is less likely to have CD3 partial activation due to monovalent-like binding mode and much reduced FcγR binding. For example, patients treated with the second generation anti-CD3 antibodies, OKT3 1 Ala-All and ChAglyCD3, still experience severe cytokine storm related side effects. Lymphopenia is also observed during treatment that is mostly the result of redistribution and marginalization of T cells (due to partial activation of T cells). Current anti-CD3 antibodies also induce Epstein-Barr virus (EBV) reactivation in majority of the patients in type I diabetes trials. Although the underlying reason for EBV reactivation is ill-defined and requires further research, there is direct evidence to suggest early immune activation may play a role.

In order to better predict the potential side effects of anti-CD3 antibody treatment in human, cross reactive antibodies towards non human primates are extremely valuable because thorough toxicological studies can be done in monkeys. However, current anti-CD3 antibodies used in clinics and tested in clinical trials lack this cross reactivity. To overcome this problem, generation of monkey CD3 cross reactive antibodies for the purpose of drug development was recently described. In fact, the first monkey cross reactive anti-human CD3 antibody was generated more than two decades ago by Professor Terhorst's group at the Massachusetts General Hospital (Pessano, EMBO J. (1985) 4:337-344; Alarcon, EMBO J. (1991) 10:903-12). The described antibody, SP34, recognizes denatured CD3 as well as native CD3 on cell surface. SP34 is T cell mitogenic when cross linked. Therefore SP34 antibody should be suitable for drug development in monospecific and multispecific DISCObody formats. However, because the sequence of the SP34 clone was not known, the recombinant production of SP34 antibody or derivatives of SP34 antibody is not yet impossible. A potential solution to obtain the sequence information is to de novo sequence the SP34 antibody using automated N-terminal sequencing via Edman degradation and mass spectroscopy technology (Bandeira, Nat. Biotech. (2008) 26:1336-1338).

In yet another aspect, this modality is valuable to make bispecific or multispecific DISCObodies where the first target binding does not lead to activation. For example, this modality is particularly suitable for making bispecific DISCObodies to CD3 ($1^{st}$ specificity) and tumor cell surface antigen ($2^{nd}$ binding specificity). In this case bispecific DISCObody do not activate T cells upon binding to CD3 alone. T cells are activated only after the bispecific DISCObody simultaneously binds to CD3 and tumor cell surface target resulting in the cross-linking of the CD3 by the tumor cells. Activation of T cells in the vicinity (and only) of cancer cells significantly enhances the tumor killing efficiency of T cells and avoid the side effects due to cytokine storm.

In another aspect, replacing the CD3 binding arm in CD3/cancer cell antigen bispecific DISCObodies by FcγR specific binders is generated to induce FcγR expressing immune cell mediated killing of tumor cells.

In another aspect, replacing the CD3 binding arm in CD3/cancer cell antigen bispecific DISCObodies by NKG2D specific binders is generated to induce NK cell mediated killing of tumor cells.

In another aspect, trispecific or even tetra specific DISCObodies is generated based on this modality with one binding specificity to CD3 or FcγR or NKG2D and the other two binding specificities to cancer cell targets. The cancer cell targets can be simultaneously present on the same cancer cells. In this case, when low or medium affinity binding are engineered, the DISCObodies selectively bind to cancer cells while the binding to normal cells expressing single target should be low. This strategy provides advantages to selectively target T cells to cancer cells and to spare the normal cells. Cancer cell targets recognized by a multispecific DISCObody can be expressed by different types of cancers. In this case, multispecific antibody drug can be used for treating broad range of cancers as long as at least one of the cancer targets is present on cell surface.

EXAMPLE 2

Construction of Plasmids

In this example, plasmids were constructed for expression of a monospecific DISCObody targeting CD3 and of a bi-specific DISCObody targeting both CD3 and EpCAM. The coding sequences for anti-CD3 antibody were based on sequences for antibody OKT3, which were obtained from published literature (see, Yoshida et al, Blood, 101:2300 (2003)). The coding sequences for anti-EpCAM antibody were based on the sequences for M79 scFv, which were obtained from published literature (see, e.g., Gottlinger et al, Int J Cancer, 38:47 (1986)).

Construction of pCR-TA-M79 scFv Vector

The M79 gene was assembled in two steps. First, 10 oligonucleotides (SEQ ID NOs: 1-10) as listed in Table 1 were synthesized. An equal molar mixture of the 10 oligonucleotides was added to a PCR reaction mixture, and the sequence encoding for the N-terminal of M79 was assembled using Taq polymerase for 30 cycles of PCR reaction. Second, another 10 oligonucleotides (SEQ ID NOs: 11-20) as listed in Table 1 were synthesized. An equal molar mixture of the 10 oligonucleotides was added to a PCR reaction mixture, and the sequence encoding for the C-terminal of M79 was assembled using Taq polymerase for 30 cycles of PCR reaction.

The PCR products obtained from the first and second step were gel purified, and 200 ng of each PCR product were added to a PCR reaction mixture with Taq polymerase, and 7 cycles of PCR reactions were performed. SEQ ID NOs: 21 and 22 (see Table 1) were subsequently added to the PCR reaction mixture, followed by 30 additional cycles of PCR reactions, to obtain the M79 gene.

The final PCR product for the M79 gene was clone into a pCR-TA vector (Invitrogen) to obtain pCR-TA-M79 scFv vector. The M79 scFv gene was verified by DNA sequencing.

TABLE 1

| SEQ ID No. | Primer type | Sequence (5'-3') |
|---|---|---|
| 1 | Forward | gaagttcaacttcttgaacaatctggtgctgaacttg ctcgtcctggtgcttc |
| 2 | Reverse | gtataaccagaagctttacaagaaagtttaacagaag caccaggacgagcaaG |
| 3 | Forward | Gtaaagcttctggttatacttttactaattatggtct ttcttgggttaaacaacgt |
| 4 | Reverse | ggataaacttcaccaatccattcaagaacttgaccag gacgttgtttaacccaagaaaG |
| 5 | Forward | Ggattggtgaagtttatcctcgtattggtaatgctta ttataatgaaaaatttaaagg |
| 6 | Reverse | gaagaagatttatcagcagtaagagtagctttaccttt aaattttcattataataaG |
| 7 | Forward | Ctgctgataaatcttcttctactgcttctatggaact tcgttctcttacttctg |
| 8 | Reverse | gaaccacgacgagcacaaaaataaacagcagaatctt cagaagtaagagaacgaaG |
| 9 | Forward | Ttttgtgctcgtcgtggttcttatgatactaattatg attggtattttgatgtttggg |
| 10 | Reverse | gccaccgccaccagaagaaacagtaacagtagtacct tgaccccaaacatcaaaataC |
| 11 | Forward | Gtttcttctggtggcggtggcagcggcggtggtgggt ccggtggcggcggatctgaac |
| 12 | Reverse | gagaaacaggaagagaaagaggagtttgagtcataac aagttcagatccgccgccaC |
| 13 | Forward | Cttctcttcctgtttctcttggtgatcaagcttcta tttcttgtcgttcttctcaatc |
| 14 | Reverse | ccaatgaagataagtattaccattagaatgaacaaga gattgagaagaacgacaaG |
| 15 | Forward | Gtaatacttatcttcattggtatcttcaaaaacctgg tcaatctcctaaacttc |
| 16 | Reverse | caggaacaccagaaaaacgattagaaactttataaat aagaagtttaggagattgaC |
| 17 | Forward | Gttttctggtgttcctgatcgttttctggttctgg ttctggtactgattttactc |
| 18 | Reverse | caccaagatcttcagcttcaacacgagaaattttaag agtaaaatcagtaccaG |
| 19 | Forward | Gaagctgaagatcttggtgtttattttgttctcaat ctactcatgttccttatac |
| 20 | Reverse | Tttcaagtttagtaccaccaccaaaagtataaggaac atgagtag |
| 21 | Forward | gaagttcaacttcttgaacaatc |
| 22 | Reverse | caaaagtataaggaacatgagtag |

Construction of pCR-TA-OKT3VH Vector

To obtain the VH gene of antibody OKT3 (OKT3 VH), 10 oligonucleotides (SEQ ID NOs: 23-32) as listed in Table 2 were synthesized. An equal molar mixture of the 10 oligonucleotides was added to a PCR reaction mixture, and OKT3 VH was assembled using Taq polymerase for 7 cycles of PCR reaction.

The assembled OKT3 VH was amplified using end primers: SEQ ID NO 33 and SEQ ID NO 34 (see Table 2), for additional 30 cycles of PCR reaction. The final OKT3VH PCR product was cloned into a pCR-TA cloning vector (Invitrogen), to obtain the pCR-TA-OKT3VH vector. The OKT3 VH gene was verified by DNA sequencing.

TABLE 2

| SEQ ID No. | Primer type | Sequence (5'-3') |
|---|---|---|
| 23 | Forward | gagaCgtacgcaggtccagctgcagcagtctgggc tgaactggcaagacctggggcctc |
| 24 | Reverse | cctagtaaaggtgtagccagaagccttgcaggacat cttcactgagggcccaggtcttG |
| 25 | Forward | Ctggctacacctttactaggtacacgatgcactggg taaaacagaggcctggacaggg |
| 26 | Reverse | ccacggctaggattaatgtatccaatccattccaga ccctgtccaggcctctgttttaC |
| 27 | Forward | Cattaatcctagccgtggttatactaattacaatca gaagttcaaggacaaggccac |
| 28 | Reverse | gttgcatgtaggctgtgctggaggatttgtctgtag tcaatgtggccttgtccttgaaC |
| 29 | Forward | Cagcacagcctacatgcaactgagcagcctgacatc tgaggactctgcagtctattac |
| 30 | Reverse | gtagtcaaggcagtaatgatcatcataatatcttgc acagtaatagactgcagagtcC |
| 31 | Forward | Gatcattactgccttgactactggggccaaggcacc actctcacagtctcctcagc |
| 32 | Reverse | Gagagctagctgaggagactgtgaga |
| 33 | Forward | gagaCgtacgcaggtccagc |
| 34 | Reverse | gctgaggagactgtgaga |

Construction of pCR-TA-OKT3 VL Vector

To obtain the VL gene of antibody OKT3 (OKT3 VL), 8 oligonucleotides (SEQ ID NOs: 35-42) as listed in Table 3 were synthesized. An equal molar mixture of the 8 oligonucleotides was added to a PCR reaction mixture, and OKT3 VL was assembled using Taq polymerase for 7 cycles of PCR reaction.

The assembled OKT3 VL was amplified using end primers SEQ ID NOs 43-44 (see Table 3) for additional 30 cycles of PCR reaction. The final OKT3VL PCR product was cloned into a pCR-TA cloning vector, to obtain pCR-TA-OKT3VL vector. The OKT3 VL gene was verified by DNA sequencing.

TABLE 3

| SEQ ID No. | Primer type | Sequence (5'-3') |
|---|---|---|
| 35 | Forward | Caaattgttctcacccagtctccagcaatcatgtctgcatctccaggggagaaggtc |
| 36 | Reverse | catgtaacttacacttgagctggcactgcaggtcatggtgaccttctccctggagatG |
| 37 | Forward | Gctcaagtgtaagttacatgaactggtaccagcagaagtcaggcacctcccccaaaag |
| 38 | Reverse | gactccagaagccagtttggatgtgtcataaatccatcttttgggggaggtgcctgaC |
| 39 | Forward | Caaactggcttctggagtccctgctcacttcagggggcagtgggtctggacctcttac |
| 40 | Reverse | gtggcagcatcttcagcctccatgccgctgattgtgagagtaagaggtcccagacC |
| 41 | Forward | Gaggctgaagatgctgccacttattactgccagcagtggagtagtaacccattcacg |
| 42 | Reverse | gagacgtacggtttatttccaactttgtccccgagccgaacgtgaatgggttactactc |
| 43 | Forward | Caaattgttctcacccagtc |
| 44 | Reverse | cgtgaatgggttactactc |

Construction of pCR-TA-CH1CH2CH3 Vector and pCR-TA-Ck Vector

Human PBMCs (peripheral blood mononuclear cells) were isolated from Ficoll gradient protocol. Total RNA of the isolated human PBMCs was prepared using RNA isolation kit (Qiagen). First strand cDNA was generated using oligo dT primer using SuperScript™ III First-Strand Synthesis SuperMix kit (Invitrogen).

Human CH1CH2CH3 gene of IgG1 was amplified from the first strand cDNA by PCR using SEQ ID NOs: 45-46 (see Table 4) as end primers, with Taq polymerase and 30 cycles of PCR reaction. The final CH1CH2CH3 PCR product was cloned into a pCR-TA cloning vector (Invitrogen), to obtain pCR-TA-CH1CH2CH3 vector. The CH1 CH2CH3 gene was verified by DNA sequencing.

Human Ck gene was amplified from the first strand cDNA by PCR using SEQ ID NOs: 47-48 (see Table 4), with Taq polymerase and 30 cycles of PCR reaction. The final Ck PCR product was cloned into a pCR-TA cloning vector (Invitrogen), to obtain pCR-TA-Ck vector. The Ck gene was verified by DNA sequencing.

TABLE 4

| SEQ ID No. | Primer type | Sequence (5'-3') |
|---|---|---|
| 45 | Forward | gctAgcaccaagggcccatccg |
| 46 | Reverse | Tttccccggagacagggag |

TABLE 4-continued

| SEQ ID No. | Primer type | Sequence (5'-3') |
|---|---|---|
| 47 | Forward | Cgtacggtggctgcaccatctgtcttcatc |
| 48 | Reverse | acactctcccctgttgaagc |

Construction of pCR-TA-Hinge-OKT3 VH—CH1 Vector

The Hinge-OKT3 VH gene was obtained by amplifying the OKT3 VH gene from the pCR-TA-OKT3VH vector by PCR using SEQ ID NOs: 49-50 (see Table 5) as primers. Partial coding sequence for the hinge sequence was introduced by the primers through PCR reaction. The amino acid sequence of the partial hinge sequence is ThrHisThrCysProProCysProAlaPro (SEQ ID NO: 69).

The PCR reaction was performed with Taq polymerase for 30 cycles. The CH1 gene was amplified from the pCR-TA-CH1 CH2CH3 vector by PCR using SEQ ID NOs: 45 and 51 (see Table 5), with Taq polymerase for 30 cycles of PCR reaction.

The above two PCR products were gel purified, and were used for assembling the Hinge-OKT3VH—CH1 gene by PCR. Briefly, 200 ng of each PCR product was added to a PCR reaction mixture with Taq polymerase, and 7 cycles of PCR reactions were performed. SEQ ID NOs: 49 and 51 were subsequently added to the PCR reaction mixture, followed by 30 additional cycles of PCR reactions.

The final Hinge-OKT3VH—CH1 PCR product was cloned into pCR-TA vector to obtain the pCR-TA-Hinge-OKT3VH—CH1 vector. The Hinge-OKT3VH—CH1 gene was verified by DNA sequencing.

TABLE 5

| SEQ ID No. | Primer type | Sequence (5'-3') |
|---|---|---|
| 49 | Forward | actcacacatgcccaccgtgcccagcaCcacgtacgcaggtccagctgcagcagtc |
| 50 | Reverse | gatgggcccttggtgctagctgaggagactgtgagagtgg |
| 45 | Forward | gctAgcaccaagggcccatccg |
| 51 | Reverse | Gagaggatcctcaagttttgtcacaagatttgggctc |

Construction of pTT5-VH3leader-CH2CH3-Hinge-OKT3 VH—CH1 Vector

VH3leader-CH2CH3-hinge gene was obtained by a two-step PCR reaction. Briefly, in the first PCR reaction, a VH3 leader sequence was attached to 5' end of the CH2CH3 gene, using SEQ ID NOs: 52 and 54 (see Table 6) as primers and pCR-TA-CH1CH2CH3 vector as the PCR template. In the second PCR reaction, a partial hinge sequence was attached to the 3' end of VH3leader-CH2CH3 sequence by using SEQ ID NOs: 53-54 (see Table 6) as primers and the PCR product of the first PCR reaction as the template. The VH3leader-CH2CH3-hinge gene was obtained from the PCR product of the second PCR reaction.

The hinge-OKT3VH—CH1 gene was amplified from pCR-TA-hinge-OKT3VH—CH1 vector using SEQ ID NOs: 49 and 51 (see Table 5) as primers, with Taq polymerase for 30 cycles of PCR reaction.

The VH3leader-CH2CH3-hinge and hinge-OKT3VH—CH1 PCR fragments are spliced together to generate VH3leader-CH2CH3-hinge-OKT3-CH1 gene with restriction overhang sequence at both ends (EcoRI and BamHI). Briefly, the PCR product of VH3leader-CH2CH3-hinge gene and the PCR product of the hinge-OKT3VH—CH1 gene were gel purified, and added to a PCR reaction mixture with Taq polymerase, followed by additional PCR reactions to amplify the VH3leader-CH2CH3-hinge-OKT3-CH1 gene.

The PCR product of the VH3leader-CH2CH3-hinge-OKT3-CH1 gene was digested by EcoRI and BamHI restriction enzymes, and then ligated with pTT5 vector (obtained from National Research Council Canada) linearized to have matching restriction ends, to produce the pTT5-VH3leader-CH2CH3-Hinge-OKT3 VH—CH1 vector.

TABLE 6

| SEQ ID No. | Primer type | Sequence (5'-3') |
|---|---|---|
| 52 | Forward | cttttcttgtggctattttaaaaggtgtccagtgt gggggaccgtcagtcttcc |
| 53 | Forward | Gccaccggatccatggagtttgggctgagctggctt tttcttgtggctatttaaaag |
| 54 | Reverse | Cggtgggcatgtgtgagttttccccggagacaggga gagg |

Construction of pTT5-VH3leader-M79scFv-CH2CH3-Hinge-OKT3 VH—CH1

VH3leader-M79scFv-CH2 was obtained by a two-step PCR reaction, in which VH3leader sequence and a short CH2 N-terminal coding sequence were appended to the M79scFv gene at its N- and C-terminal coding sequence, respectively. Briefly, the M79scFv gene was amplified by PCR reaction using SEQ ID NO: 55 and 56 as primers and pCR-TA-M79scFv vector as template. The obtained PCR product was subsequently amplified using SEQ ID NOs: 53 and 56 (see Table 7) as primers.

The CH2CH3-Hinge-OKT3 VH—CH1 gene was amplified from the pTT5-VH3leader-CH2CH3-Hinge-OKT3 VH—CH1 vector by PCR, using SEQ ID NOs: 57 and 51 as primers.

The PCR products for VH3leader-M79scFv-CH2 and for CH2CH3-Hinge-OKT3 VH—CH1 gene were gel purified, and 200 ng of each PCR product were added to a PCR reaction mixture with Taq polymerase, and 7 cycles of PCR reactions were performed. SEQ ID NOs: 53 and 51 (see Table 7) were subsequently added to the PCR reaction mixture, followed by 30 additional cycles of PCR reactions, to obtain the VH3leader-M79scFv-CH2CH3-Hinge-OKT3 VH—CH1 gene.

The obtained PCR product for VH3leader-M79scFv-CH2CH3-Hinge-OKT3 VH—CH1 gene was digested with EcoRI and BamHI and cloned into pTT5 linearized using same restriction enzymes, to generate pTT5-VH3leader-M79scFv-CH2CH3-Hinge-OKT3 VH—CH1 vector.

TABLE 7

| SEQ ID No. | Primer type | Sequence (5'-3') |
|---|---|---|
| 55 | Forward | cttttcttgtggctattttaaaaggtgtccagtgt gaagttcaacttcttgaacaatc |

TABLE 7-continued

| SEQ ID No. | Primer type | Sequence (5'-3') |
|---|---|---|
| 53 | Forward | Gccaccggatccatggagtttgggctgagctggctt tttcttgtggctatttaaaag |
| 56 | Reverse | Gaggaagactgacggtcccccttaatttcaagttt agtac |
| 57 | Forward | Gtactaaacttgaaattaaaggggaccgtcagtct tcctc |
| 51 | Reverse | Gaga ggatcc tcaagttttgtcacaagatttggg ctc |

Construction of pTT5-VH3leader-OKT3VL-Ck

VH3leader-OKT3VL-Ck was obtained by a two-step PCR reaction. First, the OKT3VL gene was amplified by PCR reaction using SEQ ID NO: 58 and 59 as primers and pCR-TA-OKTVL vector as template. The obtained PCR product was subsequently amplified using SEQ ID NOs: 53 and 59 (see Table 8) as primers, such that a VH3 leader sequence was appended to the coding sequence of the N-termini of OKT3VL.

Second, human Ck gene was amplified from the pCR-TA-huCk vector by PCR, using SEQ ID NOs: 60-61 as primers.

The PCR products obtained from the first and second step were gel purified, and 200 ng of each PCR product were added to a PCR reaction mixture with Taq polymerase, and 7 cycles of PCR reactions were performed. SEQ ID NOs: 53 and 61 (see Table 8) were subsequently added to the PCR reaction mixture, followed by 30 additional cycles of PCR reactions, to obtain the VH3leader-OKT3VL-Ck gene.

The obtained PCR product for VH3leader-OKT3VL-Ck gene was digested with EcoRI and BamHI and cloned into pTT5 linearized using EcoRI and BamHI, to generate pTT5-VH3leader-OKTVL-huCk vector.

TABLE 8

| SEQ ID No. | Primer type | Sequence (5'-3') |
|---|---|---|
| 58 | Forward | cttttcttgtggctattttaaaaggtgtccagtgt caaattgttctcacccagtc |
| 53 | Forward | Gccaccggatccatggagtttgggctgagctggctt tttcttgtggctatttaaaag |
| 59 | Reverse | gatggtgcagccaccgtacggtttatttccaacttt gtc |
| 60 | Forward | gacaaagttggaaataaaccgtacggtggctgcacc atc |
| 61 | Reverse | Gaga ggatcc acactctcccctgttgaagc |

EXAMPLE 3

Expression of Monospecific DISCObody Targeting CD3 and Bi-Specific DISCObody Targeting Both CD3 and EpCAM For expression of monospecific DISCObody targeting CD3 (anti-CD3 DISCObody), the pTT5-VH3leader-CH2CH3-Hinge-OKT3 VH—CH1 vector and the pTT5-

VH3leader-OKTVL-huCk vector were co-transfected into HEK293-6E (obtained from National research council of Canada) cells using cationic polymer polyethylenimine (PEI) as previously described by Durocher et al. (see, Durocher et al., Nucleic Acid Res 2002, 30: e9).

For expression of bi-specific DISCObody targeting both CD3 and EpCAM (anti-EpCAM/CD3 DISCObody), the pTT5-VH3leader-M79scFv-CH2CH3-Hinge-OKT3 VH—CH1 vector and the pTT5-VH3leader-OKTVL-huCk vector were co-transfected into HEK293-6E cells using PEI as previously described by Durocher et al. (see, Durocher et al., Nucleic Acid Res 2002, 30: e9).

Figure 9:
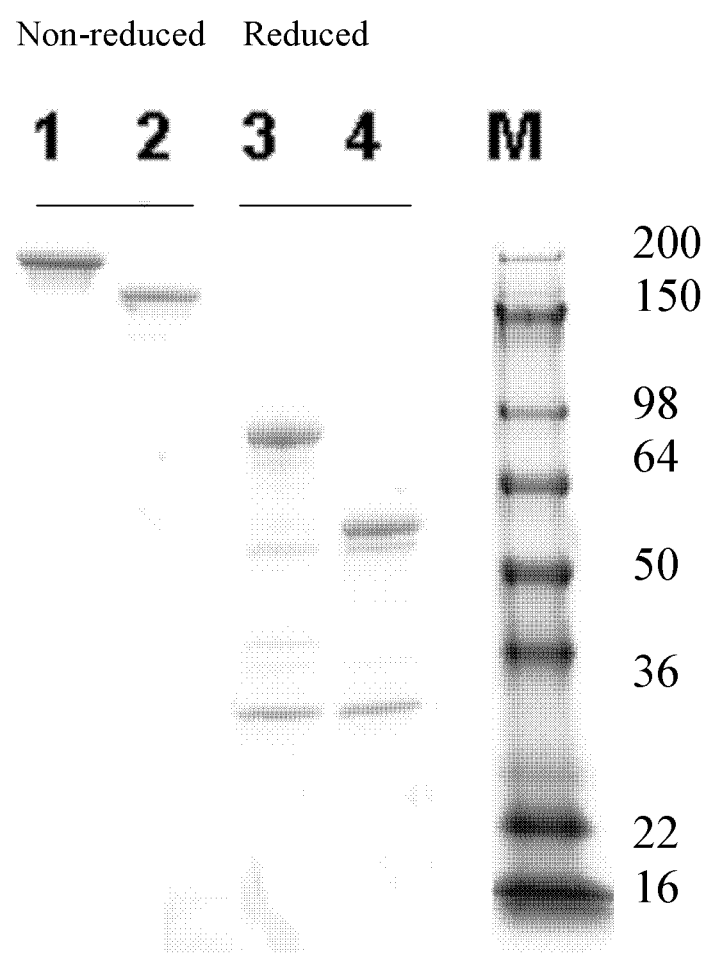
FIG. 9 shows the reduced and non-reduced SDS-PAGE electrophoresis image of the anti-CD3 DISCObody and the anti-EpCAM/CD3 DISCObody.

The transfected cells were cultured to allow protein expression. The supernatants of the cell cultures were collected and purified using protein A chromatography. Protein integrity and homogeneity were analyzed using SDS-PAGE and size exclusion chromatography. Briefly, the anti-CD3 DISCObody and the anti-EpCAM/CD3 DISCObody were prepared using SDS sample buffer and SDS-reducing sample buffer, and then the samples were run on 4-20% polyacrylamide gel. The gel were then stained using standard Coomassie blue dye (Pierce) and the resultant protein bands were analyzed for sizes. As shown in FIG. 9, both the anti-CD3 DISCObody and the anti-EpCAM/CD3 DISCObody were expressed in a correct molecular weight.

EXAMPLE 4

Characterization of Target Binding Activities of the DISCObodies

Binding to CD3-Experssing Jurkat Cells

Figure 10:
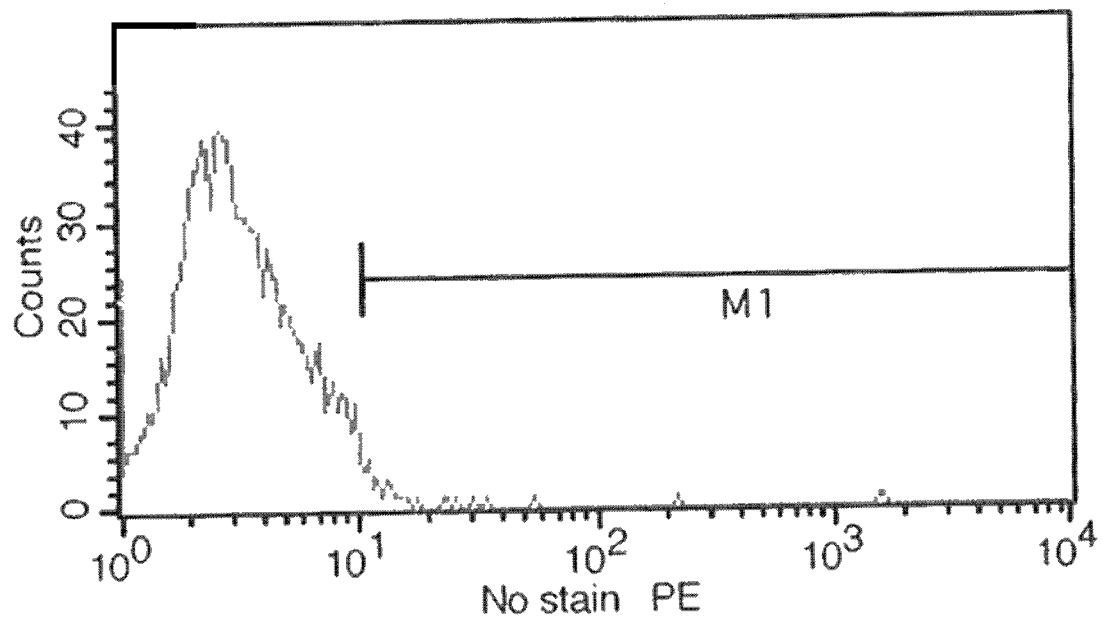
FIG. 10 shows the binding of anti-CD3 DISCObody to Jurkat cells and the binding of anti-CD3/EpCAM DISCObody to MCF-7 cells as determined by FASC analysis: (a) binding of isotype control antibody to Jurkat cells; (b) anti-CD3 DISCObody to Jurkat cells; (c) isotype control antibody to MCF-7 cells; and (d) anti-CD3/EpCAM DISCObody to MCF-7 cells.
Figure 10:
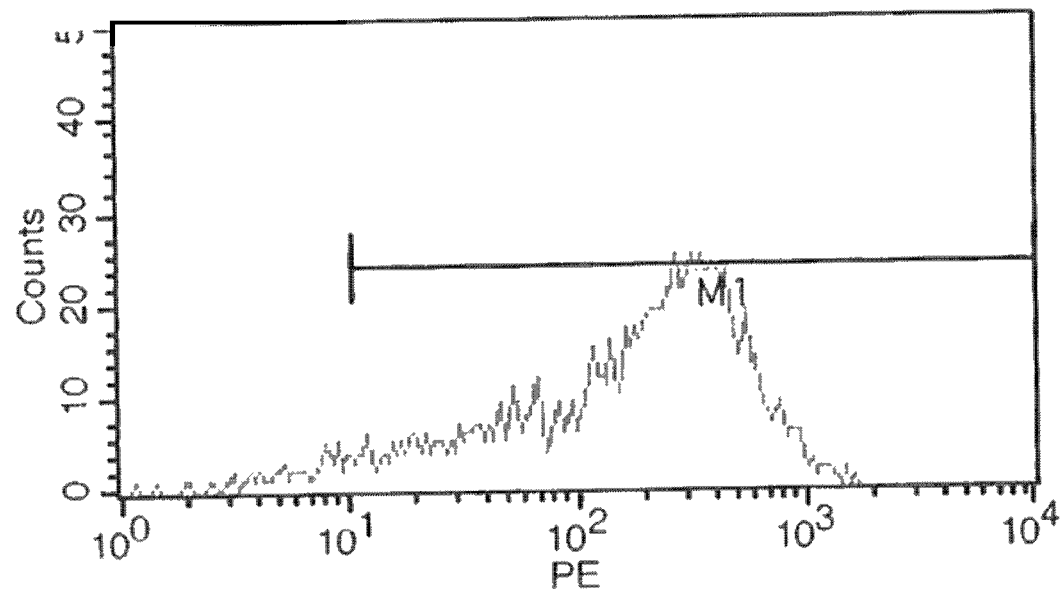
Figure 10:
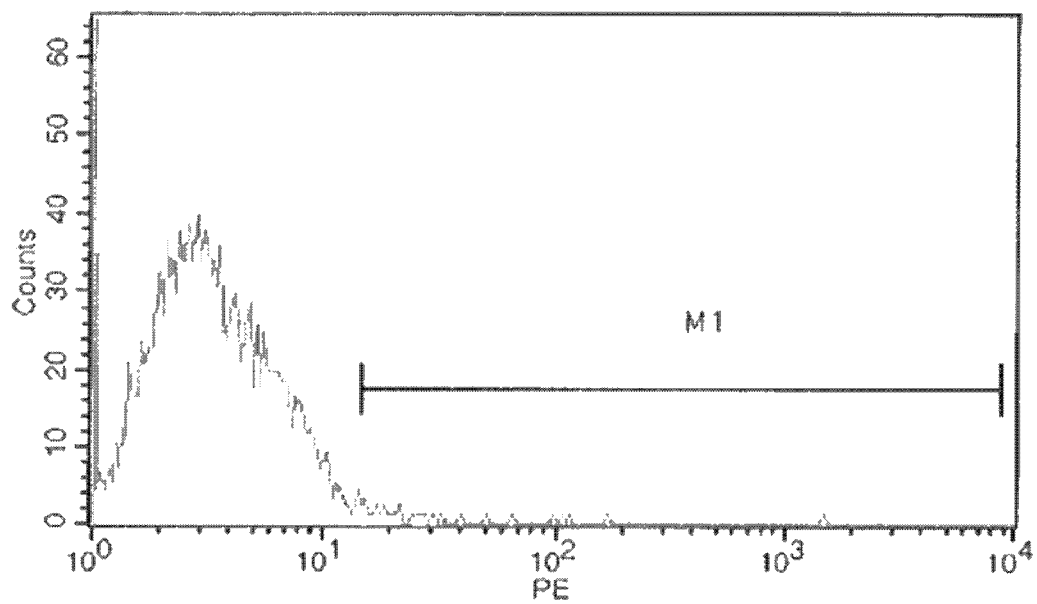
Figure 10:
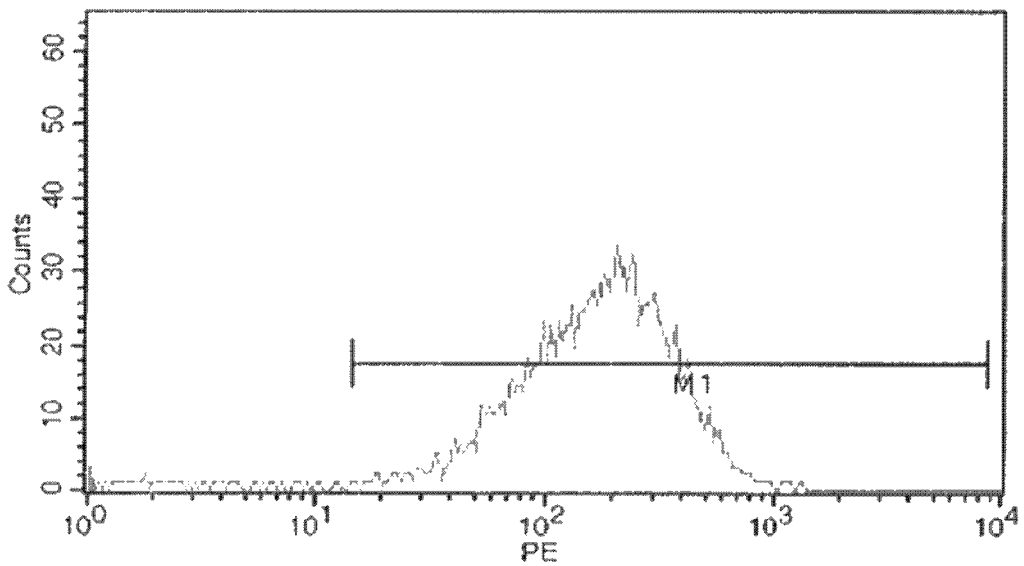

Binding of anti-CD3 DISCObody to human CD3 proteins was analyzed by FACS. Jurkat cells, which expressed human CD3 on cell surface, were obtained from American Type of Cell Culture (ATCC) and cultured according to the ATCC protocol. Before FACS analysis, Jurkat cells were incubated with anti-CD3 DISCObody first and then with anti-human Fc-PE conjugate (Southern Biotech). The treated Jurkat cells were subject to FACS analysis to determine DISCObody binding. As shown in FIGS. 10 (a) and (b), the Jurkat cells incubated with the anti-CD3 DISCObody were positive for PE staining, while the control Jurkat cells incubated with an isotype control antibody 1D6 (human antibody, against a non-relative antigen Dot1L) did not show much staining. The results indicated that the anti-CD3 DISCObody was capable of specific binding to its target CD3.

Binding to EpCAM-Experssing MCF-7 Cells

Binding of anti-EpCAM/CD3 DISCObody to human EpCAM was also analyzed by FACS. MCF-7 cell line, which is a tumor cell line expressing EpCAM on its surface, were obtained from American Type of Cell Culture (ATCC) and cultured according to the ATCC protocol. Before FACS analysis, MCF-7 cells were incubated with anti-EpCAM/CD3 DISCObody and then with anti-human Fc-PE conjugate (Southern Biotech). As shown in FIGS. 10 (c) and (d), MCF-7 cells incubated with the anti-EpCAM/CD3 DISCObody showed much stronger staining than those incubated with the isotype control antibody 1D6. The results confirmed the specific binding of the anti-EpCAM/CD3 DISCObody to its target EpCAM.

DISCObody has Reduced Binding to Human FcγR.

Anti-CD3 DISCObody and anti-EpCAM/CD3 DISCObody are tested for their binding activity to FcγR proteins. Regular human IgG1 is used as control. Two anti-CD3 antibodies engineered for minimizing binding to FcγRs are also tested in parallel as a comparison: OKT3γ1 Ala-Ala (teplizumab, humanized anti-CD3 IgG1 antibody with mutation of the hinge residues LeuLeu to AlaAla, Xu et al, Cell Immunol. (2000)200:16-26) and ChAglyCD3 (otelixizumab, humanized anti-CD3 antibody with Asn297Ala mutation, Bolt, Eur. J. Immunol. (1993) 23:403-11).

FcγR proteins are purchased from R&D systems (Minnesota, Wis.) and are immobilized on ELISA plates. Anti-CD3 DISCObody and anti-EpCAM/CD3 DISCObody are incubated with the FcγR coated plates respectively. Regular human IgG1, OKT3γ1 Ala-Ala, and ChAglyCD3 are tested in parallel. Fab'2 of goat-anti-human Fc conjugated with HRP are subsequently added and incubated. Detection is done using HRP substrate, ABTS.

The results show that deletion of hinge sequence or elimination of disulfide bonds in the hinge region reduce FcγR binding of the DISCObodies, because disulfide bound hinge followed by CH2CH3 are necessary for FcγR binding. The DISCObodies show greatly reduced binding of human FcγRs (FcγRI, II, III) compared to regular human IgG1, and significantly lower binding than OKT3γ1 Ala-Ala and ChAglyCD3.

Mono-Valent Binding of Human CD3 by Anti-CD3 DISCObody

Human CD3epsilon and gamma chain complex protein are expressed as a single chain protein in a sequence configuration of CD3epsilon-(GlyGlyGlyGlySer)$_3$-CD3gamma-histidin6 in *E. coli* expression system. CD3epsilon and CD3 gamma chain sequences are found from literature and the corresponding genes are custom synthesized (IDT oligonucleotide Technologies, San Diego, Calif.). The gene of the single chain from CD3epsilon and CD3 gamma are generated using PCR method. The *E. coli* expressed protein is purified using a standard Nichel chelating column chromatography. To test if anti-CD3 DISCObody can bind only one (not two molecules) molecule of antigen, CD3 protein is coated on an ELISA plate followed by incubation with anti-CD3 DISCObody and then with biotinylated CD3 protein again. Binding of biotinylated CD3 protein using streptavidin-HRP conjugate is detected using ABTS substrate. Results show that anti-CD3 DISCObody do not have significant binding to streptavidin-HRP conjugate of the biotinylated CD3 protein.

EXAMPLE 5

In Vitro Biological Activity of Anti-CD3 DISCObody and Anti-EpCAM/CD3 DISCObody Activation of T Cells by Anti-CD3 DISCObody and Anti-EpCAM/CD3 DISCObody The binding of a DISCObody to its target is in a functionally mono-valent way, and is non-activating to T cells. Also because the FcγR binding is greatly reduced, there is minimal effect from FcγR mediated receptor cross-linking effect when FcγR expressing cells are present with T cells.

This unique binding property of DISCObodies was verified using FACS based T cell activity assay. Anti-CD3 DISCObody and anti-EpCAM/CD3 DISCObody as prepared in Example 3 were tested for their capability of T cell activation upon after binding to their target CD3 on PBMC. Expression of CD69 was detected as a marker for early T cell activation.

Briefly, PBMCs were incubated with anti-CD3 DISCObody or anti-EpCAM/CD3 DISCObody at concentrations of 0.1 ug/ml and 1 ug/ml for 24 hours. 1D6 tested in parallel as a negative control, and hSP34 IgG2 (a humanized anti-CD3

IgG2 antibody) was used as a positive control. The PBMCs were then incubated with both FITC-conjugated anti-CD3 antibody (1:200) and PE-conjugated anti-CD69 antibody (1:200) for 1 h at 4° C. The PBMCs were washed with PBS once and re-suspended in PBS for FACS analysis.

Figure 11:
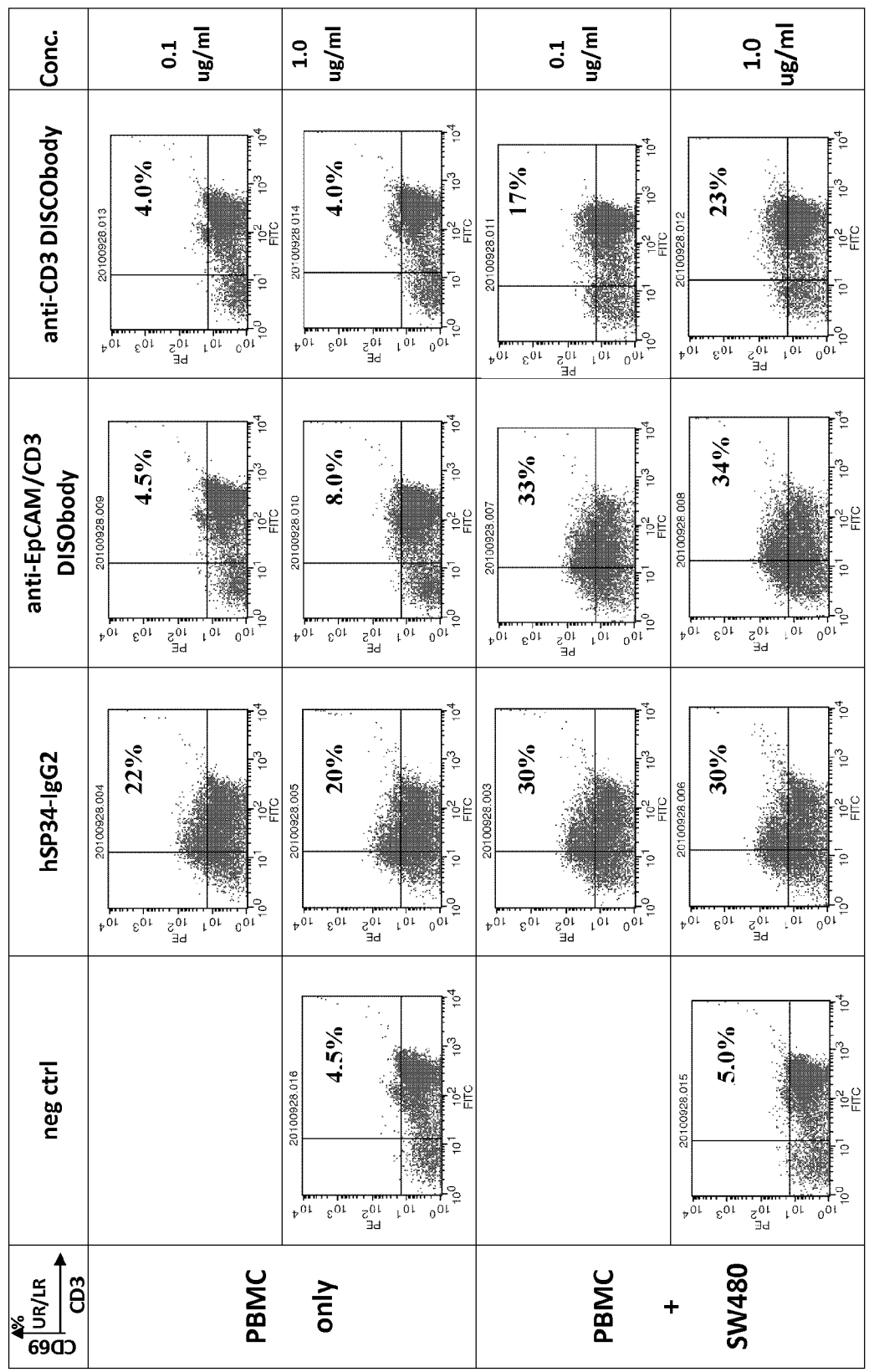
FIG. 11 shows the CD69 expression on PBMC after incubation with the anti-CD3 DISCObody or the anti-EpCAM/CD3 DISCObody, in the presence or absence of SW480 cells.

The FACS results were shown in FIG. 11 and summarized in Table 9. In each FACS result graph, the X axis indicated cells detected as positive by FITC-conjugated anti-CD3 antibody, and the Y axis indicated cells detected as positive by PE-conjugated anti-CD69 antibody. The percentages shown on the FACS results were UR/LR %, in which UR indicated cells positive for both CD3 and CD69 expression, and LR indicated cells positive for CD3 expression but negative for CD69.

gated anti-CD3 antibody and PE-conjugated anti-CD69 antibody, before FACS analysis for expression of CD3 and CD69.

As shown in FIG. 11 lower panel (PBMC+SW480) and Table 9, for positive control hSP34 IgG2, CD69-expressing PBMCs moderately increased on in the presence of SW480 cells as compared with PBMC only. However, both anti-CD3 DISCObody and anti-EpCAM/CD3 DISCObody showed at least 3-7 fold increase in CD69-expressing PBMCs in the presence of SW480 cells, which indicated tumor specific T cell activation. The T cell activation of anti-EpCAM/CD3 DISCObody in the presence of SW480 cells was even slightly better than the positive control.

TABLE 9

| Sample name | Drug and concentration | Cell combination | UR (events) | LR (events) | UR/LR (%) |
|---|---|---|---|---|---|
| NEG1 | Negative control 1 ug/ml | SW480 + PBMC | 335 | 7348 | 4.56 |
| NEG2 | Negative control 1 ug/ml | PBMC | 370 | 7456 | 4.96 |
| hSP34 IgG2-1 | hSP34 0.1 ug/ml | SW480 + PBMC | 1866 | 4266 | 43.74 |
| hSP34 IgG2-2 | hSP34 1 ug/ml | SW480 + PBMC | 1663 | 3905 | 42.59 |
| hSP34 IgG2-3 | hSP34 0.1 ug/ml | PBMC | 1389 | 5827 | 23.84 |
| hSP34 IgG2-4 | hSP34 1 ug/ml | PBMC | 1337 | 5412 | 24.70 |
| Drug1-1 | Drug1 0.1 ug/ml | SW480 + PBMC | 2075 | 3812 | 54.43 |
| Drug1-2 | Drug1 1 ug/ml | SW480 + PBMC | 1685 | 3266 | 51.59 |
| Drug1-3 | Drug1 0.1 ug/ml | PBMC | 332 | 7240 | 4.59 |
| Drug1-4 | Drug1 1 ug/ml | PBMC | 589 | 6942 | 8.48 |
| Drug2-1 | Drug2 0.1 ug/ml | SW480 + PBMC | 1082 | 6203 | 17.44 |
| Drug2-2 | Drug2 1 ug/ml | SW480 + PBMC | 1684 | 5674 | 29.68 |
| Drug2-3 | Drug2 0.1 ug/ml | PBMC | 291 | 7042 | 4.13 |
| Drug2-4 | Drug2 1 ug/ml | PBMC | 388 | 7449 | 5.21 |

NEG: negative control;
Drug 1: Anti-EpCAM/CD3 DISCObody;
Drug 2: Anti-CD3 DISCObody;
UR (events): cells positive for both CD3 and CD69 expression;
LR (events): cells positive for CD3 expression but negative for CD69.

As shown in FIG. 11 upper panel (PBMC only), PBMCs treated with the positive control hSP34 IgG2 showed significantly elevated CD69 expression as compared with the negative control, which indicated T cell activation by the positive control antibody. To the contrary, anti-CD3 DISCObody at both concentrations did not show any induced CD69 expression, and the results were comparable with that of the negative control. Anti-EpCAM/CD3 DISCObody also showed comparable results to the negative control at 0.1 ug/ml, although the CD69 expression was slightly elevated at 1 ug/ml, it was much lower than that of the positive control. These results together indicated that, the DISCObodies had no T cell activation, or the activation was greatly reduced compared to conventional CD3 antibodies.

Activation of T Cells by Anti-CD3 DISCObody and Anti-EpCAM/CD3 DISCObody in the Presence of Tumor Cells Anti-CD3 DISCObody and anti-EpCAM/CD3 DISCObody as prepared in Example 3 were further tested for their capability of T cell activation in the presence of tumor cells. PBMCs and SW480 cells (a colon cancer cell line, obtained from ATCC) were incubated with anti-CD3 DISCObody or anti-EpCAM/CD3 DISCObody at concentrations of 0.1 ug/ml and 1 ug/ml for 16-24 hours. Similarly, 1D6 was tested in parallel as a negative control, and hSP34 IgG2 was used as a positive control. The combined PBMCs and SW480 cells were then incubated with both FITC-conju-

EXAMPLE 6

In Vitro Cell Killing Activity of Anti-CD3 DISCObody and Anti-EpCAM/CD3 DISCObody Anti-CD3 DISCObody and anti-EpCAM/CD3 DISCObody as prepared in Example 3 were tested in vitro for killing cancer cells by mediating T cell activation.

SW480 cells were grown in RPMI 1640 supplemented with 10% fetal bovine serum at 37° C. in a 5% $CO_2$ humidified incubator, and then trypsinized and washed once with RPMI 1640/10% heat inactivated FCS. The SW480 cells were labeled with PKH26 dye (Sigma) according to the manufacturer's instructions. The labeled cells were washed twice with RPMI 1640/10% heat inactivated FCS.

Human PBMCs were isolated from whole blood samples of two healthy human donors according to manufacturer's instruction (GE healthcare). The purified PBMCs were re-suspended in RPMI 1640/10% heat inactivated FCS at a density of about $2 \times 10^6$/ml, and incubated at 37° C. under 5% $CO_2$ for 24 hours.

The SW480 cells and PBMC cells were collected. The SW480 cells were adjusted to a density of $4 \times 10^5$ cells/ml, and the PBMC cells were adjusted to a density of $4 \times 10^6$ cells/ml (for assay with effector cell: target cell ratio (E:T ratio) of 1:1).

The anti-CD3 DISCObody and anti-EpCAM/CD3 DISCObody were 10-fold serially diluted with RPMI 1640/10% heat inactivated FCS to 8 concentrations starting from 15 ug/ml. Anti-CD3 conventional antibody OKT3 was used as positive control, and control IgG1D6 was used as negative control. The positive controls and negative controls were also serially diluted to make the same 8 concentrations.

50 ul of 5480 cells and 50 ul of PBMCs were added per well in a 96-well round bottomed plate, and 50 ul of testing sample (anti-CD3 DISCObody or anti-EpCAM/CD3 DISCObody) or control sample (positive or negative) were added to the corresponding wells. Each concentration of a sample was performed in duplicate. The contents in the wells were gently mixed by shaking the plate by hand and then were incubated the plates at 37° C. under 5% $CO_2$ for 48 hours. Dead cells (lysed) were counted under microscope.

The results were shown in Table 10. "+" indicated positive cancer cell killing activity, and "−" indicated negative cancer cell killing activity. The more the "+", the stronger the cancer killing activity. "+/−" indicated the cancer killing activity is not significant.

TABLE 10

| Antibody Conc. (ug/ml) | Anti-EpCAM/CD3 DISCObody | Anti-CD3 DISCObody | OKT3 IgG1 | Ctrl IgG |
|---|---|---|---|---|
| 10 | +++ | +++ | +++ | − |
| 1 | +++ | + | +++ | − |
| 0.1 | +++ | − | +++ | − |
| 0.01 | +++ | − | +++ | − |
| 0.001 | +++ | − | +++ | − |
| 0.0001 | + | − | +++ | − |
| 0.00001 | − | − | +/− | − |
| 0.000001 | − | − | − | − |

As shown in Table 10, anti-EpCAM/CD3 DISCObody showed positive cancer killing activity at a concentration of 0.0001 ug/ml, and its activity at 0.001 ug/ml or higher was comparable to that of the conventional anti-CD3 antibody.

EXAMPLE 7

Inhibition of Tumor Growth by Anti-EpCAM/CD3 DISCObody in Mouse Xenograft Models 14 female NOD/SCID mice aged 4-5 weeks (obtained from Zhongshan University, China) were randomized into three groups with 5 mice in each testing group, and 4 mice in the vehicle group. Each mouse was inoculated at the right flank with 0.1 ml cell suspension containing $5 \times 10^6$ SW480 cells and $5 \times 10^6$ PBMC cells mixed with matrigel (BD Biosciences) in a ratio of 1:1.5 days after the inoculation, mice were administered with corresponding testing samples (dissolved in PBS) according the dosing regimen shown in Table 11.

TABLE 11

| Group | Animal No. | Dosing | Administration time |
|---|---|---|---|
| Vehicle | 4 | PBS, 0.1 ml/10 g, IV | Day 0-1 h, 5 days after inoculation |
| Anti-EpCAM/CD3 DISCObody | 5 | 20 ug/mouse, 0.1 ml/10 g, IV | Day 0-1 h, 5 days after inoculation |
| Anti-EpCAM/CD3 DISCObody | 5 | 100 ug/mouse, 0.1 ml/10 g, IV | Day 0-1 h, 5 days after inoculation |

The mice were observed for about two months after the last time dosing. 5 days after the last time dosing, mice were observed for development of tumor, and the number of tumor-bearing mice was counted. Results were shown in Table 12.

TABLE 12

| Group | Animal Number | Tumor Bearing Mice Number | Tumor Take Rate |
|---|---|---|---|
| PBS, 0.1 ml/10 g | 4 | 4 | 100% |
| Anti-EpCAM/CD3 DISCObody 20 ug | 5 | 2 | 40% |
| Anti-EpCAM/CD3 DISCObody 100 ug | 5 | 3 | 60% |

Figure 12:
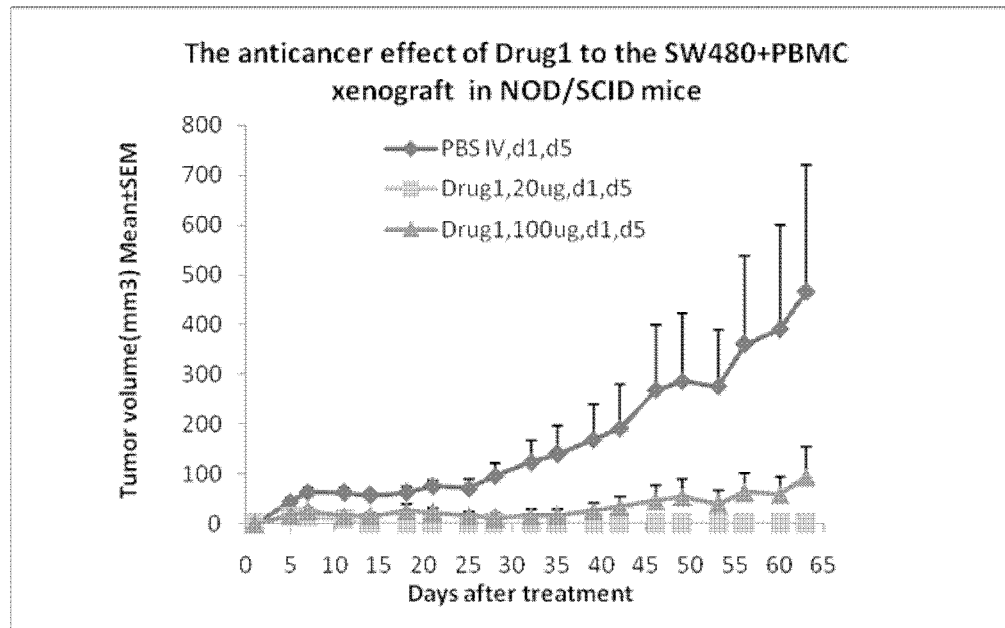
FIG. 12 shows the tumor volume (a) and the body weight (b) of the mice treated with the anti-EpCAM/CD3 DISCObody (Drug 1), as measured during the 65-day study period.
Figure 12:
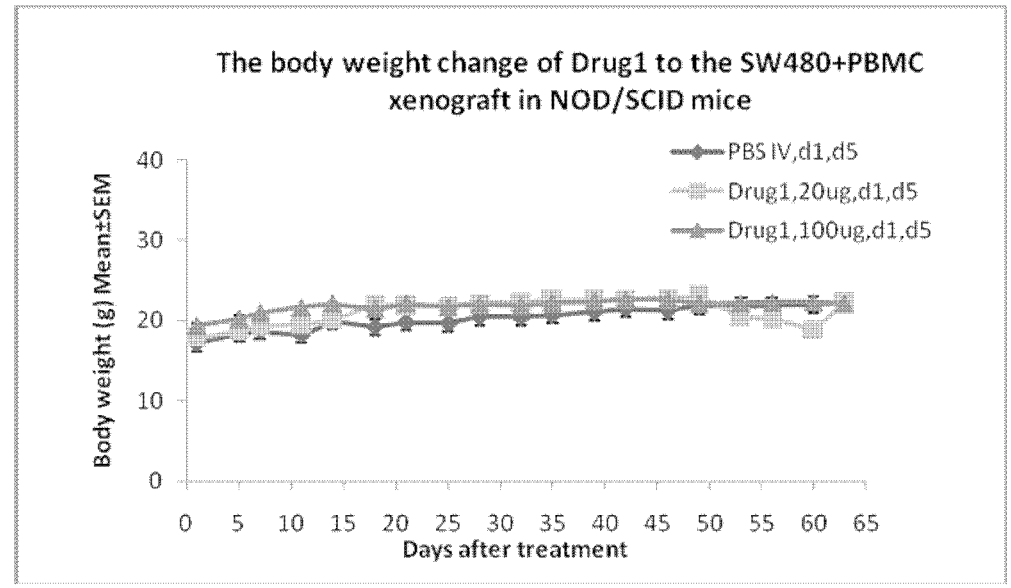

The tumor volume of the mice was measured twice a week using a caliper, and the body weight was also measured at the same interval. The results were shown in FIGS. 12 (a) and (b). The Anti-EpCAM/CD3 DISCObody at both testing concentrations effectively inhibited tumor growth, and such inhibition was statistically different from the vehicle groups (p<0.01). As shown in FIG. 12 (b), the body weight of the mice maintained on a similar level during the study.

The RTV T/C and tumor inhibition rate were also calculated, see Table 13.

TABLE 13

| Group | RTV T/C | Days after treatment | Tumor growth inhibition rate |
|---|---|---|---|
| Anti-EpCAM/CD3 DISCObody 20 ug | 0 | 18~63 | 100% |
| Anti-EpCAM/CD3 DISCObody 100 ug | 31% | 32 | 69% |

Figure 13:
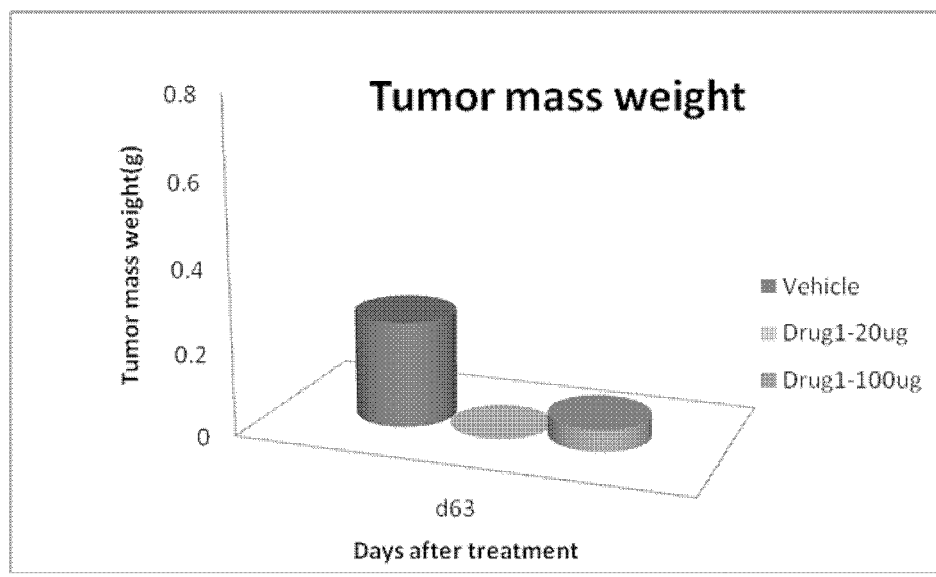
FIG. 13 shows the tumor mass weight of the mice treated with the anti-EpCAM/CD3 DISCObody (Drug 1) as measured after the study.

At the end of the study, all the tumor-bearing mice were sacrificed, and the tumor mass were collected and weighed. Results were shown in FIG. 13. The study showed that, the anti-EpCAM/CD3 DISCObody effectively inhibited tumor growth in mice.

EXAMPLE 8

Construction of Anti-CD19/CD3 DISCObody and In Vitro Biological Activity Study

Plasmids for expressing anti-CD19/CD3 DISCObody are constructed using a similar procedure described in Example 2.

Construction of pTT5-VH3leader-anti-CD19-scFv-CH2CH3-Hinge-OKT3 VH—CH1

The coding sequences for anti-CD19 scFv are based on the sequences obtained from published literature (see, U.S. patent application 20090220501). Overlapping oligonucleotides are designed based on the published sequences, and then synthesized. The overlapping oligonucleotides encoding the N-terminal of anti-CD19 scFv are mixed and assembled by Taq polymerase in a PCR reaction. The coding sequence for C-terminal of anti-CD19 scFv is also assembled in a similar way. The obtained PCR products encoding for the N- and C-terminal of anti-CD19 scFv are further mixed and assembled by PCR to obtain the full length coding sequence for anti-CD19 scFv, which is then cloned into a pCR-TA vector (Invitrogen) to obtain pCR-TA-anti-CD19 scFv vector. The anti-CD19 scFv gene was verified by DNA sequencing.

VH3leader-anti-CD19 scFv —CH2 gene is assembled by PCR, using the pCR-TA-anti-CD19 scFv vector as template, and primers containing VH3 leader sequence and partial coding sequence for CH2. The CH2CH3-Hinge-OKT3 VH—CH1 gene is amplified from the pTT5-VH3leader-CH2CH3-Hinge-OKT3 VH—CH1 vector by PCR. The two PCR products are further assembled by PCR to obtain VH3leader-anti-CD19 scFv-CH2CH3-Hinge-OKT3 VH—CH1 gene, which is subsequently cloned into linearized pTT5 vector to generate pTT5-VH3leader-anti-CD19 scFv —CH2CH3-Hinge-OKT3 VH—CH1 vector.

Construction of pTT5-VH3leader-OKT3VL-Ck pTT5-VH3leader-OKT3VL-Ck is constructed using methods described in Example 2.

Expression of DISCObody Targeting Both CD3 and CD19 pTT5-VH3leader-anti-CD19 scFv —CH2CH3-Hinge-OKT3 VH—CH1 vector and pTT5-VH3leader-OKT3VL-Ck are co-transfected into HECK 293-6E cells, and the transfected cells are cultured to allow protein expression. The CD3/CD19 DISCObody is isolated from the supernatant of the cell culture, and characterized using SDS-PAGE electrophoresis.

Characterization of Target Binding Activities

The binding of anti-CD3/CD19 DISCObody to PBMC cells and Raji cells (expressing CD19, obtained from ATCC) are characterized using FACS analysis, using the similar methods described in Example 4.

In Vitro Biological Activity of Anti-CD3/CD19 DISCObody

Anti-CD3/CD19 DISCObody is incubated with PBMCs, in the presence or absence of Raji cells. hSP34 IgG2 is used as positive control and 1D6 is used as negative control. Then the PBMCs or PBMCs/Raji cells are incubated with FITC-conjugated anti-CD3 antibody and PE-conjugated anti-CD69 antibody, before FACS analysis for expression of CD3 and CD69. When incubated in the absence of Raji cells, the anti-CD3/CD19 DISCObody do not show significantly induced CD19 expression as compared with the positive control. When incubated in the presence of Raji cells, the CD19 expression induced by the anti-CD3/CD19 DISCObody increases and is comparable to that of the positive control.

In Vitro Cancer Cell Killing Activity of Anti-CD3/CD19 DISCObody

Raji cells are cultured, trypisinzed and labeled with PKH26 dye. Human PBMCs are isolated from whole blood and re-suspended in culture medium. $2 \times 10^6$ human PBMCs with $2 \times 10^5$ Raji cells are mixed in culture medium and seeded in the wells on a 96-well plate. Serial dilutions of anti-CD3/CD19 DISCObody are added to the correspond wells and incubated at 37 C for 16-24 hours. Cytotoxicity towards cancer cells is detected by counting under microscope. The cytotoxicity of anti-CD3/CD19 DISCObody to Raji cells is comparable to that of the positive control, i.e. the conventional CD3 antibody.

EXAMPLE 9

Construction of Anti-IL6 Monospecific DISCObody and Biological Activity Study

Construction of Anti-Human IL-6 mab 240.g1 DISCObody Heavy Chain (HC) and Light Chain (LC) Gene.

The coding sequences for anti-human IL-6 mab 240.g1 DISCObody is assembled by PCR using similar methods described in Example 2. The CH2CH3-hinge part of the anti-human IL-6 DISCObody is prepared as described in Example 2. The heavy chain variable sequences of anti-human IL-6 antibody, clone 240.g1, are procured from published patent (see, e.g. WO 2007/066082, SEQ ID NO: 62). The corresponding VH gene is synthesized using PCR of overlapping oligonucleotides. The Fd gene is generated by overlapping PCR methods using VH and human IgG1CH1, which is PCR cloned form human B cell cDNA library. Anti-human IL-6 DISCObody heavy chain gene (HC) is generated by overlapping PCR method using the IgG1 CH2CH3-hing gene and the anti-human IL-6 240.g1 Fd gene. The corresponding VL sequence is also obtained from the published patent (see, e.g. WO 2007/066082, SEQ ID NO: 63) and the corresponding VL gene is synthesized using PCR of overlapping oligonucleotides. The anti-human IL-6 240.g1 LC gene can be generated by overlapping PCR method using the VL and human IgG1Ckappa gene, which can be PCR cloned from human B cell cDNA library. As a control antibody, the heavy chain gene for the anti-human IL-6 mab, clone 240.g1 is also generated in the regular human IgG1 format (see, e.g. WO 2007/066082).

Expression of Anti-Human IL-6 mab 240.g1 DISCObody.

The HC and LC expression constructs for anti-human IL-6mab 240.g1 DISCObody are generated by cloning the anti-human IL-6 mab 240.g1 DISCObody HC and LC cassettes into a mammalian expression vector, pcDNA3.1 (Invitrogen, San Diego, Calif.). Similarly, the HC cassette of anti-human IL-6 mab 240.g1 in regular IgG1 format is also cloned into the pcDNA3.1 expression vector. The pcDNA3.1-240.g1DISCObody-HC and pcDNA3.1-240.g1LC constructs are co-transfected into HEK293 cells (Invitrogen, San Diego, Calif.) according to manufacturer's instructions. The anti-IL-6 mab240.g1 DISCObody in the conditioned media is purified using standard protein-A chromatography. Similarly, the pcDNA3.1-240.g1 IgG1-HC and pcDNA3.1-240.g1 LC constructs are also transfected into HEK293 cells and the anti-human IL-6 mab 240.g1 in regular IgG1 format is also purified from conditioned media using protein-A chromatography.

In Vitro Characterization of Anti-Human IL-6 Mab240.g1 DISCObody.

Binding of anti-human IL-6 mab 240.g1 DISCObody to human IL-6. The binding affinity of anti-human IL-6 mab 240.g1 DISCObody to human IL-6 is evaluated using plate-coated recombinant human IL-6 (R&D System, USA) in standard ELISA based binding assay. The binding affinity for mab240.g1 in monomeric DISCObody format to human IL-6 is lower compared to the binding affinity of mab240.g1 in bivalent IgG1 format.

Blocking of human IL-6 binding to human IL-6R on human DS-1 cell surface. The neutralization activity of anti-human IL-6 mab240.g1 DISCObody is determined by blocking human IL-6 binding to human DS-1 cell surface. Human DS-1 cells are dependent on IL-6 for growth (ATCC, USA). DS-1 cells are cultured in RPMI 1640 medium with 2 mM L-glutamine adjusted to contain 1.5 g/L sodium bicarbonate, 4.5 g/L glucose, 10 mM HEPES, and 1.0 mM sodium pyruvate supplemented with 10 U/ml IL-6 and 10% fetal bovine serum. Recombinant human IL-6 is labeled with biotin using standard protein biotinylation kit (Pierce, USA).

Binding of human IL-6 to DS-1 cell surface and blocking of human IL-6 binding to DS-1 cells are evaluated using standard flow cytometry analysis protocols. Briefly, DS-1 cells are resuspended in FACS buffer (PBS with 2% FBS) at the concentration of 1×10⁶ cells/ml. 0.1 ug of Biotinylated human IL-6 is added into 100 ul of DS-1 cells and incubated at 4° C. for 15 min. For some of these reactions, increasing concentrations (0.1 ug to 20 ug) of anti-human IL-6 DIS-CObody or regular IgG1 antibody are added into the reactions. After 15 min, cells are washed with FACS buffer for three times and resuspended in 100 ul of FACS buffer. 1 ul of FITC-strepavidin is then added into each reaction and incubated at 4° C. for 15 min. The cells are washed three times before being analyzed using the FACS Caliber (BD, USA). The blocking activity of anti-human IL-6 mab240.g1 for IL-6 binding to DS-1 cells is lower than the mab240.g1 in regular IgG1 format, however, the anti-human IL-6 DIS-CObody is still a very strong blocking antibody for human IL-6 binding to DS-1.

Neutralize IL-6 Bioactivity in DS-1 Cell Proliferation Assay.

Human DS-1 cells are dependent on IL-6 for their proliferations in vitro. Normally, human DS-1 cells are cultured in RPMI supplemented with 10% FBS and 10 ng/ml human IL-6. To evaluate the neutralization activities of anti-human IL-6 mAbs either in the DISCObody format or regular bivalent IgG1 format, a DS-1 cell proliferation assay is established. Briefly, human DS-1 cells are washed in PBS 3× to remove residue IL-6 in the media. Cells are then re-suspended into RPMI 1640 media with 10% serum but without human IL-6 at a concentration of 5×10⁵/ml and seed into 96 well flat bottom plates at the density of 5×10⁴/well. In a separate 96-well plate, serial dilutions of 240.g1 DIS-CObody or 240.g1 IgG1 antibody are incubated in the presence of 1 ng/ml (0.038 nM) human IL-6. The premixed antibody-IL-6 complex are transferred to wells with DS-1 cells and then incubated at 37° C. in a humidified 5% $CO_2$ atmosphere. 20 ul of CellTiter96 Aqueous (Promega, CA) are then added into each well and incubate with the cells for another 6 hours to determine the numbers of proliferating cells. The inhibition of IL-6 dependent proliferation of DS-1 cells by 240.g1 DISCObody or regular bivalent IgG1 antibody are expressed as a percentage inhibition of wells treated with IL-6 only minus control wells that contained cells but no IL-6. The results indicate that anti-human IL-6 mab 240.g1 monospecific DISCObody has reduced neutralization activities against human IL-6 compared with the 240.g1 antibody in regular bivalent format. However, the results also indicate that 240.g1 monospecific DISCObody is still a very potent inhibitor for DS-1 proliferation.

In Vivo Biological Activity of Anti-Human IL-6 mab240.g1 DISCObody.

IL-6 induces the secretion of many acute response proteins into serum once injected in vivo. One of these proteins is serum amyoid A (SAA). Thus, blocking of IL-6 induced serum amyloid accumulation in vivo can be used to assess the neutralization activities of anti-IL-6 antibodies. C57BL6 mice are injected s.c. with increasing concentrations (0.005 mgs/kg to 1 mgs/kg) of anti-IL-6 240.g1DISCObody or 240.g1 regular IgG1 antibody. 24 hours later the mice are injected i.p. with 30 ug/kg of recombinant human IL-6 (R&D Systems, USA). 20 hours later, serum samples are collected from these mice and serum SAA concentrations are determined using an ELISA kit (Tridelta, Ireland). The results indicate that anti-human IL-6 mab 240.g1 monospecific DISCObody has reduced neutralization activities against human IL-6 in vivo compared with the 240.g1 antibody in regular bivalent format. However, the results also indicate that 240.g1 monospecific DISCObody is still a very potent inhibitor for human IL-6 induced SAA secretion in vivo.

Blood samples are also collected from these mice via tail bleeding at time points of 24, 48, 72, 96 and 168 hours and the presence of human IL-6 in these mice are determined. Blood sample are heated at 65° C. to disassociate human IL-6/antibody complex. The amount of human IL-6 in the blood samples is determined using a human IL-6 specific ELISA kit (R&D Systems, USA). The amount of human IL-6 bioactivities in the blood samples is determined using the DS-1 proliferation assay. The results indicate that 240.g1 DISCObody treated animal has reduced amount of human IL-6 present in the blood as compared with mice treated with 240.g1 IgG1 antibody. These results indicate that 240.g1 DISCObody treatment do not lead to accumulation of human IL-6 in the blood which have less IL-6 induced pathological effects in vivo.

EXAMPLE 10

Construction of Anti-IL6 Monospecific DISCObody and Biological Activity Study

Construction of Anti-Human TNFR1 IZI-06.1 DISCObody HC and LC Gene.

The coding sequences for anti-human TNFR1 IZI-06.1 DISCObody is assembled by PCR using similar methods described in Example 2. The CH2CH3-hinge part of the anti-human TNFR1 IZI-06.1 DISCObody is prepared as described in Example 2. The heavy chain variable sequence of anti-human TNFR1 antibody, IZI-06.1 (humanized version of clone H398), is procured from literatures (Kontermann et al, J. Immunother, Vol. 31(3), 225-234; Zettlitz et al, MAbs, 2010 Vol. 2(6):639-47; SEQ ID NO: 64). The corresponding VH gene is synthesized using PCR of overlapping oligonucleotides. The Fd gene can be generated by overlapping PCR methods using VH and human IgG1CH1, which can be PCR cloned form human B cell cDNA library. Anti-human TNFR1 IZI-06.1 DISCObody heavy chain gene (HC) is generated by overlapping PCR method using the IgG1 CH2CH3-hing gene and the anti-human TNFR1 IZI-06.1 Fd gene. The corresponding VL sequence is also obtained from the literatures (Kontermann et al, J. Immunother, Vol. 31, 3, 225-234; Zettlitz et al, MAbs, 2010 Vol. 2(6):639-47; SEQ ID NO: 65) and the corresponding VL gene is synthesized using PCR of overlapping oligonucleotides. The anti-human TNFR1 IZI-06.1 LC gene can be generated by overlapping PCR method using the VL and human IgG1Ckappa gene, which can be PCR cloned from human B cell cDNA library. As a control antibody, the heavy chain gene for the anti-human TNFR1 IZI-06.1 is also generated in the regular human IgG1 format.

Expression of Anti-Human TNFR1 IZI-06.1 DISCObody.

The HC and LC expression constructs for anti-human TNFR1 IZI-06.1 DISCObody are generated by cloning the anti-human TNFR1 IZI-06.1 DISCObody HC and LC cassettes into a mammalian expression vector, such as pcDNA3.1 (Invitrogen, San Diego, Calif.). Similarly, the HC cassette of anti-human TNFR1 IZI-06.1 in regular IgG1 format is also cloned into the pcDNA3.1 expression vector. The pcDNA3.1-IZI-06.1 DISCObody-HC and pcDNA3.1-IZI-06.1 LC constructs are co-transfected into HEK293 cells (Invitrogen, San Diego, Calif.) according to manufacturer's instructions. The anti-human TNFR1 IZI-06.1 DISCObody in the conditioned media is purified using standard protein-A chromatography. Similarly, the pcDNA3.1-IZI-06.1 IgG1-HC and pcDNA3.1-IZI-06.1 LC constructs are also co-transfected into HEK293 cells and the anti-human TNFR1

IZI-06.1 in regular IgG1 format is also purified from conditioned media using protein A chromatography.

In Vitro Characterization of Anti-Human TNFR1 IZI-06.1 DISCObody.

The binding affinity of anti-human TNFR1 antibodies can be measured using immobilized human TNFR1 Fc fusion protein. Human TNFR1 Fc fusion protein and a negative control Fc fusion protein were immobilized in a 96-well plate (60 ng/well) in PBS overnight. The coated plate is then washed and blocked with 2% BSA. IZI-06.1 DISCObody and IZI-06.1 IgG1 antibody were added to the wells in varying concentrations and bound antibodies were detected using HRP conjugated anti-human Fab antibody and standard ECL reagents. The IZI-06.1 DISCObody has lower binding affinity to TNFR1-Fc protein comparing to the bivalent IZI-06.1 IgG1 antibody.

The neutralization activity of the anti-human TNFR1 antibodies is determined using human rhabdomyosarcoma cell line Kym-1 (JCRB, Japan). Kym-1 cells are highly sensitive to TNF ($LD_{50}$<100 pg/ml) induced apoptosis which can be blocked by anti-TNFR1 antagonistic agents. Kym-1 cells are seeded 1 day before treatment in a 96-well plate (15,000 cells/well in RPMI-1640 with 5% FCS). Varying concentrations of anti-TNFR1 IZI-06.1 DISCObody and regular IZI-06.1 IgG1 are added to the cells (0.1 to 50 ug/ml) and incubate at 37° C. for 60 minutes. Recombinant human TNF (R&D System, USA) are then added to the cells to a final concentration of 1.25 ng/ml). After 20 hours, cell viabilities are determined by crystal violet staining. TNF induce a very significant amount of Kym-1 cell death which can be completed blocked by anti-TNFR1 IZI-06.1 DISCObody at concentrations above 10 ug/ml. IZI-06.1 in regular IgG1 format can also block TNF-1 induced Kym-1 cell death at lower concentrations; however, it can only block 70% of TNF induced cell death even at highest antibody dose. This is due to the fact that IZI-06.1 antibody in IgG1 format can crosslink TNFR1 and induced an agonistic signal at higher concentration. These results indicate that anti-TNFR1 IZI-06.1 antibody in monospecific DISCObody format is a better neutralizing agents than the regular bivalent IgG1 antibody. These results indicate that the anti-TNFR1 DISCObody is a better therapeutic agent for the treatment of autoimmune diseases such as rheumatoid arthritis and Crohn's disease.

EXAMPLE 11

Construction of Anti-Human PCSK9 mab300N DISCObody and the Use of this Antibody for the Treatment of Hypercholesterolemia Construction of anti-human PCSK9 mab 300N DISCObody HC and LC gene.

The coding sequences for anti-human PCSK9 mab 300N DISCObody is assembled by PCR using similar methods described in Example 2. The CH2CH3-hinge part of the anti-human PCSK9 mab 300N DISCObody is prepared as described in Example 2. The heavy chain variable sequence of anti-human PCSK9 antibody, clone 300N, is procured from published patent (WO 2010 077854; SEQ ID NO: 66). The corresponding VH gene is synthesized using PCR of overlapping oligonucleotides. The Fd gene can be generated by overlapping PCR methods using VH and human IgG1CH1, which can be PCR cloned form human B cell cDNA library. Anti-human PCSK9 mab300N DISCObody heavy chain gene (HC) is generated by overlapping PCR method using the IgG1 CH2CH3-hing gene and the anti-human PCSK9 mab300N Fd gene. The corresponding VL sequence is also obtained from the published patent (WO 2010 077854; SEQ ID NO: 67) and the corresponding VL gene is synthesized using PCR of overlapping oligonucleotides. The anti-human PCSK9 mab300N LC gene is generated by overlapping PCR method using the VL and human IgG1Ckappa gene, which is PCR cloned from human B cell cDNA library. As a control antibody, the heavy chain gene for the anti-human PCSK9 mab 300N is also generated in the regular human IgG1 format (WO 2010 077854).

Expression of Anti-Human PCSK9 mab300N DISCObody.

The HC and LC expression constructs for anti-human PCSK9 mab300N DISCObody are generated by cloning the anti-human PCSK9 mab300N DISCObody HC and LC cassettes into a mammalian expression vector, such as pcDNA3.1 (Invitrogen, San Diego, Calif.). Similarly, the HC cassette of anti-human PCSK9 mab300N in regular IgG1 format is also cloned into the pcDNA3.1 expression vector. The pcDNA3.1-300N DISCObody-HC and pcDNA3.1-300N LC constructs are cotransfected into HEK293 cells (Invitrogen, San Diego, Calif.) according to manufacturer's instructions. The anti-human PCSK9 mab300N DISCObody in the conditioned media is purified using standard protein A chromatography. Similarly, the pcDNA3.1-300N IgG1-HC and pcDNA3.1-300N LC constructs are also transfected into HEK293 cells and the anti-human PCSK9 mab300N in regular IgG1 format is also purified from conditioned media using protein A chromatography.

In Vitro Characterization of Anti-Human PCSK9 mab300N DISCObody.

The binding affinity of anti-human PCSK9 mab 300N DISCObody is determined using plate-coated human PCSK9 protein and standard ELISA protocol. The binding affinity to human PCSK9 for anti-human PCSK9 mab300N DISCObody is lower than mab300N in regular IgG1 format. This is as expected since mab300N DISCObody binds to PCSK9 in monovalent format. The biological activity of anti-PCSK9 300N DISCObody is further evaluated in vitro using LDL-uptake assay (Chan et al., PNAS, 2009, 16:106 (24):9820-5). Briefly, fluorescent BODIPY labeled LDL (Invitrogen, USA) is added to liver HepG2 cells (ATCC, USA) and incubate for three hours. The cellular uptake of labeled LDL is measured using a Safire plate reader (Tecan Systems, USA). Adding recombinant human PCSK9 (25 ug/ml) into the reaction blocks about 80% of the LDL uptake by the HepG2 cells. Anti-human PCSK9 mab300N DISCObody and mab300N IgG1 antibody at varying concentrations (1-100 ug/ml) are pre-incubated with human PCSK9 before adding the complex into the HepG2 cells. Both 300N DISCObody and 300N IgG1 antibody can effectively restore the LDL uptake by the HepG2 cells. The blocking activity for 300N DISCObody is lower than 300N IgG1 due to its mono-valency of antigen binding, it is still a very effective blocker of PCSK9 mediated LDLR down-regulation.

In Vivo Biological Activity and Pharmacokinetics of Anti-Human PCSK9 mab300N DISCObody.

The in vivo biological activity of anti-human PCSK9 mab300N DISCObody is determined using mice over-expressing human PCSK9 with AAV5 (Chan et al., PNAS, 2009, 16:106(24):9820-5). Briefly, C57BL/6 mice are injected i.v. with $5\times10^{12}$ pfu of AAV5-human PCSK9. Animal are then screened for serum non-HDL-C (LDL-C and VLDL-C) levels and animals with similar non-HDL-C levels are grouped together for anti-PCSK9 antibody treatment. Typically a 3-4 fold increase of non-HDL-C is observed in these mice. Single i.v. doses of anti-PCSK9 mab 300N DISCObody or 300N IgG1 antibody at varying doses (10-50 mgs/kg) are injected into these mice. At various time points (0, 6, 12, 24, 48, 72, 96, 144, 168 hours) after injection, the blood samples from these animals are collected via tail bleeds and serum non-HDL-C levels are determined. In addition, the presence of anti-human PCSK9 antibodies in the serum is also determined by anti-human Fc ELISA.

Both anti-human PCSK9 antibodies (300N DISCObody and 300N IgG1) can effectively lower the serum non-HDL-C in the mice to baseline levels (non-AAV5 treated animals) at higher doses (>30 mgs/kg). However, 300N DISCObody has more prolonged effects of non-HDL-C lowering effect in these mice. This can be explained by the longer PK of the 300N DISCObody. 300N IgG1 binds to human PCSK9 in bivalent format and is cleared from circulation effectively by PSCK9/LDLR recycling. The monospecific antigen binding feature of 300N DISCObody makes it less susceptible to PCSK9 mediated clearance and has longer PK and PD effects in vivo. Thus, anti-PCSK9 mab 300N in DISCObody format have significant advantages in clinical settings for the treatment of hypercholesterolemia and coronary heart disease (CHD) than antibodies in regular IgG formats.

We claim:

1. A polypeptide complex comprising:
   a first polypeptide comprising from N-terminus to C-terminus: a first antigen-binding domain, a first protein monomer, a first thiol residue-containing peptide linker and a second antigen-binding domain, and
   a second polypeptide comprising from N-terminus to C-terminus: a third antigen-binding domain, a second protein monomer, a second thiol residue-containing peptide linker and a fourth antigen-binding domain,
   wherein the first protein monomer forms a dimer with the second protein monomer, and each of the first and the second protein monomers comprises a CH3 domain from an immunoglobulin;
   wherein the first peptide linker and the second peptide linker form a disulfide bond, and each of the first thiol peptide linker and the second peptide linker independently comprises a sequence selected from the group consisting of: SEQ ID NO: 68, SEQ ID NO: 69, and SEQ ID NO: 70;
   wherein the first antigen-binding domain and the third antigen-binding domain are capable of binding to a first antigen, and the second antigen-binding domain and the fourth antigen-binding domain are capable of binding to a second antigen, and one of the first and the second antigens is human CD3 and the other is human EpCAM or human CD19, and
   wherein each of the first, second, third, and fourth antigen-binding domains is independently selected from the group consisting of VH, VL, Fab, and scFv.

2. The polypeptide complex of claim 1 wherein the disulfide bond reduces the simultaneous binding of the first antigen-binding domain and the second antigen-binding domain to the first antigen, and of the third antigen-binding domain and the fourth antigen-binding domain to the second antigen.

3. The polypeptide complex of claim 1 wherein the first protein monomer is the same as the second protein monomer.

4. The polypeptide complex of claim 1 wherein the first antigen-binding domain is the same as the second antigen-binding domain, and/or the third antigen-binding domain is the same as the fourth antigen-binding domain.

5. The polypeptide complex of claim 1 wherein the first protein monomer and/or the second protein monomer further comprise a CH2 domain from the immunoglobulin and the C-terminal of the CH2 domain is covalently linked to the N-terminal of the CH3 domain.

6. The polypeptide complex of claim 1 wherein the immunoglobulin is selected from the group consisting of IgA, IgD, IgE, IgG, and IgM.

7. The polypeptide complex of claim 1 wherein the first antigen-binding domain or the second antigen-binding domain is Fab comprising a first light chain fragment which is disulfidely bonded to a first heavy chain fragment.

8. The polypeptide complex of claim 1 wherein the first antigen-binding domain or the second antigen-binding domain is Fab comprising a second heavy chain fragment which is disulfidely bonded to a second light chain fragment.

9. A composition comprising the polypeptide complex of any of claims 1, 2-4, 5, 6, 7-8 and one or more conjugates, wherein the polypeptide complex is linked to the one or more conjugates.

10. A pharmaceutical composition comprising the polypeptide complex of any of claims 1, 2-4, 5, 6, 7-8, and a pharmaceutically acceptable carrier.

11. The polypeptide complex of claim 1 wherein the first and second antigen-binding domains are Fab and the third and fourth binding domains are scFv.

12. The polypeptide complex of claim 1 wherein the third and fourth antigen-binding domains are scFv and the first and second binding domains are Fab.

13. The polypeptide complex of claim 1 wherein the first antigen is human EpCAM or human CD19, and the second antigen is human CD3.

14. The polypeptide complex of claim 1 wherein the first antigen is human CD3, and the second antigen is human EpCAM or human CD19.

15. The polypeptide complex of claim 1 wherein the first antigen-binding domain is anti-CD3 Fab, and the second antigen-binding domain is anti-CD19 scFv.

16. The polypeptide complex of claim 1 wherein the first antigen-binding domain is anti-CD3 Fab, and the second antigen-binding domain is anti-EpCAM scFv.

* * * * *

```
                              SEQUENCE LISTING

<160> NUMBER OF SEQ ID NOS: 70

<210> SEQ ID NO 1
<211> LENGTH: 53
<212> TYPE: DNA
<213> ORGANISM: Artificial Sequence
<220> FEATURE:
<223> OTHER INFORMATION: Forward Primer

<400> SEQUENCE: 1
gaagttcaac ttcttgaaca atctggtgct gaacttgctc gtcctggtgc ttc           53

<210> SEQ ID NO 2
<211> LENGTH: 53
<212> TYPE: DNA
<213> ORGANISM: Artificial Sequence
<220> FEATURE:
<223> OTHER INFORMATION: Reverse Primer

<400> SEQUENCE: 2
gtataaccag aagctttaca agaaagttta acagaagcac caggacgagc aag           53

<210> SEQ ID NO 3
<211> LENGTH: 56
<212> TYPE: DNA
<213> ORGANISM: Artificial Sequence
<220> FEATURE:
<223> OTHER INFORMATION: Forward Primer

<400> SEQUENCE: 3
gtaaagcttc tggttatact tttactaatt atggtctttc ttgggttaaa caacgt        56

<210> SEQ ID NO 4
<211> LENGTH: 59
<212> TYPE: DNA
<213> ORGANISM: Artificial Sequence
<220> FEATURE:
<223> OTHER INFORMATION: Reverse Primer

<400> SEQUENCE: 4
ggataaactt caccaatcca ttcaagaact tgaccaggac gttgtttaac ccaagaaag     59

<210> SEQ ID NO 5
<211> LENGTH: 58
<212> TYPE: DNA
<213> ORGANISM: Artificial Sequence
<220> FEATURE:
<223> OTHER INFORMATION: Forward Primer

<400> SEQUENCE: 5
ggattggtga agtttatcct cgtattggta atgcttatta taatgaaaaa tttaaagg      58
```

```
<210> SEQ ID NO 6
<211> LENGTH: 58
<212> TYPE: DNA
<213> ORGANISM: Artificial Sequence
<220> FEATURE:
<223> OTHER INFORMATION: Reverse Primer

<400> SEQUENCE: 6
gaagaagatt tatcagcagt aagagtagct ttacctttaa attttcatt ataataag        58

<210> SEQ ID NO 7
<211> LENGTH: 54
<212> TYPE: DNA
<213> ORGANISM: Artificial Sequence
<220> FEATURE:
<223> OTHER INFORMATION: Forward Primer

<400> SEQUENCE: 7
ctgctgataa atcttcttct actgcttcta tggaacttcg ttctcttact tctg           54

<210> SEQ ID NO 8
<211> LENGTH: 56
<212> TYPE: DNA
<213> ORGANISM: Artificial Sequence
<220> FEATURE:
<223> OTHER INFORMATION: Reverse Primer

<400> SEQUENCE: 8
gaaccacgac gagcacaaaa ataaacagca gaatcttcag aagtaagaga acgaag         56

<210> SEQ ID NO 9
<211> LENGTH: 58
<212> TYPE: DNA
<213> ORGANISM: Artificial Sequence
<220> FEATURE:
<223> OTHER INFORMATION: Forward Primer

<400> SEQUENCE: 9
ttttgtgctc gtcgtggttc ttatgatact aattatgatt ggtattttga tgtttggg       58

<210> SEQ ID NO 10
<211> LENGTH: 58
<212> TYPE: DNA
<213> ORGANISM: Artificial Sequence
<220> FEATURE:
<223> OTHER INFORMATION: Reverse Primer

<400> SEQUENCE: 10
gccaccgcca ccagaagaaa cagtaacagt agtaccttga ccccaaacat caaaatac       58

<210> SEQ ID NO 11
<211> LENGTH: 58
<212> TYPE: DNA
<213> ORGANISM: Artificial Sequence
<220> FEATURE:
<223> OTHER INFORMATION: Forward Primer

<400> SEQUENCE: 11
gtttcttctg gtggcggtgg cagcggcggt ggtgggtccg gtggcggcgg atctgaac       58

<210> SEQ ID NO 12
<211> LENGTH: 57
<212> TYPE: DNA
<213> ORGANISM: Artificial Sequence
<220> FEATURE:
<223> OTHER INFORMATION: Reverse Primer
```

<400> SEQUENCE: 12
gagaaacagg aagagaaaga ggagtttgag tcataacaag ttcagatccg ccgccac    57

<210> SEQ ID NO 13
<211> LENGTH: 59
<212> TYPE: DNA
<213> ORGANISM: Artificial Sequence
<220> FEATURE:
<223> OTHER INFORMATION: Forward Primer

<400> SEQUENCE: 13
ctttctcttc ctgtttctct tggtgatcaa gcttctattt cttgtcgttc ttctcaatc    59

<210> SEQ ID NO 14
<211> LENGTH: 56
<212> TYPE: DNA
<213> ORGANISM: Artificial Sequence
<220> FEATURE:
<223> OTHER INFORMATION: Reverse Primer

<400> SEQUENCE: 14
ccaatgaaga taagtattac cattagaatg aacaagagat tgagaagaac gacaag    56

<210> SEQ ID NO 15
<211> LENGTH: 54
<212> TYPE: DNA
<213> ORGANISM: Artificial Sequence
<220> FEATURE:
<223> OTHER INFORMATION: Forward Primer

<400> SEQUENCE: 15
gtaatactta tcttcattgg tatcttcaaa aacctggtca atctcctaaa cttc    54

<210> SEQ ID NO 16
<211> LENGTH: 57
<212> TYPE: DNA
<213> ORGANISM: Artificial Sequence
<220> FEATURE:
<223> OTHER INFORMATION: Reverse Primer

<400> SEQUENCE: 16
caggaacacc agaaaaacga ttagaaactt tataaataag aagtttagga gattgac    57

<210> SEQ ID NO 17
<211> LENGTH: 57
<212> TYPE: DNA
<213> ORGANISM: Artificial Sequence
<220> FEATURE:
<223> OTHER INFORMATION: Forward Primer

<400> SEQUENCE: 17
gtttttctgg tgttcctgat cgttttctg gttctggttc tggtactgat tttactc    57

<210> SEQ ID NO 18
<211> LENGTH: 54
<212> TYPE: DNA
<213> ORGANISM: Artificial Sequence
<220> FEATURE:
<223> OTHER INFORMATION: Reverse Primer

<400> SEQUENCE: 18
caccaagatc ttcagcttca acacgagaaa ttttaagagt aaaatcagta ccag    54

<210> SEQ ID NO 19
<211> LENGTH: 56

-continued

<212> TYPE: DNA
<213> ORGANISM: Artificial Sequence
<220> FEATURE:
<223> OTHER INFORMATION: Forward Primer

<400> SEQUENCE: 19
gaagctgaag atcttggtgt ttattttgt tctcaatcta ctcatgttcc ttatac        56

<210> SEQ ID NO 20
<211> LENGTH: 45
<212> TYPE: DNA
<213> ORGANISM: Artificial Sequence
<220> FEATURE:
<223> OTHER INFORMATION: Reverse Primer

<400> SEQUENCE: 20
tttcaagttt agtaccacca ccaaaagtat aaggaacatg agtag                    45

<210> SEQ ID NO 21
<211> LENGTH: 23
<212> TYPE: DNA
<213> ORGANISM: Artificial Sequence
<220> FEATURE:
<223> OTHER INFORMATION: Forward Primer

<400> SEQUENCE: 21
gaagttcaac ttcttgaaca atc                                            23

<210> SEQ ID NO 22
<211> LENGTH: 24
<212> TYPE: DNA
<213> ORGANISM: Artificial Sequence
<220> FEATURE:
<223> OTHER INFORMATION: Reverse Primer

<400> SEQUENCE: 22
caaaagtata aggaacatga gtag                                           24

<210> SEQ ID NO 23
<211> LENGTH: 60
<212> TYPE: DNA
<213> ORGANISM: Artificial Sequence
<220> FEATURE:
<223> OTHER INFORMATION: Forward Primer

<400> SEQUENCE: 23
gagacgtacg caggtccagc tgcagcagtc tggggctgaa ctggcaagac ctggggcctc    60

<210> SEQ ID NO 24
<211> LENGTH: 59
<212> TYPE: DNA
<213> ORGANISM: Artificial Sequence
<220> FEATURE:
<223> OTHER INFORMATION: Reverse Primer

<400> SEQUENCE: 24
cctagtaaag gtgtagccag aagccttgca ggacatcttc actgaggccc caggtcttg     59

<210> SEQ ID NO 25
<211> LENGTH: 58
<212> TYPE: DNA
<213> ORGANISM: Artificial Sequence
<220> FEATURE:
<223> OTHER INFORMATION: Forward Primer

<400> SEQUENCE: 25
ctggctacac ctttactagg tacacgatgc actgggtaaa acagaggcct ggacaggg    58

<210> SEQ ID NO 26
<211> LENGTH: 59
<212> TYPE: DNA
<213> ORGANISM: Artificial Sequence
<220> FEATURE:
<223> OTHER INFORMATION: Reverse Primer

<400> SEQUENCE: 26
ccacggctag gattaatgta tccaatccat tccagaccct gtccaggcct ctgttttac    59

<210> SEQ ID NO 27
<211> LENGTH: 57
<212> TYPE: DNA
<213> ORGANISM: Artificial Sequence
<220> FEATURE:
<223> OTHER INFORMATION: Forward Primer

<400> SEQUENCE: 27
cattaatcct agccgtggtt atactaatta caatcagaag ttcaaggaca aggccac    57

<210> SEQ ID NO 28
<211> LENGTH: 59
<212> TYPE: DNA
<213> ORGANISM: Artificial Sequence
<220> FEATURE:
<223> OTHER INFORMATION: Reverse Primer

<400> SEQUENCE: 28
gttgcatgta ggctgtgctg gaggatttgt ctgtagtcaa tgtggccttg tccttgaac    59

<210> SEQ ID NO 29
<211> LENGTH: 58
<212> TYPE: DNA
<213> ORGANISM: Artificial Sequence
<220> FEATURE:
<223> OTHER INFORMATION: Forward Primer

<400> SEQUENCE: 29
cagcacagcc tacatgcaac tgagcagcct gacatctgag gactctgcag tctattac    58

<210> SEQ ID NO 30
<211> LENGTH: 58
<212> TYPE: DNA
<213> ORGANISM: Artificial Sequence
<220> FEATURE:
<223> OTHER INFORMATION: Reverse Primer

<400> SEQUENCE: 30
gtagtcaagg cagtaatgat catcataata tcttgcacag taatagactg cagagtcc    58

<210> SEQ ID NO 31
<211> LENGTH: 56
<212> TYPE: DNA
<213> ORGANISM: Artificial Sequence
<220> FEATURE:
<223> OTHER INFORMATION: Forward Primer

<400> SEQUENCE: 31
gatcattact gccttgacta ctggggccaa ggcaccactc tcacagtctc ctcagc    56

<210> SEQ ID NO 32
<211> LENGTH: 26
<212> TYPE: DNA
<213> ORGANISM: Artificial Sequence -continued

```
<220> FEATURE:
<223> OTHER INFORMATION: Reverse Primer

<400> SEQUENCE: 32
gagagctagc tgaggagact gtgaga                                              26

<210> SEQ ID NO 33
<211> LENGTH: 20
<212> TYPE: DNA
<213> ORGANISM: Artificial Sequence
<220> FEATURE:
<223> OTHER INFORMATION: Forward Primer

<400> SEQUENCE: 33
gagacgtacg caggtccagc                                                     20

<210> SEQ ID NO 34
<211> LENGTH: 18
<212> TYPE: DNA
<213> ORGANISM: Artificial Sequence
<220> FEATURE:
<223> OTHER INFORMATION: Reverse Primer

<400> SEQUENCE: 34
gctgaggaga ctgtgaga                                                       18

<210> SEQ ID NO 35
<211> LENGTH: 57
<212> TYPE: DNA
<213> ORGANISM: Artificial Sequence
<220> FEATURE:
<223> OTHER INFORMATION: Forward Primer

<400> SEQUENCE: 35
caaattgttc tcacccagtc tccagcaatc atgtctgcat ctccagggga gaaggtc            57

<210> SEQ ID NO 36
<211> LENGTH: 59
<212> TYPE: DNA
<213> ORGANISM: Artificial Sequence
<220> FEATURE:
<223> OTHER INFORMATION: Reverse Primer

<400> SEQUENCE: 36
catgtaactt acacttgagc tggcactgca ggtcatggtg accttctccc ctggagatg          59

<210> SEQ ID NO 37
<211> LENGTH: 58
<212> TYPE: DNA
<213> ORGANISM: Artificial Sequence
<220> FEATURE:
<223> OTHER INFORMATION: Forward Primer

<400> SEQUENCE: 37
gctcaagtgt aagttacatg aactggtacc agcagaagtc aggcacctcc cccaaaag          58

<210> SEQ ID NO 38
<211> LENGTH: 58
<212> TYPE: DNA
<213> ORGANISM: Artificial Sequence
<220> FEATURE:
<223> OTHER INFORMATION: Reverse Primer

<400> SEQUENCE: 38
gactccagaa gccagtttgg atgtgtcata aatccatctt ttgggggagg tgcctgac           58
```

```
<210> SEQ ID NO 39
<211> LENGTH: 58
<212> TYPE: DNA
<213> ORGANISM: Artificial Sequence
<220> FEATURE:
<223> OTHER INFORMATION: Forward Primer

<400> SEQUENCE: 39
caaactggct tctggagtcc ctgctcactt cagggcagt gggtctggga cctcttac      58

<210> SEQ ID NO 40
<211> LENGTH: 58
<212> TYPE: DNA
<213> ORGANISM: Artificial Sequence
<220> FEATURE:
<223> OTHER INFORMATION: Reverse Primer

<400> SEQUENCE: 40
gtggcagcat cttcagcctc catgccgctg attgtgagag agtaagaggt cccagacc      58

<210> SEQ ID NO 41
<211> LENGTH: 57
<212> TYPE: DNA
<213> ORGANISM: Artificial Sequence
<220> FEATURE:
<223> OTHER INFORMATION: Forward Primer

<400> SEQUENCE: 41
gaggctgaag atgctgccac ttattactgc cagcagtgga gtagtaaccc attcacg       57

<210> SEQ ID NO 42
<211> LENGTH: 59
<212> TYPE: DNA
<213> ORGANISM: Artificial Sequence
<220> FEATURE:
<223> OTHER INFORMATION: Reverse Primer

<400> SEQUENCE: 42
gagacgtacg gtttatttcc aactttgtcc ccgagccgaa cgtgaatggg ttactactc     59

<210> SEQ ID NO 43
<211> LENGTH: 20
<212> TYPE: DNA
<213> ORGANISM: Artificial Sequence
<220> FEATURE:
<223> OTHER INFORMATION: Forward Primer

<400> SEQUENCE: 43
caaattgttc tcacccagtc                                                20

<210> SEQ ID NO 44
<211> LENGTH: 19
<212> TYPE: DNA
<213> ORGANISM: Artificial Sequence
<220> FEATURE:
<223> OTHER INFORMATION: Reverse Primer

<400> SEQUENCE: 44
cgtgaatggg ttactactc                                                 19

<210> SEQ ID NO 45
<211> LENGTH: 22
<212> TYPE: DNA
<213> ORGANISM: Artificial Sequence
<220> FEATURE:
<223> OTHER INFORMATION: Forward Primer
```

```
<400> SEQUENCE: 45
gctagcacca agggcccatc cg                                              22

<210> SEQ ID NO 46
<211> LENGTH: 19
<212> TYPE: DNA
<213> ORGANISM: Artificial Sequence
<220> FEATURE:
<223> OTHER INFORMATION: Reverse Primer

<400> SEQUENCE: 46
tttccccgga gacagggag                                                  19

<210> SEQ ID NO 47
<211> LENGTH: 30
<212> TYPE: DNA
<213> ORGANISM: Artificial Sequence
<220> FEATURE:
<223> OTHER INFORMATION: Forward Primer

<400> SEQUENCE: 47
cgtacggtgg ctgcaccatc tgtcttcatc                                      30

<210> SEQ ID NO 48
<211> LENGTH: 20
<212> TYPE: DNA
<213> ORGANISM: Artificial Sequence
<220> FEATURE:
<223> OTHER INFORMATION: Reverse Primer

<400> SEQUENCE: 48
acactctccc ctgttgaagc                                                 20

<210> SEQ ID NO 49
<211> LENGTH: 56
<212> TYPE: DNA
<213> ORGANISM: Artificial Sequence
<220> FEATURE:
<223> OTHER INFORMATION: Forward Primer

<400> SEQUENCE: 49
actcacacat gcccaccgtg cccagcacca cgtacgcagg tccagctgca gcagtc         56

<210> SEQ ID NO 50
<211> LENGTH: 40
<212> TYPE: DNA
<213> ORGANISM: Artificial Sequence
<220> FEATURE:
<223> OTHER INFORMATION: Reverse Primer

<400> SEQUENCE: 50
gatgggccct tggtgctagc tgaggagact gtgagagtgg                           40

<210> SEQ ID NO 51
<211> LENGTH: 37
<212> TYPE: DNA
<213> ORGANISM: Artificial Sequence
<220> FEATURE:
<223> OTHER INFORMATION: Reverse Primer

<400> SEQUENCE: 51
gagaggatcc tcaagttttg tcacaagatt tgggctc                              37

<210> SEQ ID NO 52
```

```
<210> SEQ ID NO 52
<211> LENGTH: 55
<212> TYPE: DNA
<213> ORGANISM: Artificial Sequence
<220> FEATURE:
<223> OTHER INFORMATION: Forward Primer

<400> SEQUENCE: 52 cttttcttg tggctatttt aaaaggtgtc cagtgtgggg gaccgtcagt cttcc        55

<210> SEQ ID NO 53
<211> LENGTH: 58
<212> TYPE: DNA
<213> ORGANISM: Artificial Sequence
<220> FEATURE:
<223> OTHER INFORMATION: Forward Primer

<400> SEQUENCE: 53
gccaccggat ccatggagtt tgggctgagc tggcttttc ttgtggctat tttaaaag    58

<210> SEQ ID NO 54
<211> LENGTH: 40
<212> TYPE: DNA
<213> ORGANISM: Artificial Sequence
<220> FEATURE:
<223> OTHER INFORMATION: Reverse Primer

<400> SEQUENCE: 54
cggtgggcat gtgtgagttt tccccggaga cagggagagg                        40

<210> SEQ ID NO 55
<211> LENGTH: 59
<212> TYPE: DNA
<213> ORGANISM: Artificial Sequence
<220> FEATURE:
<223> OTHER INFORMATION: Forward Primer

<400> SEQUENCE: 55 cttttcttg tggctatttt aaaaggtgtc cagtgtgaag ttcaacttct tgaacaatc    59

<210> SEQ ID NO 56
<211> LENGTH: 41
<212> TYPE: DNA
<213> ORGANISM: Artificial Sequence
<220> FEATURE:
<223> OTHER INFORMATION: Reverse Primer

<400> SEQUENCE: 56
gaggaagact gacggtcccc ctttaatttc aagtttagta c                      41

<210> SEQ ID NO 57
<211> LENGTH: 41
<212> TYPE: DNA
<213> ORGANISM: Artificial Sequence
<220> FEATURE:
<223> OTHER INFORMATION: Forward Primer

<400> SEQUENCE: 57
gtactaaact tgaaattaaa gggggaccgt cagtcttcct c                      41

<210> SEQ ID NO 58
<211> LENGTH: 56
<212> TYPE: DNA
<213> ORGANISM: Artificial Sequence
<220> FEATURE:
<223> OTHER INFORMATION: Forward Primer

<400> SEQUENCE: 58
``` cttttttcttg tggctatttt aaaaggtgtc cagtgtcaaa ttgttctcac ccagtc       56

<210> SEQ ID NO 59
<211> LENGTH: 39
<212> TYPE: DNA
<213> ORGANISM: Artificial Sequence
<220> FEATURE:
<223> OTHER INFORMATION: Reverse Primer

<400> SEQUENCE: 59
gatggtgcag ccaccgtacg gtttatttcc aactttgtc       39

<210> SEQ ID NO 60
<211> LENGTH: 39
<212> TYPE: DNA
<213> ORGANISM: Artificial Sequence
<220> FEATURE:
<223> OTHER INFORMATION: Forward Primer

<400> SEQUENCE: 60
gacaaagttg gaaataaacc gtacggtggc tgcaccatc       39

<210> SEQ ID NO 61
<211> LENGTH: 30
<212> TYPE: DNA
<213> ORGANISM: Artificial Sequence
<220> FEATURE:
<223> OTHER INFORMATION: Reverse Primer

<400> SEQUENCE: 61
gagaggatcc acactctccc ctgttgaagc       30

<210> SEQ ID NO 62
<211> LENGTH: 357
<212> TYPE: DNA
<213> ORGANISM: Artificial Sequence
<220> FEATURE:
<223> OTHER INFORMATION: heavy chain variable region for humanized
    antibody mab 240.g1

<400> SEQUENCE: 62
gaggtgcaaa ttttggagac tggaggaggc ttggtgaagc ccggtggttc cctgagactg       60
tcttgtgcaa cgtctggatt caacttcaat gattatttca tgaactgggt ccgtcaggct      120
ccagggaagg gactagagtg gcttgctcaa atgagaaaca aaattatca atatggcaca       180
tattatgcgg agtctttgga aggcagagtc acagtctcac gagacgatgc caaaaacagt      240
gtctacctgc aagtgagcag tttaagagct gaggacacgg ccatttatta ctgtacaaga      300
gagtcatact acggctttac ctcctactgg ggccaaggag tcatggtcac agtctcg         357

<210> SEQ ID NO 63
<211> LENGTH: 321
<212> TYPE: DNA
<213> ORGANISM: Artificial Sequence
<220> FEATURE:
<223> OTHER INFORMATION: light chain variable region for humanized
    antibody mab 240.g1

<400> SEQUENCE: 63
gacatccaga tgacacagtc tcctgcctcc ctgtctgcat ctctggaaga aattgtcacc       60
atcacatgcc aggcaagcca ggacattggt atttctttat catggtatca gcagaaacca      120
gggaggactc ctcagctcct gatccaaaat gcaaacaact ggcagatggg ggtcccatca      180

| | |
|---|---|
| aggttcagcg gccgtagatt tggcacacag ttttctctta cgatcagtac accacaggtt | 240 |
| gaagatactg gagtctatta ctgtctccag cataatagtg ctccgtacac gtttggaact | 300 |
| gggacccagc tggaaatcaa a | 321 |

```
<210> SEQ ID NO 64
<211> LENGTH: 345
<212> TYPE: DNA
<213> ORGANISM: Artificial Sequence
<220> FEATURE:
<223> OTHER INFORMATION: heavy chain variable region for humanized
      antibody IZI-06.1

<400> SEQUENCE: 64
```

| | |
|---|---|
| caggttcagc tggttcagag cggtgcggaa gtgaaaaaac cgggcagcag cgtgaaagtg | 60 |
| agctgcaaag cgagcggcta cctttacc gatttctaca ttaactgggt gcgtcaggca | 120 |
| ccgggtcagg gcctggaatg gattggcgaa atttatccgt atagcggcca tgcatattac | 180 |
| aacgaaaaat tcaaagcgcg tgtgaccatt accgcggata aaagcaccag caccgcgtat | 240 |
| atggaactga gcagcctgcg tagcgaagat accgcggtgt attattgcgc gcgttgggat | 300 |
| tttctggatt attggggcca gggcaccacc gttacggtct cgagt | 345 |

```
<210> SEQ ID NO 65
<211> LENGTH: 339
<212> TYPE: DNA
<213> ORGANISM: Artificial Sequence
<220> FEATURE:
<223> OTHER INFORMATION: light chain variable region for humanized
      antibody IZI-06.1

<400> SEQUENCE: 65
```

| | |
|---|---|
| gatattgtga tgacccagag cccgctgtct ctgccggtca cgccgggtga accggcgagc | 60 |
| attagctgcc gtagcagcca gagcctgctg catagcaacg gcaacaccta tctgcattgg | 120 |
| tatctgcaga aaccgggcca gagcccgcag ctgctgattt ataccgtgag caaccgtttt | 180 |
| agcggcgtgc cggatcgctt tagcggcagc ggtagcggca ccgatttta cctgaaaatt | 240 |
| agccgtgtgg aagcggaaga tgtgggcgtg tattattgca gccagagcac ccatgtgccg | 300 |
| tatacctttg gcggtggcac caaagtggaa attaaacgt | 339 |

```
<210> SEQ ID NO 66
<211> LENGTH: 381
<212> TYPE: DNA
<213> ORGANISM: Artificial Sequence
<220> FEATURE:
<223> OTHER INFORMATION: heavy chain variable region for humanized
      antibody 300N

<400> SEQUENCE: 66
```

| | |
|---|---|
| gagatgcaac tggtggagtc tgggggaggc ttggtccagc ctgggggtc cctgagactc | 60 |
| tcctgtgcag cctctggatt cacctttagt agtcactgga tgaagtgggt ccgccaggct | 120 |
| ccagggaagg gctggagtg gtggccaac ataaaccaag atggaagtga gaaatactat | 180 |
| gtggactctg tgaagggccg attcaccatc tccagagaca acgccaagaa ctcactgttt | 240 |
| ctgcaaatga acagcctgag agccgaggac acggctgtgt attactgtgc gagagatatt | 300 |
| gtactaatgg tctatgatat ggactactac tactacggta tggacgtctg gggccaaggg | 360 |
| accacggtca ccgtctcctc a | 381 |

```
<210> SEQ ID NO 67
```

```
<211> LENGTH: 335
<212> TYPE: DNA
<213> ORGANISM: Artificial Sequence
<220> FEATURE:
<223> OTHER INFORMATION: light chain variable region for humanized
      antibody 300N

<400> SEQUENCE: 67
gatattgtga tgactcagtc tccactctcc ctgcccgtca cccctggaga gccggcctca      60
tctcctgcag gtctagtcag agcctcctgc atagtaatgg aaacaactat ttggattggt     120
acctgcagaa gccagggcag tctccacagc tcctgatcta tttgggttct aatcgggcct     180
ccggggtccc tgacaggttc agtggcagtg gatcaggcac agattttaca ctgaaaatca     240
gcagagtgga ggctgaggat gttggggttt attactgcat gcaaactcta caaactccgc     300
tcactttcgg cggagggacc aaggtggaga tcaaa                                335

<210> SEQ ID NO 68
<211> LENGTH: 4
<212> TYPE: PRT
<213> ORGANISM: Artificial Sequence
<220> FEATURE:
<223> OTHER INFORMATION: Hinge sequence

<400> SEQUENCE: 68

Cys Pro Pro Cys
1

<210> SEQ ID NO 69
<211> LENGTH: 10
<212> TYPE: PRT
<213> ORGANISM: Artificial Sequence
<220> FEATURE:
<223> OTHER INFORMATION: Hinge sequence

<400> SEQUENCE: 69

Thr His Thr Cys Pro Pro Cys Pro Ala Pro
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Hinge sequence

<400> SEQUENCE: 70

Asp Lys Thr His Thr Cys Pro Pro Cys Pro Ala Pro
1               5                   10
```